(12) United States Patent
Ramasubramanyan et al.

(10) Patent No.: US 9,334,319 B2
(45) Date of Patent: *May 10, 2016

(54) LOW ACIDIC SPECIES COMPOSITIONS

(71) Applicant: ABBVIE INC., North Chicago, IL (US)

(72) Inventors: Natarajan Ramasubramanyan, Westborough, MA (US); Lihua Yang, Westborough, MA (US); Matthew Omon Herigstad, Charlestown, MA (US); Hong Yang, Worcester, MA (US); Christopher Chumsae, North Andover, MA (US)

(73) Assignee: AbbVie Inc., North Chicago, IL (US)

( * ) Notice: Subject to any disclaimer, the term of this patent is extended or adjusted under 35 U.S.C. 154(b) by 212 days.

This patent is subject to a terminal disclaimer.

(21) Appl. No.: 13/829,989

(22) Filed: Mar. 14, 2013

(65) Prior Publication Data
US 2013/0338344 A1 Dec. 19, 2013

Related U.S. Application Data

(60) Provisional application No. 61/636,511, filed on Apr. 20, 2012.

(51) Int. Cl.
| | | |
|---|---|---|
| C07K 16/00 | (2006.01) | |
| C12P 21/08 | (2006.01) | |
| A61K 39/395 | (2006.01) | |
| C07K 16/24 | (2006.01) | |
| C07K 1/16 | (2006.01) | |
| C07K 1/18 | (2006.01) | |
| C12P 21/00 | (2006.01) | |
| C07K 1/20 | (2006.01) | |
| C07K 1/22 | (2006.01) | |

(52) U.S. Cl.
CPC .......... *C07K 16/241* (2013.01); *A61K 39/39591* (2013.01); *C07K 1/165* (2013.01); *C07K 1/18* (2013.01); *C07K 1/20* (2013.01); *C07K 1/22* (2013.01); *C07K 16/00* (2013.01); *C12P 21/00* (2013.01); *C07K 2317/14* (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,399,216 A | 8/1983 | Axel et al. |
| 4,510,245 A | 4/1985 | Cousens et al. |
| 4,560,655 A | 12/1985 | Baker |
| 4,634,665 A | 1/1987 | Axel et al. |
| 4,657,866 A | 4/1987 | Kumar |
| 4,767,704 A | 8/1988 | Cleveland et al. |
| 4,801,687 A | 1/1989 | Ngo |
| 4,816,397 A | 3/1989 | Boss et al. |
| 4,877,608 A | 10/1989 | Lee et al. |
| 4,927,762 A | 5/1990 | Darfler |
| 4,933,435 A | 6/1990 | Ngo |
| 4,968,615 A | 11/1990 | Koszinowski et al. |
| 5,045,468 A | 9/1991 | Darfler |
| 5,096,816 A | 3/1992 | Maiorella |
| 5,110,913 A | 5/1992 | Coan et al. |
| 5,118,796 A | 6/1992 | Prior et al. |
| 5,122,469 A | 6/1992 | Mather et al. |
| 5,126,250 A | 6/1992 | McDonough et al. |
| 5,168,062 A | 12/1992 | Stinski |
| 5,179,017 A | 1/1993 | Axel et al. |
| 5,231,024 A | 7/1993 | Moeller et al. |
| 5,328,985 A | 7/1994 | Sano et al. |
| 5,378,612 A | 1/1995 | Nakashima et al. |
| 5,429,746 A | 7/1995 | Shadle et al. |
| 5,530,101 A | 6/1996 | Queen et al. |
| 5,545,403 A | 8/1996 | Page |
| 5,545,806 A | 8/1996 | Lonberg et al. |
| 5,545,807 A | 8/1996 | Surani et al. |
| 5,561,053 A | 10/1996 | Crowley |
| 5,569,825 A | 10/1996 | Lonberg et al. |
| 5,625,126 A | 4/1997 | Lonberg et al. |
| 5,633,162 A | 5/1997 | Keen et al. |
| 5,633,425 A | 5/1997 | Lonberg et al. |
| 5,644,036 A | 7/1997 | Ramage et al. |
| 5,654,407 A | 8/1997 | Boyle et al. |
| 5,656,272 A | 8/1997 | Le et al. |
| 5,661,016 A | 8/1997 | Lonberg et al. |

(Continued)

FOREIGN PATENT DOCUMENTS

| | | |
|---|---|---|
| CN | 1299370 A | 6/2001 |
| CN | 1563090 A | 1/2005 |

(Continued)

OTHER PUBLICATIONS

Rau "Adalimumab (a fully human anti-tumour necrosis factor alpha monoclonal antibody) in the treatment of active rheumatoid arthritis: the initial results of five trials" Ann Rheum Dis 2002, 61 (Suppl II): ii70-ii73.*
U.S. Appl. No. 14/079,076.
U.S. Appl. No. 14/077,988.
U.S. Appl. No. 14/077,871.
U.S. Appl. No. 14/077,574.
U.S. Appl. No. 14/077,576.
U.S. Appl. No. 61/893,123.
Boswell et al. "Effects of Charge on Antibody Tissue Distribution and Pharmacokinetics" Bioconjugate Chem.(21) 2153-2163 (2010).
Schiestl et al. "Acceptable changes in quality attributes of glycosylated biopharmaceuticals" Nature Biotechnology, 29(4), 310-312 (2011).
Senczuk et al. "Hydrophobic interaction chromatography in dual salt system increases protein binding capacity" Biotechnology and Bioengineering, 103(5), 930-935 (2009).

(Continued)

*Primary Examiner* — Daniel E Kolker
*Assistant Examiner* — James Rogers
(74) *Attorney, Agent, or Firm* — McCarter & English, LLP; Maria Laccotripe Zacharakis; Lisa Tyner

(57) ABSTRACT

The instant invention relates to the field of protein production and purification, and in particular to compositions and processes for controlling the amount of charge variants, aggregates, and fragments of a protein of interest, as well as host cell proteins, present in purified preparations by applying particular chromatography conditions during such protein purification.

61 Claims, 24 Drawing Sheets

(56) References Cited

U.S. PATENT DOCUMENTS

| | | |
|---|---|---|
| 5,672,347 A | 9/1997 | Aggarwal et al. |
| 5,672,502 A | 9/1997 | Birch et al. |
| 5,698,195 A | 12/1997 | Le et al. |
| 5,705,364 A | 1/1998 | Etcheverry et al. |
| 5,721,121 A | 2/1998 | Etcheverry et al. |
| 5,770,429 A | 6/1998 | Lonberg et al. |
| 5,789,650 A | 8/1998 | Lonberg et al. |
| 5,795,967 A | 8/1998 | Aggarwal et al. |
| 5,811,299 A | 9/1998 | Renner et al. |
| 5,859,205 A | 1/1999 | Adair et al. |
| 5,876,961 A | 3/1999 | Crowe et al. |
| 5,877,293 A | 3/1999 | Adair et al. |
| 5,929,212 A | 7/1999 | Jolliffe et al. |
| 5,945,098 A | 8/1999 | Sarno et al. |
| 5,976,833 A | 11/1999 | Furukawa et al. |
| 5,994,510 A | 11/1999 | Adair et al. |
| 6,024,938 A | 2/2000 | Corbo et al. |
| 6,036,978 A | 3/2000 | Gombotz et al. |
| 6,048,728 A | 4/2000 | Inlow et al. |
| 6,066,719 A | 5/2000 | Zapata |
| 6,075,181 A | 6/2000 | Kucherlapati et al. |
| 6,090,382 A * | 7/2000 | Salfeld et al. ............... 424/133.1 |
| 6,113,898 A | 9/2000 | Anderson et al. |
| 6,150,584 A | 11/2000 | Kucherlapati et al. |
| 6,171,586 B1 | 1/2001 | Lam et al. |
| 6,255,458 B1 | 7/2001 | Lonberg et al. |
| 6,258,562 B1 | 7/2001 | Salfeld et al. |
| 6,270,766 B1 | 8/2001 | Feldman et al. |
| 6,300,129 B1 | 10/2001 | Lonberg et al. |
| 6,339,142 B1 | 1/2002 | Basey et al. |
| 6,399,381 B1 | 6/2002 | Blum et al. |
| 6,406,909 B1 | 6/2002 | Shibuya et al. |
| 6,410,270 B1 | 6/2002 | Strittmatter et al. |
| 6,413,746 B1 | 7/2002 | Field |
| 6,436,397 B1 | 8/2002 | Baker et al. |
| 6,448,380 B2 | 9/2002 | Rathjen et al. |
| 6,451,983 B2 | 9/2002 | Rathjen et al. |
| 6,489,447 B1 | 12/2002 | Basey et al. |
| 6,498,237 B2 | 12/2002 | Rathjen et al. |
| 6,509,015 B1 | 1/2003 | Salfeld et al. |
| 6,528,286 B1 | 3/2003 | Ryll |
| 6,593,458 B1 | 7/2003 | Rathjen et al. |
| 6,673,986 B1 | 1/2004 | Kucherlapati et al. |
| 6,680,181 B2 | 1/2004 | Castan |
| 6,870,034 B2 | 3/2005 | Breece et al. |
| 6,872,549 B2 | 3/2005 | Van Ness et al. |
| 6,890,736 B1 | 5/2005 | Reddy et al. |
| 6,900,056 B2 | 5/2005 | Lee et al. |
| 6,914,128 B1 | 7/2005 | Salfeld et al. |
| 6,924,124 B1 | 8/2005 | Singh |
| 6,974,681 B1 | 12/2005 | McGrew |
| 7,070,775 B2 | 7/2006 | Le et al. |
| 7,084,260 B1 | 8/2006 | Lonberg et al. |
| 7,122,641 B2 | 10/2006 | Vedantham et al. |
| 7,189,820 B2 | 3/2007 | Ruben |
| 7,192,584 B2 | 3/2007 | Le et al. |
| 7,223,394 B2 | 5/2007 | Salfeld et al. |
| 7,250,165 B2 | 7/2007 | Heavner et al. |
| 7,276,239 B2 | 10/2007 | Le et al. |
| 7,323,553 B2 | 1/2008 | Fahrner et al. |
| 7,332,303 B2 | 2/2008 | Schilling et al. |
| 7,390,660 B2 | 6/2008 | Behrendt et al. |
| 7,429,491 B2 | 9/2008 | Luan et al. |
| 7,504,485 B2 | 3/2009 | Salfeld et al. |
| 7,521,206 B2 | 4/2009 | Heavner et al. |
| 7,521,210 B2 | 4/2009 | Knudsen |
| 7,541,031 B2 | 6/2009 | Salfeld et al. |
| 7,588,761 B2 | 9/2009 | Salfeld et al. |
| 7,645,609 B2 | 1/2010 | Follstad |
| 7,714,112 B2 | 5/2010 | Engstrand et al. |
| 7,750,129 B2 | 7/2010 | Johansson et al. |
| 7,767,207 B2 | 8/2010 | Ghayer et al. |
| 7,863,426 B2 | 1/2011 | Wan et al. |
| 7,883,704 B2 | 2/2011 | Salfeld et al. |
| 7,919,264 B2 | 4/2011 | Maksymowych et al. |
| 7,947,471 B2 | 5/2011 | Knudsen |
| 7,972,810 B2 | 7/2011 | Crowell et al. |
| 8,067,182 B2 | 11/2011 | Kelley et al. |
| 8,093,045 B2 | 1/2012 | Pla et al. |
| 8,192,951 B2 | 6/2012 | Wang et al. |
| 8,197,813 B2 | 6/2012 | Salfeld et al. |
| 8,206,714 B2 | 6/2012 | Salfeld et al. |
| 8,209,132 B2 | 6/2012 | Bosques et al. |
| 8,231,876 B2 | 7/2012 | Wan et al. |
| 8,361,797 B2 | 1/2013 | Osborne et al. |
| 8,372,400 B2 | 2/2013 | Salfeld et al. |
| 8,372,401 B2 | 2/2013 | Salfeld et al. |
| 8,414,894 B2 | 4/2013 | Salfeld et al. |
| 8,420,081 B2 | 4/2013 | Fraunhofer et al. |
| 8,436,149 B2 | 5/2013 | Borhani et al. |
| 8,470,552 B2 | 6/2013 | Croughan et al. |
| 8,663,945 B2 | 3/2014 | Pla et al. |
| 8,753,633 B2 | 6/2014 | Salfeld et al. |
| 8,821,865 B2 | 9/2014 | Neu et al. |
| 8,883,146 B2 | 11/2014 | Fraunhofer et al. |
| 8,883,156 B2 | 11/2014 | Wan et al. |
| 8,895,009 B2 | 11/2014 | Wan et al. |
| 8,895,709 B2 | 11/2014 | Hickman et al. |
| 8,906,372 B2 | 12/2014 | Wan et al. |
| 8,906,646 B2 | 12/2014 | Pla et al. |
| 8,911,964 B2 | 12/2014 | Pla et al. |
| 8,916,153 B2 | 12/2014 | Wan et al. |
| 8,921,526 B2 | 12/2014 | Chumsae et al. |
| 8,946,395 B1 * | 2/2015 | Herigstad et al. ............ 530/412 |
| 9,017,687 B1 * | 4/2015 | Wang et al. ................ 424/158.1 |
| 9,062,106 B2 | 6/2015 | Bengea et al. |
| 9,067,990 B2 | 6/2015 | Wang et al. |
| 9,085,618 B2 | 7/2015 | Ramasubramanyan et al. |
| 9,085,619 B2 | 7/2015 | Fraunhofer et al. |
| 9,090,688 B2 | 7/2015 | Bengea et al. |
| 2002/0045207 A1 | 4/2002 | Krummen et al. |
| 2002/0132299 A1 | 9/2002 | Field |
| 2002/0187526 A1 | 12/2002 | Ruben et al. |
| 2003/0012786 A1 | 1/2003 | Teoh et al. |
| 2003/0049725 A1 | 3/2003 | Heavner et al. |
| 2003/0096414 A1 | 5/2003 | Ciccarone et al. |
| 2003/0125247 A1 | 7/2003 | Rosen et al. |
| 2003/0153735 A1 | 8/2003 | Breece et al. |
| 2003/0157108 A1 | 8/2003 | Presta |
| 2003/0161828 A1 | 8/2003 | Abdelghany et al. |
| 2003/0166869 A1 | 9/2003 | Vedantham et al. |
| 2003/0175884 A1 | 9/2003 | Umana et al. |
| 2003/0178368 A1 | 9/2003 | van Reis |
| 2003/0206898 A1 | 11/2003 | Fischkoff et al. |
| 2003/0219438 A1 | 11/2003 | Salfeld et al. |
| 2003/0229212 A1 | 12/2003 | Fahrner et al. |
| 2003/0235585 A1 | 12/2003 | Fischkoff et al. |
| 2004/0009172 A1 | 1/2004 | Fischkoff et al. |
| 2004/0029229 A1 | 2/2004 | Reeves et al. |
| 2004/0033228 A1 | 2/2004 | Krause et al. |
| 2004/0033535 A1 | 2/2004 | Boyle et al. |
| 2004/0038878 A1 | 2/2004 | Tanikawa et al. |
| 2004/0101939 A1 | 5/2004 | Santora et al. |
| 2004/0120952 A1 | 6/2004 | Knight et al. |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0132140 A1 | 7/2004 | Satoh et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0162414 A1 | 8/2004 | Santora et al. |
| 2004/0166111 A1 | 8/2004 | Kaymakcalan et al. |
| 2004/0171152 A1 | 9/2004 | Price et al. |
| 2004/0191243 A1 | 9/2004 | Chen et al. |
| 2004/0214289 A1 | 10/2004 | deVries et al. |
| 2004/0219142 A1 | 11/2004 | Banerjee et al. |
| 2005/0004354 A1 | 1/2005 | Salfeld et al. |
| 2005/0100965 A1 | 5/2005 | Ghayur et al. |
| 2005/0123541 A1 | 6/2005 | Heavner et al. |
| 2005/0175611 A1 | 8/2005 | Mahler et al. |
| 2005/0249735 A1 | 11/2005 | Le et al. |
| 2005/0271654 A1 | 12/2005 | Rinderknecht et al. |

(56) References Cited

U.S. PATENT DOCUMENTS

| | | |
|---|---|---|
| 2005/0272124 A1 | 12/2005 | Chen et al. |
| 2006/0009385 A1 | 1/2006 | Hoffman et al. |
| 2006/0018907 A1 | 1/2006 | Le et al. |
| 2006/0024293 A1 | 2/2006 | Salfeld et al. |
| 2006/0083741 A1 | 4/2006 | Hoffman et al. |
| 2006/0149042 A1 | 7/2006 | Konstantinov et al. |
| 2006/0153846 A1 | 7/2006 | Krause et al. |
| 2006/0246073 A1 | 11/2006 | Knight et al. |
| 2006/0252672 A1 | 11/2006 | Betenbaugh et al. |
| 2006/0269479 A1 | 11/2006 | Colton et al. |
| 2006/0287432 A1 | 12/2006 | Christensen et al. |
| 2007/0003548 A1 | 1/2007 | Heavner et al. |
| 2007/0004009 A1 | 1/2007 | Dixit et al. |
| 2007/0041905 A1 | 2/2007 | Hoffman et al. |
| 2007/0060741 A1 | 3/2007 | Kelley et al. |
| 2007/0071747 A1 | 3/2007 | Hoffman et al. |
| 2007/0081996 A1 | 4/2007 | Hoffman et al. |
| 2007/0110743 A1 | 5/2007 | Drapeau et al. |
| 2007/0111284 A1 | 5/2007 | Ryll |
| 2007/0161084 A1 | 7/2007 | Crowell et al. |
| 2007/0172475 A1 | 7/2007 | Matheus et al. |
| 2007/0172897 A1 | 7/2007 | Maksymowych et al. |
| 2007/0184045 A1 | 8/2007 | Doctor et al. |
| 2007/0184529 A1 | 8/2007 | Etcheverry et al. |
| 2007/0190057 A1 | 8/2007 | Wu et al. |
| 2007/0196373 A1 | 8/2007 | Le et al. |
| 2007/0202051 A1 | 8/2007 | Schuschnig |
| 2007/0202104 A1 | 8/2007 | Banerjee et al. |
| 2007/0269463 A1 | 11/2007 | Donovan |
| 2007/0292442 A1 | 12/2007 | Wan et al. |
| 2007/0298040 A1 | 12/2007 | Le et al. |
| 2008/0025976 A1 | 1/2008 | Le et al. |
| 2008/0112953 A1 | 5/2008 | McAuley et al. |
| 2008/0118496 A1 | 5/2008 | Medich et al. |
| 2008/0131374 A1 | 6/2008 | Medich et al. |
| 2008/0160577 A1 | 7/2008 | Dell'Orco et al. |
| 2008/0166348 A1 | 7/2008 | Kupper et al. |
| 2008/0193466 A1 | 8/2008 | Banerjee et al. |
| 2008/0219952 A1 | 9/2008 | Fischer et al. |
| 2008/0227136 A1 | 9/2008 | Pla et al. |
| 2008/0269132 A1 | 10/2008 | Gomes et al. |
| 2008/0269468 A1 | 10/2008 | Vogel et al. |
| 2008/0274507 A1 | 11/2008 | Gomes et al. |
| 2008/0292642 A1 | 11/2008 | Borhani et al. |
| 2008/0305114 A1 | 12/2008 | Salfeld et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0053786 A1 | 2/2009 | Kao et al. |
| 2009/0060910 A1 | 3/2009 | Johnson et al. |
| 2009/0068172 A1 | 3/2009 | Kaymakcalan et al. |
| 2009/0068705 A1 | 3/2009 | Drapeau et al. |
| 2009/0110679 A1 | 4/2009 | Li et al. |
| 2009/0123378 A1 | 5/2009 | Wong et al. |
| 2009/0142828 A1 | 6/2009 | Bucciarelli et al. |
| 2009/0148513 A1 | 6/2009 | Fraunhofer et al. |
| 2009/0155205 A1 | 6/2009 | Salfeld et al. |
| 2009/0175857 A1 | 7/2009 | Salfeld et al. |
| 2009/0202546 A1 | 8/2009 | Harris et al. |
| 2009/0202557 A1 | 8/2009 | Argiriadi et al. |
| 2009/0203055 A1 | 8/2009 | Ngantung et al. |
| 2009/0208500 A1 | 8/2009 | Joly et al. |
| 2009/0226530 A1 | 9/2009 | Lassner et al. |
| 2009/0239259 A1 | 9/2009 | Hsieh |
| 2009/0258018 A1 | 10/2009 | Medich et al. |
| 2009/0269302 A1 | 10/2009 | Salfeld et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong |
| 2010/0034823 A1 | 2/2010 | Borhani et al. |
| 2010/0040604 A1 | 2/2010 | Salfeld et al. |
| 2010/0040630 A1 | 2/2010 | Elden et al. |
| 2010/0135987 A1 | 6/2010 | Hickman et al. |
| 2010/0136025 A1 | 6/2010 | Hickman et al. |
| 2010/0160894 A1 | 6/2010 | Julian et al. |
| 2010/0172911 A1 | 7/2010 | Naso et al. |
| 2010/0221823 A1 | 9/2010 | McCoy et al. |
| 2010/0256336 A1 | 10/2010 | Yuk et al. |
| 2010/0278822 A1 | 11/2010 | Fraunhofer et al. |
| 2010/0297697 A1 | 11/2010 | Ambrosius et al. |
| 2011/0002935 A1* | 1/2011 | Wan et al. .................. 424/142.1 |
| 2011/0003338 A1 | 1/2011 | Bayer et al. |
| 2011/0053223 A1 | 3/2011 | Bayer et al. |
| 2011/0053265 A1 | 3/2011 | Follstad et al. |
| 2011/0054414 A1 | 3/2011 | Shang et al. |
| 2011/0081679 A1 | 4/2011 | Jing et al. |
| 2011/0081700 A1 | 4/2011 | Hasslacher et al. |
| 2011/0086798 A1 | 4/2011 | Sethuraman et al. |
| 2011/0097336 A1 | 4/2011 | Wu et al. |
| 2011/0123544 A1 | 5/2011 | Salfeld et al. |
| 2011/0130544 A1 | 6/2011 | Ram et al. |
| 2011/0171227 A1 | 7/2011 | Okun et al. |
| 2011/0207676 A1 | 8/2011 | Callewaert et al. |
| 2011/0300151 A1 | 12/2011 | Okun et al. |
| 2012/0014956 A1 | 1/2012 | Kupper et al. |
| 2012/0015438 A1 | 1/2012 | Schilling et al. |
| 2012/0039900 A1 | 2/2012 | Stuhlmuller et al. |
| 2012/0039908 A1 | 2/2012 | Combs et al. |
| 2012/0077213 A1 | 3/2012 | Pla et al. |
| 2012/0107783 A1 | 5/2012 | Julian et al. |
| 2012/0123688 A1 | 5/2012 | Ramasubramanyan et al. |
| 2012/0129185 A1 | 5/2012 | Maksymowych et al. |
| 2012/0171123 A1 | 7/2012 | Medich et al. |
| 2012/0177596 A1 | 7/2012 | Fischkoff et al. |
| 2012/0178107 A1 | 7/2012 | Salfeld et al. |
| 2012/0183997 A1 | 7/2012 | Alley et al. |
| 2012/0190005 A1 | 7/2012 | Schaub et al. |
| 2012/0201831 A1 | 8/2012 | Salfeld et al. |
| 2012/0213792 A1 | 8/2012 | Salfeld et al. |
| 2012/0219564 A1 | 8/2012 | Salfeld et al. |
| 2012/0238730 A1 | 9/2012 | Dong et al. |
| 2012/0244168 A1 | 9/2012 | Salfeld et al. |
| 2012/0251550 A1 | 10/2012 | Borhani et al. |
| 2012/0258114 A1 | 10/2012 | Salfeld et al. |
| 2012/0263731 A1 | 10/2012 | Fraunhofer et al. |
| 2012/0264920 A1 | 10/2012 | Wang et al. |
| 2012/0277165 A1 | 11/2012 | Collins et al. |
| 2012/0282262 A1 | 11/2012 | Okun et al. |
| 2012/0282270 A1 | 11/2012 | Krause et al. |
| 2012/0288494 A1 | 11/2012 | Borhani et al. |
| 2012/0308514 A1 | 12/2012 | Salfeld et al. |
| 2013/0004507 A1 | 1/2013 | Fischkoff et al. |
| 2013/0028903 A1 | 1/2013 | Wan et al. |
| 2013/0065219 A1 | 3/2013 | Tsang et al. |
| 2013/0084605 A1 | 4/2013 | Zhou et al. |
| 2013/0096283 A1 | 4/2013 | Khetan et al. |
| 2013/0115224 A1 | 5/2013 | Salfeld et al. |
| 2013/0122011 A1 | 5/2013 | Hoffman et al. |
| 2013/0122018 A1 | 5/2013 | Salfeld et al. |
| 2013/0156760 A1 | 6/2013 | Fraunhofer et al. |
| 2013/0195888 A1 | 8/2013 | Wang et al. |
| 2013/0205604 A1 | 8/2013 | Esenwein et al. |
| 2013/0243786 A1 | 9/2013 | Banerjee et al. |
| 2013/0273059 A1 | 10/2013 | Wan et al. |
| 2013/0280267 A1 | 10/2013 | Wan et al. |
| 2013/0280274 A1 | 10/2013 | Subramanian et al. |
| 2013/0309242 A1 | 11/2013 | Wan et al. |
| 2013/0323261 A1 | 12/2013 | Wan et al. |
| 2013/0330356 A1 | 12/2013 | Salfeld et al. |
| 2013/0330357 A1 | 12/2013 | Salfeld et al. |
| 2013/0336957 A1 | 12/2013 | Wang et al. |
| 2013/0338344 A1 | 12/2013 | Ramasubramanyan et al. |
| 2013/0344084 A1 | 12/2013 | Subramanian et al. |
| 2014/0010820 A1 | 1/2014 | Wang et al. |
| 2014/0065710 A1 | 3/2014 | Rives et al. |
| 2014/0072585 A1 | 3/2014 | Herigstad et al. |
| 2014/0120583 A1 | 5/2014 | Prentice |
| 2014/0134674 A1 | 5/2014 | Pla et al. |
| 2014/0134675 A1 | 5/2014 | Pla et al. |

(56) References Cited

U.S. PATENT DOCUMENTS

| | | |
|---|---|---|
| 2014/0141007 A1 | 5/2014 | Fraunhofer et al. |
| 2014/0141008 A1 | 5/2014 | Fraunhofer et al. |
| 2014/0142286 A1 | 5/2014 | Prentice |
| 2014/0154270 A1 | 6/2014 | Wang et al. |
| 2014/0178984 A1 | 6/2014 | Jerums et al. |
| 2014/0206038 A1 | 7/2014 | Pla et al. |
| 2014/0234905 A1 | 8/2014 | Pla et al. |
| 2014/0255423 A1 | 9/2014 | Hickman et al. |
| 2014/0271623 A1 | 9/2014 | Parren et al. |
| 2014/0271626 A1 | 9/2014 | Chumsae et al. |
| 2014/0271632 A1 | 9/2014 | Hossler et al. |
| 2014/0271633 A1 | 9/2014 | Hossler |
| 2014/0275494 A1 | 9/2014 | Wang et al. |
| 2014/0288278 A1* | 9/2014 | Nti-gyabaah et al. ... 530/388.24 |
| 2014/0301977 A1 | 10/2014 | Nadarajah et al. |
| 2014/0314745 A1 | 10/2014 | Rives et al. |
| 2014/0377275 A1 | 12/2014 | Neu et al. |
| 2015/0023977 A1 | 1/2015 | Fraunhofer et al. |
| 2015/0110775 A1 | 4/2015 | Subramanian et al. |
| 2015/0110799 A1 | 4/2015 | Ramasubramanyan et al. |
| 2015/0132320 A1 | 5/2015 | Chumsae et al. |
| 2015/0132801 A1 | 5/2015 | Ramasubramanyan et al. |
| 2015/0140006 A1 | 5/2015 | Ramasubramanyan et al. |
| 2015/0141632 A1 | 5/2015 | Markosyan |
| 2015/0158944 A1 | 6/2015 | Bengea et al. |
| 2015/0166650 A1 | 6/2015 | Ramasubramanyan et al. |
| 2015/0166653 A1 | 6/2015 | Wang et al. |
| 2015/0183865 A1 | 7/2015 | Rives et al. |
| 2015/0183866 A1 | 7/2015 | Rives et al. |

FOREIGN PATENT DOCUMENTS

| | | |
|---|---|---|
| DE | 3631229 A1 | 3/1988 |
| EP | 0101681 A1 | 3/1984 |
| EP | 0173177 A1 | 3/1986 |
| EP | 0186833 A2 | 7/1986 |
| EP | 0212489 A2 | 3/1987 |
| EP | 0351789 A2 | 1/1990 |
| EP | 0366043 A1 | 5/1990 |
| EP | 0460426 B1 | 12/1991 |
| EP | 0481791 A2 | 4/1992 |
| EP | 0492448 A1 | 7/1992 |
| EP | 0523949 A1 | 1/1993 |
| EP | 0612251 A1 | 8/1994 |
| EP | 0614984 A2 | 9/1994 |
| EP | 0659766 A1 | 6/1995 |
| EP | 0746398 A1 | 12/1996 |
| EP | 0764719 A2 | 3/1997 |
| EP | 0956873 A2 | 11/1999 |
| EP | 0956875 A2 | 11/1999 |
| EP | 1075488 A1 | 2/2001 |
| EP | 1174148 A1 | 1/2002 |
| EP | 1221476 A2 | 7/2002 |
| EP | 1254666 A1 | 11/2002 |
| EP | 1308455 A2 | 5/2003 |
| EP | 1308456 A2 | 5/2003 |
| EP | 1418967 A2 | 5/2004 |
| EP | 1568388 A1 | 8/2005 |
| EP | 1745141 A1 | 1/2007 |
| EP | 1851305 A1 | 11/2007 |
| EP | 2080809 A1 | 7/2009 |
| EP | 2144929 A1 | 1/2010 |
| EP | 2152856 A1 | 2/2010 |
| EP | 2213726 A1 | 8/2010 |
| EP | 2357250 A2 | 8/2011 |
| EP | 2495307 A1 | 9/2012 |
| EP | 2528002 A2 | 11/2012 |
| EP | 2574677 A1 | 4/2013 |
| GB | 2160530 A | 12/1985 |
| GB | 2279077 A | 12/1994 |
| IN | 2285/MUM/2013 A1 | 1/2015 |
| JP | 7289288 A | 11/1995 |
| WO | WO-87/00195 A1 | 1/1987 |
| WO | WO-90/03430 A1 | 4/1990 |
| WO | WO-90/05144 A1 | 5/1990 |
| WO | WO-91/02078 A1 | 2/1991 |
| WO | WO-91/09967 A1 | 7/1991 |
| WO | WO-92/01047 A1 | 1/1992 |
| WO | WO-92/11383 A1 | 7/1992 |
| WO | WO-92/16553 A1 | 10/1992 |
| WO | WO-93/06213 A1 | 4/1993 |
| WO | WO-94/02602 A1 | 2/1994 |
| WO | WO-94/08619 A1 | 4/1994 |
| WO | WO-94/25585 A1 | 11/1994 |
| WO | WO-94/26910 A1 | 11/1994 |
| WO | WO-94/29347 A1 | 12/1994 |
| WO | WO-9511317 A1 | 4/1995 |
| WO | WO-95/23813 A1 | 9/1995 |
| WO | WO-96/33208 A1 | 10/1996 |
| WO | WO-96/33735 A1 | 10/1996 |
| WO | WO-96/34096 A1 | 10/1996 |
| WO | WO-9704801 A1 | 2/1997 |
| WO | WO-97/13852 A1 | 4/1997 |
| WO | WO-97/29131 A1 | 8/1997 |
| WO | WO-98/23645 A1 | 6/1998 |
| WO | WO-98-23645 A1 | 6/1998 |
| WO | WO-98/24883 A2 | 6/1998 |
| WO | WO-98/24884 A1 | 6/1998 |
| WO | WO-98/24893 A2 | 6/1998 |
| WO | WO-9823645 A1 | 6/1998 |
| WO | WO-98/50433 A2 | 11/1998 |
| WO | WO-9856418 A1 | 12/1998 |
| WO | WO-99/32605 A1 | 7/1999 |
| WO | WO-99/57134 A1 | 11/1999 |
| WO | WO-9957246 A1 | 11/1999 |
| WO | WO-0003000 A2 | 1/2000 |
| WO | WO-01-44442 A1 | 6/2001 |
| WO | WO-0147554 A1 | 7/2001 |
| WO | WO-01-59069 A1 | 8/2001 |
| WO | WO-0177362 A1 | 10/2001 |
| WO | WO-02/12502 A2 | 2/2002 |
| WO | WO-0212501 A2 | 2/2002 |
| WO | WO-03045995 A2 | 6/2003 |
| WO | WO-03/059935 A2 | 7/2003 |
| WO | WO-03/066662 A2 | 8/2003 |
| WO | WO-2004008100 A2 | 1/2004 |
| WO | WO-2004/058944 A2 | 7/2004 |
| WO | WO-2004058800 A2 | 7/2004 |
| WO | WO-2004/097006 A1 | 11/2004 |
| WO | WO-2005042569 A1 | 5/2005 |
| WO | WO-2005-062967 A2 | 7/2005 |
| WO | WO-2005/082483 A1 | 9/2005 |
| WO | WO-2006/043895 A1 | 4/2006 |
| WO | WO-2006045438 A1 | 5/2006 |
| WO | WO-2006/099308 A2 | 9/2006 |
| WO | WO-2006/110277 A1 | 10/2006 |
| WO | WO-2007/087384 A2 | 8/2007 |
| WO | WO-2007/117490 A2 | 10/2007 |
| WO | WO-2008/033517 A2 | 3/2008 |
| WO | WO-2008-057240 A2 | 5/2008 |
| WO | WO-2008068879 A1 | 6/2008 |
| WO | WO-2008087184 A2 | 7/2008 |
| WO | WO-2008121616 A2 | 10/2008 |
| WO | WO-2008135498 A2 | 11/2008 |
| WO | WO-2009/017491 A1 | 2/2009 |
| WO | WO-2009023562 A2 | 2/2009 |
| WO | WO-2009/027041 A1 | 3/2009 |
| WO | WO-2009058769 A1 | 5/2009 |
| WO | WO-2009/073569 A2 | 6/2009 |
| WO | WO-2009135656 A1 | 11/2009 |
| WO | WO-2010/036443 A1 | 4/2010 |
| WO | WO-2010/043703 A1 | 4/2010 |
| WO | WO-2010/122460 A1 | 10/2010 |
| WO | WO-2010/129469 A1 | 11/2010 |
| WO | WO-2010127069 A1 | 11/2010 |
| WO | WO-2011005773 A2 | 1/2011 |
| WO | WO-2011009623 A1 | 1/2011 |
| WO | WO-2011-019619 A1 | 2/2011 |
| WO | WO-2011015926 A1 | 2/2011 |
| WO | WO-2011024025 A1 | 3/2011 |
| WO | WO-2011044180 A1 | 4/2011 |
| WO | WO-2011/073235 A1 | 6/2011 |
| WO | WO-2011069056 A2 | 6/2011 |

(56) References Cited

FOREIGN PATENT DOCUMENTS

| WO | WO-2011098526 A1 | 8/2011 |
|---|---|---|
| WO | WO-2011110598 A1 | 9/2011 |
| WO | WO-2011/133886 A2 | 10/2011 |
| WO | WO-2011127322 A1 | 10/2011 |
| WO | WO-2011134919 A2 | 11/2011 |
| WO | WO-2011134920 A1 | 11/2011 |
| WO | WO-2012019160 A1 | 2/2012 |
| WO | WO-2012030512 A1 | 3/2012 |
| WO | WO-2012050175 A1 | 4/2012 |
| WO | WO-2012051147 A1 | 4/2012 |
| WO | WO-2012/065072 A2 | 5/2012 |
| WO | WO-2012062810 A2 | 5/2012 |
| WO | WO-2012120500 A2 | 9/2012 |
| WO | WO-2012140138 A1 | 10/2012 |
| WO | WO-2012145682 A1 | 10/2012 |
| WO | WO-2012/149197 A2 | 11/2012 |
| WO | WO-2012147048 A2 | 11/2012 |
| WO | WO-2012147053 A1 | 11/2012 |
| WO | WO-2012158551 A1 | 11/2012 |
| WO | WO-2013/011076 A2 | 1/2013 |
| WO | WO-2013006461 A1 | 1/2013 |
| WO | WO-2013006479 A2 | 1/2013 |
| WO | WO-2013009648 A2 | 1/2013 |
| WO | WO-2013013013 A2 | 1/2013 |
| WO | WO-2013-158273 A1 | 10/2013 |
| WO | WO-2013-158279 A1 | 10/2013 |
| WO | WO-2013158275 A1 | 10/2013 |
| WO | WO-2013-164837 A1 | 11/2013 |
| WO | WO-2013-176754 A1 | 11/2013 |
| WO | WO-2013-177115 A2 | 11/2013 |
| WO | WO-2013-177118 A2 | 11/2013 |
| WO | WO-2013-181585 A2 | 12/2013 |
| WO | WO-2013-186230 A1 | 12/2013 |
| WO | WO-2014/039903 A2 | 3/2014 |
| WO | WO-2014/099636 A1 | 6/2014 |
| WO | WO-2014/207763 A1 | 12/2014 |
| WO | WO-2015/004679 A1 | 1/2015 |
| WO | WO-2015/007912 A1 | 1/2015 |

OTHER PUBLICATIONS

U.S. Appl. No. 14/506,576.
U.S. Appl. No. 14/473,775.
U.S. Appl. No. 14/195,588.
U.S. Appl. No. 14/226,333.
U.S. Appl. No. 14/226,579.
U.S. Appl. No. 14/194,305.
U.S. Appl. No. 14/209,999.
U.S. Appl. No. 14/206,296.
U.S. Appl. No. 14/209,821.
U.S. Appl. No. 14/226,636.
Abbott Laboratories Press Release, "Abbott Laboratories Receives FDA Approval Earlier Than Expected for Humira (adalimumab) for the Treatment of Rheumatoid Arthritis," Dec. 31, 2002, pp. 1-4.
Anonymous, "SACHEM Displacement Chromatography," Aug. 29, 2012, Retrieved from the internet: www.displacementchromatography.com, retrieved on Jul. 30, 2014, pp. 1-12.
Averginos, Gab '04 Abstracts—GE Healthcare Life Sciences, "Humira manufacturing: challenges and the path taken", France, Oct. 3-5, 2004, published 2005, pp. 14-16.
Barnes et al., "Stability of Protein Production from Recombinant Mammalian Cells," Biotechnology and Bioengineering, 81:6, Mar. 20, 2003, pp. 631-639.
Byun, et al. Archives of Biochemistry and Biophysics, "Transport of anti-IL-6 binding fragments into cartilage and the effects of injury," 532 (2013), pp. 15-22.
Canghai, Lu et al.: "A T-flask based screening platform for evaluating and identifying plant hydrolysates for a fed-batch cell culture process", Cytotechnology, Kluwer Academic Publishers, DO, vol. 55, No. 1, Aug. 18, 2007, pp. 15-29.
Chumsae, Chris et al.: "Arginine modifications by methylglyoxal: discovery in a recombinant monoclonal antibody and contribution to acidic species.", Analytical Chemistry Dec. 3, 2013, vol. 85, No. 23, Dec. 3, 2013, pp. 11401-11409.
Clincke, M. et al., "Effect of surfactant pluronic F-68 on CHO cell growth, metabolism, production, and glycosylation of human recombinant IFN-γ in mild operating conditions," Biotechnol. Prog. 27(1): 181-190, 2011.
Du et al., "Chromatographic analysis of the acidic and basic species of recombinant monoclonal antibodies" MAbs, Sep.-Oct. 2012; 4(5):578-85.
Feng et al., "Cell Culture Processes for Monoclonal Antibody Production," mAbs, 2:5, 466-477, Sep./Oct. 2010.
Folk et al., "Carboxypeptidase B, Purification and Characterization of the Porcine Enzyme," J. Biological Chem, 1960, 235:2272-2277.
Gramer M Jet al: "Modulation of Antibody Galactosylation Through Feeding of Uridine, Manganese Chloride, and Galactose",Biotechnology and Bioengineering, Wiley & Sons, Hoboken, NJ, US, vol. 108, No. 7, Jul. 1, 2011, pp. 1591-1682.
Gu, X. et al: "Improvement of interferon-gamma sialylation in Chinese hamster ovary cell culture by feeding of N-acetylmannosamine",Biotechnology and Bioengineering, Wiley & Sons, Hoboken, NJ, US, vol. 58, No. 6, Jun. 20, 1998, pp. 642-648.
Hossler et al.; "Improvement of mammalian cell culture performance through surfactant enabled concentrated feed media"; Biotechnology Progress; 29(4):1023-1033 (2013).
Hossler P. et al., "Improvement of mammalian cell culture performance through surfactant enabled concentrated feed media," Biotechnol. Prog. 29(4): 1023-1033, 2013.
Humira (adalimumab) prescribing information, Dec. 20, 2002, pp. 1-16.
ICH Topic Q6B "Specifications:Test Procedures and Acceptance Criteria for Biotechnological/Biological Products," Sep. 1999, pp. 1-17.
International Search Report and Written Opinion from PCT/US2013/065749 dated Mar. 18, 2014, pp. 1-18.
International Search Report and Written Opinion from PCT/US2014/024151 dated Aug. 7, 2014, pp. 1-16.
International Search Report from PCT/US2014/024256 dated Jul. 30, 2014, pp. 1-15.
Invitation to Pay Additional Fees for International Application No. PCT/US2013/065749, Dated May 27, 2014, pp. 1-8.
Invitation to Pay Additional Fees for International Application No. PCT/US2014/026606, Dated Jul. 8, 2014, pp. 1-8.
Jayme et al.; "Media formulation options and manufacturing process controls to safeguard against introduction of animal origin contaminants in animal cell culture"; Cytotechnology; 33:27-36 (2000).
Luo, Ying et al.: "Development toward rapid and efficient screening for high performance hydrolysate lots in a recombinant monoclonal antibody manufacturing process.", Biotechnology Progress Jul. 2012, vol. 28, No. 4, Jul. 2012, pp. 1061-1068.
Martinelle, K. et al., Cells and Culture, Proceedings of the 20th ESACT Meeting v4 819-822, Jun. 17-20, 2007.
McAtee et al., "Isolation of monoclonal antibody charge variants by displacement chromatography," Current Protocols in Protein Science.
Patel, T. P. et al.: "Different culture methods lead to differences in glycosylation of a murine IgG monoclonal antibody", Biochemical journal, The Biochemical Society, London, GB, vol. 285, No. 3, Jan. 1, 1992, pp. 839-845.
Pink, T. et al.: "Regulation of S-layer protein synthesis of bacillus stearothermophilus PV72 through variation of continuous cultivation conditions", Journal of Biotechnology, Elsevier Science Publishers, Amsterdam, NL, vol. 50, No. 2, Oct. 1, 1996, pp. 189-200.
Rea, J. C. et al.: "Validation of a pH gradient-based ion-exchange chromatography method for high-resolution monoclonal antibody charge variant separations", Journal of Pharmaceutical and Biomedical Analysis, New York, NY, US, vol. 54, No. 2, Jan. 25, 2011, pp. 317-323.
Routier, F. H. et al.: "The glycosylation pattern of a humanized IgGI antibody(D1.3) expressed in CHO cells", Glycoconjugate Journal, Chapman & Hall, GB, vol. 14, No. 2, Jan. 1, 1997, pp. 201-207.
Sakai et al.; "Use of nonionic surfactants for effective supply of phosphatidic acid in serum-free culture of Chinese hamster ovary cells"; Journal of Bioscience and Bioengineering; 92(3):256-261 (2001).

(56) References Cited

OTHER PUBLICATIONS

Satoh, Mitsuo et al.: "Non-Fucosylated therapeutic antibodies as next-generation therapeutic antibodies", Expert opinion on biological therapy, Ashley, London, GB, vol. 6, No. 11, Nov. 1, 2006, pp. 1161-1173.
Sundaram et al., "An innovative approach for the characterization of the isoforms of a monoclonal antibody product," Mabs, 3(6):505-512, 2011.
Sung, Hyun Kim et al.: "Development of serum-free medium supplemented with hydrolysates for the production of therapeutic antibodies in CHO cell cultures using design of experiments", Applied Microbiology and Biotechnology, Springer, Berlin, DE, vol. 83, No. 4, Mar. 6, 2009, pp. 639-648.
Tharmalingam et al.; "Pluronic Enhances the Robustness and Reduces the Cell Attachment of Mammalian Cells"; Molecular Biotechnology; 39(2):167-177 (2008).
Wolff et al., "The Kinetics of Carboxypeptidase B Activity," J. Biological Chem, 1962, 237:3094-3099.
Wong N.S.C. et al: "An investigation of intracellular glycosylation activities in CHO cells: Effects of nucleotide sugar precursor feeding" Biotechnology and Bioengineering, vol. 187, No. 2, Oct. 1, 2010, pp. 321-336.
Worthington Biochemical Corporation, porcine pancreas carboxypeptidase B, one page, Feb. 25, 2012.
Ahmed, M. U. et al.; N-(Carboxyethyl)lysine, a product of the chemical modification of proteins by methylglyoxal, increases with age in human lens proteins; Biochem. J. 1997, 324, 565-570.
Ahmed, N. & Thornalley, P. J.; Peptide Mapping of Human Serum Albumin Modified Minimally by Methylglyoxal in Vitro and in Vivo; Ann. N.Y. Acad. Sci. 2005, 1043,260-266.
Ahmed, N. et al.; Peptide Mapping Identifies Hotspot Site of Modification in Human Serum Albumin by Methylglyoxal Involved in Ligand Binding and Esterase Activity; J. Biol. Chem. 2005, 280, 5724-5732.
Ahmed, N.; Thornalley, P. J.; Advanced glycation endproducts: what is their relevance to diabetic complications?; Diabetes, Obes. Metab. 2007, 9, 233-245.
Alfaro, J. F.; Chemo-Enzymatic Detection of Protein Isoaspartate Using Protein Isoaspartate Methyltransferase and Hydrazine Trapping; Anal. Chem. 2008, 80, 3882-3889.
Alfaro, J. F.; Synthesis of LuxS Inhibitors Targeting Bacterial Cell-Cell Communication; Org. Lett. 2004, 6, 3043-3046.
Andersen DC, Goochee CF. The effect of cell-culture conditions on the oligosaccharide structures of secreted glycoproteins. Curr Opin Biotechnol. Oct. 1994;5(5):546-9.
Awdeh, Z.L., A.R. Williamson, and B.A. Askonas, One cell-one immunoglobulin. Origin of limited heterogeneity of myeloma proteins. Biochem J, 1970. 116(2): p. 241-8.
BD Bioscience Product Description for BBL Phytone Peptone (Advanced Processing, Third Edition) (Sep. 23, 2010) (www.bdbiosciences.com/external_files/Doc_Recon_2.0/ab/others/Phytone_Soytone.pdf <http://www.bdbiosciences.com/external_files/Doc_Recon_2.0/ab/others/Phytone_Soytone.pdf>), (last accessed Jan. 8, 2015), 4 pages.
Biastoff, S.; et al.; Colorimetric Activity Measurement of a Recombinant Putrescine N-Methyltransferase from Datura stramonium; Planta Med. 2006, 72, 1136.
Burteau et al. (In Vitro Cell Dev Biol—Animal, Jul. / Aug. 2003. 39-291-296).
Chang, T. & Wu, L., Methylglyoxal, oxidative streee, and hypertension, Can. J. Physiol. Pharmacol. 84: 1229-1238 (2006).
Chaplen, F.W.R., et al., Effect of endogenous methylgiyoxal on Chinese hamster ovary celis grown in culture Cytotechnology 1996, vol. 22, Issue 1-3, Abstract and references, 6 pages.
Chaplen, F.W.R., Incidence and potentiai implications of the toxic metabolite methyiglyoxai in cell culture: A review, C\I1otechnology 26: 173-183, 1998.
Chaplen, FWR; A dissertation entitled Analysis of Methylglyoxal Metabolism in Mammalian Cell Culture; Univ. of Wisconsin-Madison 1996, 218 pages.

Chelius, D. et al.; Identification and Characterization of Deamidation Sites in the Conserved Regions of Human Immunoglobulin Gamma Antibodies, Anal. Chem. 2005, 77,6004-6011.
Chumsae, C., et al., Comparison of methionine oxidation in thermal stability and chemically stressed samples of a fully human monoclonal antibody. Journal of Chromatography B, 2007. 850(1-2): p. 285-294.
Chumsae, C., Gaza-Bulseco, G., & Liu, H., Identification and localization of unpaired cysteine residues in monoclonal antibodies by fluorescence labeling and mass spectrometry. Anal Chem, 2009.81(15): p. 6449-57.
Cordoba, A.J., et al., Non-enzymatic hinge region fragmentation of antibodies in solution. Journal of Chromatography B, 2005. 818(2): p. 115-121.
Crowell, C.K., et al., Amino acid and manganese supplementation modulates the glycosylation state of erythropoietin in a CHO culture system. Biotechnology and bioengineering, Feb. 15, 2007; 96(3):538-549.
Dai, S.; An Integrated Proteomic Analysis of Major Isoaspartyl-Containing Proteins in the Urine of Wild Type and Protein LIsoaspartate O-Methyltransferase-Deficient Mice; Anal. Chem. 2013, 85, 2423-2430.
Dobo, A. & Kaltashov, I. A.; Detection of Multiple Protein Conformational Ensembles in Solution via Deconvolution of Charge-State Distributions in ESI MS; Anal. Chem. 2001,73, 4763-4773.
Ellison, Jay W. et al., "The Nucleotide Sequence of a Human Immunoglobulin Cγ1 Gene," Nucleic Acids Research, vol. 10, No. 13 (1982), 9 pages.
Fleisher B., Mechanism of glycosylation in the Golgi apparatus. J Histochem Cytochem, Aug. 1983; 31(8):1033-1040.
Gauthier, M. A.& Klok, H.-A. Arginine-Specific Modification of Proteins with Polyethylene Glycol Biomacromolecules; 2011, 12, 482-493.
Gaza-Bulseco, G., et al., Characterization of the glycosylation state of a recombinant monoclonal antibody using weak cation exchange chromatography and mass spectrometry. J Chromatogr B Analyt Technol Biomed Life Sci, 2008. 862(1-2): p. 155-60. Epub Dec. 8, 2007.
Goochee C.F., The Oligosaccharides of Glycoproteins: Bioprocess Factors Affecting Oligosaccharide Structure and their Effect on Glycoprotein Properties. Nature Biotechnology Dec. 1991 1346-1355.
Gramer, M.J., et al., "Manipulation of Antibody Glycoforms in a High-Yield GS-CHO Process to Meet Comparability Requirements", *Biotechnology and Bioengineering*, vol. 108, No. 7, Jul. 2011, pp. 1591-1602.
Harlow et al., Eds ("Antibodies: A Laboratory Manual" 1988. Cold Spring Harbor Laboratory Press, Chapter 7, pp. 245, 247,and 253).
Harris, R.J., et al., Identification of multiple sources of charge heterogeneity in a recombinant antibody. Journal of Chromatography B: Biomedical Sciences and Applications, 2001. 752(2): p. 233-245.
Harris, Reed J. et al., "Structural Characterization of a Recombinant CD4-IgG Hybrid Molecule," Eur. J. Biochem. 194:611-620 (1990).
Hills, A.E. et al., Metabolic control of recombinant monoclonal antibody N-glycosylation in GS-NS0 cells, Biotechnology and Bioengineering, Oct. 20, 2001; 75(2):239-251.
Hipkiss, A.; Can the beneficial effects of methionine restriction in rats be explained in part by decreased methylglyoxal generation resulting from suppressed carbohydrate metabolism?; Biogerontology 2012, 13, 633-636.
Hossler et al., "Optimal and consistent protein glycosylation in mammalian cell culture", Glycobiology; (2009), 19(9):936-949.
Huang, L., et al., In Vivo Deamidation Characterization of Monoclonal Antibody by LC/MS/MS. Analytical Chemistry, 2005. 77(5): p. 1432-1439.
HyClone™ CDM4CHO Catalog listing (last accessed Nov. 17, 2014).
International Preliminary Report on Patentability for Application No. PCT/US2013/031352 dated Nov. 25, 2014, pp. 1-10.
International Preliminary Report on Patentability for Application No. PCT/US2013/031389, dated Oct. 21, 2014, pp. 1-10.

(56) References Cited

OTHER PUBLICATIONS

International Preliminary Report on Patentability for Application No. PCT/US2013/031485, dated Oct. 21, 2014, pp. 1-8.
International Preliminary Report on Patentability for Application No. PCT/US2013/031681, dated Oct. 21, 2014, pp. 1-8.
International Preliminary Report on Patentability for Application No. PCT/US2013/041954, dated Nov. 25, 2014, pp. 1-14.
International Preliminary Report on Patentability for Application No. PCT/US2013/041958, dated Dec. 4, 2014, pp. 1-2.
International Search Report and Written Opinion for PCT/US2012/035266, dated Feb. 7, 2013 (corresponds to U.S. Appl. No. 13/547,020), 4 pages.
International Search Report for Application No. PCT/US2014/026606, Dated Dec. 8, 2014, 8 pages.
International Search Report for Application No. PCT/US2014/026636, Dated Jul. 29, 2014, 5 pages.
Jack, M.; Wright, D.; The Role of Advanced Glycation Endproducts and Glyoxalase I in Diabetic Peripheral Sensory Neuropathy; Transl. Res. 2012, 159, 355-365.
Jakubowski, H., Protein N-homocysteinylation: implications for atherosclerosis. Biomedicine & amp; Pharmacotherapy, 2001. 55(8): p. 443-447.
Jayapal, Karthik P., et al., "Recombinant Protein Therapeutics from CHO Cells—20 Years and Counting," CHO Consortium, SBE Special Section, 40-47 (2007).
Jefferis, R., Glycosylation of Recombinant Antibody Therapeutics. Biotechnology Progress, 2005.21(1): p. 11-16.
Johnson, K.A., et al., Cation exchange HPLC and mass spectrometry reveal C-terminal amidation of an IqG1 heavy chain. Analytical Biochemistry, 2007. 360(1): p. 75-83.
Kanda, et al.: "Comparison of biological activity among nonfucosylated therapeutic IgG1 antibodies with three different N-linked Fc oligosaccharides: the high-mannose, hybrid, and complex types", Glycobiology, Oxford University Press, US, vol. 17, No. 1, Sep. 2006, pp. 104-118.
Kingkeohoi, S. & Chaplen, F.W.R., Analysis of methylglyoxal metabolism in CHO celis grown in culture, Cytotechnology (2005) 48:1-13.
Kwon et al., "Production of lactic acid by *Lactobacillus rhamnosus* with vitamin-suppremented soybean hydrolysate", Enzyme Microb Technol. (2000), 26:209-215.
Li, Feng, et al., "Cell Culture Processes for Monoclonal Antibody Production," mAbs 2:5, 466-479 (Sep.-Oct. 2010).
Liu, H., et al., Heterogeneity of monoclonal antibodies. Journal of Pharmaceutical Sciences, 2008. 97(7): p. 2426-2447.
Liu, H., Gaza-Bulseco, G., & Lundell, E., Assessment of antibody fragmentation by reversed-phase liquid chromatography and mass spectrometry. J Chromatogr B Analyt Technol Biomed Life Sci, 2008. 876(1): p. 13-23. Epub Oct. 15, 2008.
Liu, M, et al.; Discovery of Undefined Protein Cross-Linking Chemistry: A Comprehensive Methodology Utilizing 18O-Labeling and Mass Spectrometry; Anal. Chem. 2013, 5900-5908.
Liu, M.et al.; Protein Isoaspartate Methyltransferase-Mediated 18O-Labeling of Isoaspartic Acid for Mass Spectrometry Analysis; Anal. Chem. 2011, 84, 1056-1062.
Lo, T.W. et al., Binding and modification of proteins by methyiglyoxai under physioiogical conditions. A kinetic and mechanistic study with N alpha-acetylarginine, N alpha-acetylcysteine, and N alpha-acetyilysine, and bovine serum albumin, Dec. 23, 1994, The Journal of Biological Chemistrv, 269, 32299-32305.
Manning, M., et al., *Stability of Protein Pharmaceuticals: An Update.* Pharmaceutical Research, 2010.27(4): p. 544-575.
Matthews, R. G.; et al.; Cobalamin-Dependent and Cobalamin-Independent Methionine Synthases: Are There Two Solutions to the Same Chemical Problem?; Helv. Chim. Acta 2003, 86, 3939-3954.
Mizuochi, T., et al., Structural and numerical variations of the carbohydrate moiety of immunoglobulin G. J Immunol, 1982. 129(5): p. 2016-20.
Moorhouse, K.G., et al., Validation of an HPLC method for the analysis of the charge heterogeneity of the recombinant monoclonal antibody IDEC-C2B8 after papain digestion. Journal of Pharmaceutical and Biomedical Analysis, 1997. 16(4): p. 593-603.
Mostafa, A et al.; Plasma protein advanced glycation and products, carboxymethyl cysteine, and carboxyethyl cysteine, are elevated and related to nephropathy in patients with diabetes Mol. Cell. Biochem. 2007, 302, 35-42.
Ni, W.; Analysis of Isoaspartic Acid by Selective Proteolysis with Asp-N and Electron Transfer Dissociation Mass Spectrometry; Anal. Chem. 2010, 82,7485-7491.
Ouellette, D.; Studies in serum support rapid formation of disulfide bond between unpaired cysteine residues in the VH domain of an immunoglobulin G1 molecule; Anal. Biochem. 2010, 397, 37.
Oya, T. et al. Methylglyoxal Modification of Protein: Chemical and Immunochemical Characterization of Methylglyoxal-Arginine Adducts. J. Bioi Chem. Jun. 25, 1999; vol. 274, No. 26, pp. 18492-19502.
Pacis, et al.: "Effects of cell culture conditions on antibody N-linked glycosylation—what affect high mannose 5 glycoform", Biotechnology and Bioengineering vol. 108, No. 10 Oct. 2011, pp. 2348-2358.
Paoli, T. et al., A Study of D-Lactate and Extracellular Methylglyoxal Production in Lactate ReUtilizing CHO Cultures, Biotechnology and Bioengineering, vol. 107, No. 1, Sep. 1, 2010, pp. 182-189.
Parekh RB N-glycosylation and the production of recombinant glycoproteins vol. 7, Issue 5, p. 117-122, May 1989 Trends in Biotechnology.
Parekh, R.B., et al., Association of rheumatoid arthritis and primary osteoarthritis with changes in the glycosylation pattern of total serum IgG. Nature, 1985. 316(6027): p. 452-7.
PCT/US2013/069702 International Search Report & Written Opinion mailed Jan. 31, 2014, 13 pages.
Perkins, M.; et. al. Determination of the Origin of Charge Heterogeneity in a Murine Monoclonal Antibody; M. Pharm. Res. 2000, 17, 1110-1117.
Quan, C., et al., A study in glycation of a therapeutic recombinant humanized monoclonal antibody: Where it is, how it got there, and how it affects charge-based behavior. Analytical Biochemistry, 2008. 373(2): p. 179-191.
Rabbani, N.; Thornalley, P. J.; Glyoxalase in diabetes, obesity and related disorders; Semin. Cell Dev. Biol. 2011, 22, 309-317.
Ren, D., et al., Reversed-phase liquid chromatography-mass spectrometry of site-specific chemical modifications in intact immunoglobulin molecules and their fragments. Journal of Chromatography A, 2008. 1179(2): p. 198-204.
Roy, B.M., et al., Toxic concentrations of exogenously supplied methy!glyoxal in hybridoma cell culture, Cytotechnology (2004) 46:97-107.
Saxena, R. K. et al.; Microbial production and applications of 1,2-propanediol; Indian J. Microbiol. 2010,50,2-11.
Shen, Amy Y. et al., "Recombinant DNA Technology and Cell Line Development," from "Cell Culture Technology for Pharmaceutical and Cell-Based Therapies," CRC Press, 1995, 15-40.
Sigma Catalog "RPMI1640" (last accessed Jan. 22, 2015), 3 pages.
Sigma MSDS for RMPI1640 (last accessed Jan. 22, 2015), 6 pages.
TESS database "HYCLONE" Trademark #76244963. Filing date Apr. 23, 2001. Live mark. Last accessed Jan. 21, 2015.
TESS database "HYCLONE" Trademark #85769283. Filing date Sep. 30, 2012. Live mark. Last accessed Jan. 21, 2015.
Van Herreweghe, et al.; Tumor necrosis factor-induced modulation of glyoxalase I activities through phosphorylation by PKA results in cell death and is accompanied by the formation of a specific methylglyoxal-derived AGE; Proc. Natl. Acad. Sci. 2002, 99, 949-954.
Vasilli, P., Annu. Rev. Immunol. 10:411-452 (1992); and Tracey, K. J. and Cerami, A. Annu. Rev. Med. 45:491-503 (1994).
Vlasak, J. & Ionescu, R., *Heterogeneity of Monoclonal Antibodies Revealed by Charge-Sensitive Methods.* Current Pharmaceutical Biotechnology, 2008. 9(6): p. 468-481.
Walsh, et al.: "Post-translational modifications in the context of therapeutic proteins", Nature Biotechnology, vol. 24, No. 10, Oct. 2006, pp. 1241-1252.
Wang, Z.; et al. Desulfurization of Cysteine-Containing Peptides Resulting from Sample Preparation for Protein Characterization by MS; Rapid Commun. Mass Spectrom. 2010, 24, 267-275.

(56) References Cited

OTHER PUBLICATIONS

Watt, S.; et al.; Effect of Protein Stabilization on Charge State Distribution in Positive- and Negative-Ion Electrospray Ionization Mass Spectra; J. Am. Soc. Mass. Spectrom. 2007, 18, 1605-1611.
Williams, A. et al., Ion-Exchange Chromatography, Oct. 1998, Supplement 44, pp. 10-10-1-10-10-30.
Xiang, T., Chumsae, C. & Liu, H., Localization and Quantitation of Free Sulfhydryl in Recombinant Monoclonal Antibodies by Differential Labeling with 12C and 13C Iodoacetic Acid and LC-MS Analysis. Analytical Chemistry, 2009. 81(19): p. 8101-8108.
Yuk, I.H. et al., Controlling Glycation of Recombinant Antibody in Fed Batch Cell Cultures, Nov. 2011, Biotechnology and Bioengineering, vol. 108, No. 11 pp. 2600-2610.
Zang, T.; et al.; Chemical Methods for the Detection of Protein N-Homocysteinylation via Selective Reactions with Aldehydes; Anal. Chem. 2009, 81, 9065-9071.
Zhang, B., et al., Unveiling a Glycation Hot Spot in a Recombinant Humanized Monoclonal Antibody. Analytical Chemistry, 2008. 80(7): p. 2379-2390.
Zhang, T.; Identification and Characterization of Buried Unpaired Cysteines in a Recombinant Monoclonal IgG1 Antibody; Anal. Chem. 2012, 84, 7112-7123.
Zhang, W. and Czupryn, M.J., Free Sulfhydryl in Recombinant Monoclonal Antibodies. Biotechnology Progress, 2002. 18(3): p. 509-513.
Zhao, G.; Chemical Synthesis of S-Ribosyl-L-homocysteine and Activity Assay as a LuxS Substrate; Bioorg. Med. Chem. Lett. 2003,13,3897-3900.
Zhou, Z. et al.; An Antibody-Catalyzed Allylic Sulfoxide-Sulfenate Rearrangement; J. Org. Chem. 1999,64,8334-8341.
Zhou, Z. S. et al. An Antibody-Catalyzed Selenoxide Elimination; J. Am. Chem. Soc. 1997, 119, 3623-3624.
Bandyopadhyay S., et al. Physicochemical and functional characterization of a biosimilar adalimumab ZRC-3197, Biosimilars, 2015;5, pp. 1-18.
Bendtzen, K. et al. "Auto-antibodies to IL-1α and TNFα in Normal Individuals and in Infectious and Immunoinflammatory Disorders" *The Physiological and Pathological Effects of Cytokines*, 447-52 (1990).
Chung et al. "Cetuximab-induced anaphylaxis and IgE specific for galactose-a-1,3-galactose" NEJM 358:11, 1109-1117 (2008).
Dionex Application Note 125 (Monitoring Protein Deamidation by Cation-Exchange Chromatography. 2009; pp. 1-7).
Emery, P. "Adalimumab therapy: Clinical findings and implications for integration into clinical guidelines for rheumatoid arthritis." *Drugs of Today*, 41(3): p. 155-163. (2005).
European Medicines Agency (EMA Europe), "2004 Report on Scientific Discussion for the Approval of Humira™ (adalimumab)," Last accessed Nov. 12, 2014 at www.ema.europa.eu/docs/en_GB/document_library/EPAR_Scientific_Discussion/human/000481/WC500050867.pdf; 25 pages.
Fahrner et al., "Industrial purification of pharmaceutical antibodies: development, operation, and validation of chromatography processes" Biotechnology and Genetic Engineering Reviews, 18, 2001, pp. 301-327.
Gagnon, P., "Polishing methods for monoclonal IgG purification" Chapter 17, Taylor & Francis Group, LLC, pp. 491-505, 2007.
Gao et al. "Site-selective modifications of arginine residues in human hemoglobin induced by methylglyoxal." Biochemistry, 2006; pp. 15654-15660.
Goswami et al., "Developments and Challenges for mAb-Based Therapeutics," *Antibodies*, 2:452-500, 2013.
Harding et al., "Class switching in human immunoglobulin transgenic mice" (1995) *Ann. NY Acad. Sci.*, 764:536-547.
International Preliminary Report on Patentability for Application No. PCT/US2013/031365, dated Mar. 3, 2015, 9 pages.
Kazuaki F et al "Enhancment of productivity of recombinant a-amidating enzyme by low temperature culture" Cytotechnology 31:85-94, 1999.

Leusch, "Failure to demonstrate TNFα-specific autoantibodies in human sera by ELISA and Western blot" (1991) *J. Immunol. Methods*, 139:145-47.
Liu et al. "Recovery and purificaiton process development for monoclonal antibody production" MABS, 2(5), pp. 480-499 (2010).
Mehta, et al. "Purifying therapeutic monoclonal antibodies," Chemical Engineering Progress; May 2008, 104, 5; pp. S14-S20.
Muller-Spath, et al., "Chromatographic Separation of Three Monoclonal Antibody Variants Using Multicolumn Countercurrent Solvent Gradient Purification (MCSGP)" Biotechnology and Bioengineering, vol. 100. No. 6 (2008), pp. 1166-1177.
Rau "Adalimumab (a fully human anti-tumour necrosis factor alpha monoclonal antibody) in the treatment of active rheumatoid arthritis: the initial results of five trials" Ann Rheum Dis 2002,61 (Suppl II): ii70-ii73.
Roe, S. "Separation Based on Structure" Chapter 4, § 5.2, In, Protein Purification Methods; A Practical Approach, Harries, et al. Sep. 1989, p. 203.
Sargent (pp. 1-3, Internet Archive captured Aug. 28, 2013, http://cellculturedish.com/2012/01 /cho-cells-the-top-expressionsystem-of-best-selling-biologic-drugs/).
Shubert et al. "Comparison of ceramic hydroxy- and fluoroapatite versus Protein A/G-based resins in the isiolation of a recombinant human antibody from cell culture supernatant" J. Chromatography A, 114 (2007) 106-113.
The Kennedy Institute of Rheumatology, 1995 Annual Scientific Report, "Anti-TNF trials and studies of mechanisms of action".
United States Food and Drug Administration (FDA) Biological Licensing Application File No. 125057 (Adalimumab) (Dec. 31, 2002) (Last Accessed Mar. 4, 2015 at <http://www.fda.gov/Drugs/DevelopmentApprovalProcess/HowDrugsareDevelopedandApproved/ApprovalApplications/TherapeuticBiologicApplications/ucm080610.htm>), 1 page.
"Genentech unveils production capacity hikes," in-Pharma Technologist.com Jun. 28, 2005, pp. 1-2.
"Memorandum in Support of Centocor's Motion for Summary Judgment No. 1 that All Asserted Claims Are Invalid for Lack of Written Description", dated Aug. 1, 2013 and submitted by defendant in Civil Action No. 09-40089-FDS.
"Memorandum in Support of Centocor's Motion for Summary Judgment No. 2 that All Asserted Claims Are Invalid for Lack of Enablement", dated Aug. 1, 2013 and submitted by defendant in Civil Action No. 09-40089-FDS.
"Memorandum in Support of Centocor's Motion for Summary Judgment No. 4 that Claims Encompassing Non-recombinant Human Antibodies Are Invalid for Failing to Meet the Requirements of 35 U.S.C. § 112", dated Aug. 1, 2013 and submitted by defendant in Civil Action No. 09-40089-FDS.
"Memorandum in Support of Centocor's Motion No. 3 for Summary Judgment that the 394 and 031 Patents Are Invalid for Under 35 U.S.C. § 102(f) for Failing to Name the Proper Inventors", dated Aug. 1, 2013 and submitted by defendant in Civil Action No. 09-40089-FDS.
"Memorandum in Support of Centocor's Motion No. 6 for Summary Judgment that References Dated Before Feb. 10, 1997 Qualify as Prior Art to the 394 and 031 Patents", dated Aug. 1, 2013 and submitted by defendant in Civil Action No. 09-40089-FDS.
"Plaintiffs' Memorandum in Support of Their Motion for Partial Summary Judgment", dated Aug. 1, 2013 and submitted by plaintiff in Civil Action No. 09-40089-FDS.
"Plaintiffs' Rule 56.1 Statement of Undisputed Material Facts in Support of Their Motion for Partial Summary Judgment", dated Aug. 1, 2013 and submitted by plaintiff in Civil Action No. 09-40089-FDS.
Abraham, E., et al., "Efficacy and Safety of Monoclonal Antibody to Human Tumor Necrosis Factor α in Patients with Sepsis Syndrome," *JAMA*, vol. 273(12):934-941 (1995).
Adams. et al. J. Am. Acad. Dermatol 2004;51 :660-2.
Altamirano, C., et al., "Strategies for fed batch cultivation of t-PA producing CHO cells: substitution of glucose and glutamine and rational design of culture medium", *J. Biotechn.* 110:171-179, 2004.
Antes et al. "Analysis of lysine clipping of a humanized Lewis-Y specific IgG antibody and its relation to Fc-mediated effector func-

(56) References Cited

OTHER PUBLICATIONS tion" Journal of Chromatography B:Biomedical Sciences and Applications, Elsevier, Amsterdam, NL, vol. 852, No. 1-2, May 31, 2007, 250-256.
Avgerinos et al. (GAb '04 Abstracts—GE Healthcare Life Sciences, France Oct. 3-5, 2004, pp. 15-16 published 2005).
Azevedo et al., "Integrated Process for the Purification of Antibodies Combining Aqueous Two-Phase Extraction, Hydrophobic Interaction Chromatography and Size-Exclusion Chromatography", *Journal of Chromatography* (2008) 1213(2): 154-161.
Ballez, J.S. et al., "Plant protein hydrolysates support CHO-320 cells proliferation and recombinant IFN-[gamma] production in suspension and inside microcarriers in protein-free media", *Cytotechnology* 44:3, 103-114, 2004.
Barbuto, J. et al. "Production of Neutralizing Antibodies to Tumor Necrosis Factor by Human Tumor-Infiltrating B Lymphocytes" *Proc. Am. Assoc. Cancer Res,.* 34:487, Abstr. 2904 (1993).
Biblia, T.A. et al., "In Pursuit of the Optimal Fed-Batch Process for Monoclonal Antibody Production", Biotechnol. Prog 11(1):1-13, Jan.-Feb. 1995.
Birch, Jr. et al., "Antibody production", Adv. Drug Delivery Reviews 58:671-685, 2006.
Blaker, GJ, et al., "The Glucose, Insulin and Glutamine Requirements of Suspension Cultures of HeLa Cells in a Defined Culture Medium", J. Cell Sci. 9:529-537, 1971.
Boekstegers, P., et al., "Repeated administration of a F(ab')2 fragment of an anti-tumor necrosis factor alpha monoclonal antibody in patients with severe sepsis: effects on the cardiovascular system and cytokine levels," *Shock*, vol. 1(4):237-245 (1994).
Bollati-Fogolin M., et al., "Temperature Reduction in Cultures of hGM-CSF-expressing CHO Cells: Effects on Productivity and Product Quantity", Biotechnol. Prog. 21:17-21, 2005.
Bonafede et al. "Cost per treated patient for etanercept, adalimumab, and infliximab across adult indications: a claims analysis" Advances in Therapy, Springer Healthcare Communications, Heidelberg, vol. 29, No. 3, Mar. 9, 2012, 234-249.
Boyle, P. et al "A Novel Monoclonal Human IgM Autoantibody which Binds Recombinant Human and Mouse Tumor Necrosis Factor-α" *Cell. Immunol.*, 152:556-68 (1993).
Boyle, P. et al. "The B5 Monoclonal Human Autoantibody Binds to Cell Surface TNFα on Human Lymphoid Cells and Cell Lines and Appears to Recognize a Novel Epitope" *Cell. Immunol.*, 152:569-81 (1993).
Brekke, O. et al., "Therapeutic Antibodies for Human Diseases at the Dawn of the Twenty-first Century," *Nature*, vol. 2:52-62 (2002).
Brorson et al., "Bracketed Generic Inactivation of Rodent Retroviruses by Low pH Treatment; for Monoclonal Antibodies and Recombinant Proteins," Biotechnology and Bioengineering,; vol. 82(3): 321-329 (2003).
Bruggemann et al., "Production of human antibody repertoires in transgenic mice" Cur. Op. Biotechnol. *;455-458 (1997).
Bruggemann, M., Neuberger, M.S., "Strategies for expressing human antibody repertoires in transgenic mice," *Immunol. Today* 17:391-397 (1996).
Cai B, et al. "C-Terminal Lysine Processing of Human; Immunoglobulin G2 Heavy Chain In Vivo" Biotechnol. Bioeng. 2011;108: 404-412.
Cambridge Antibody Technology, advertisement of phage display services, Science vol. 253, No. 5018 (1991).
Carter et al., "Humanization of an anti-p185HER2 antibody for human cancer therapy," *Proc. Nat. Acad. Sci*89:4285-4289 (1992).
Chang KH, et al., "N-Acetylcysteine Increases the Biosynthesis of Recombinant EPO in Apoptotic Chinese Hamster Ovary Cells", Free Radic Res. 30(2):85-91, 1999.
Charter, Edward A., "A New Process for the Separation and Purification of Egg Yolk; Antibodies," BASc., The University of British Columbia; A Thesis; Apr. 1993.
Choo et al. "High-level production of a monoclonal antibody in murine myeloma cells by perfusion culture using a gravity settler" Biotechnology Progress, vol. 23, No. 1, Jan. 1, 2007, 225-231.

Chow, A. et al. "Effect of monoclonal antibody on human tumor necrosis factor (TNF MAb) on TNFα, IL-1β, and IL-6 levels in patients with sepsis syndrome" *Clinical Research*, 42:2 299A (1994).
Chua, FKF et al., "Hyper-stimulation of monoclonal antibody production by high osmolarity stress in eRDF medium", J. Biotechnology 37(3):265-275, Nov. 15, 1994.
Chung et al., "Utilization of Lysozyme Charge Ladders to Examine the Effects of Protein Surface; Charqe Distribution on Bindinq Affinity in Ion Exchanqe Systems," Lanqmuir 26(2):759-768 (2010).
Chung et al., "Cetuximab-Induced Anaphylaxis and IgE Specific for Galactose-α-1, 3-Galactose", *N. Engl. J. Med.*, 358:11, pp. 1109-1117 (2008).
Cleland, J. et al., "A Specific Molar Ratio of Stabilizer to Protein is Required for Storage Stability of a Lyophilized Monoclonal Antibody," *Journal of Pharmaceutical Sciences*, vol. 90(3):310-321 (2001).
Cohen, J., et al., "Intersept: An international, multicenter, placebo-controlled trial of monoclonal anitbody to human tumor necrosis factor-α in patients with sepsis," *Crit Care Med*, vol. 24(9):1431-1440 (1996).
Cox, J. et al. "A directory of human germ-line $V_\kappa$ segments reveals a strong bias in their usage" *Eur. J. Immunol.*, 24(2):827-36 (1994).
Cromwell (GAB'04 Abstracts—GE Healthcare Life Sciences, Franc Oct. 3-5, 2004, pp. 17-18 published 2005).
Daugherty, et al. Formulation and Delivery Issues for Monoclonal Antibody Therapeutics. Advanced Drug Delivery Reviews, 2006. vol. 58, pp. 686-706.
Davies et al., "Antibody VH domains as small recognition units." *Biotechnology*, 13:475-479 (1995).
Department of Surgery, University of Toronto, Annual Report (1998-1999)(348 pages).
DePhillips et al., "Determinants of protein retention characteristics on cation-exchange adsorbents,"; Journal of Chromatograph A, 933:57-72 (2001).
deZongotita et al., "Phosphate feeding improves high-cell-concentration NS0 myeloma cell culture performance for monoclonal antibody production" Biotechnology and Bioengineering. 2000, 69: 566-576.
Dick et al: "C-terminal lysine variants in fully human monoclonal antibodies: Investigation of test methods; and possible causes", Biotechnology and Bioengineering, vol. 100, No. 6, Aug. 15, 2008, pp. 1132-1143.
Dolezal, et al., "*Escherichia coli* Expression of a Bifunctional Fab-peptide Epitope Reagent for the Rapid Diagnosis of HIV-1 and HIV-2", *Immunotechnology*, 1:197-209 (1995).
Doring, E., "Identification and Characterization of a TNFa Antagonist Derived from a Monoclonal Antibody" (1994) *Mol. Immunol* .31(14): 1059-1067.
Elliot et al., "Repeated therapy with monoclonal antibody to tumour necrosis factor α (cA2) in patients with rheumatoid arthritis" (1994) *Lancet*, 344:1125-1127.
Elliot, "Treatment of rheumatoid arthritis with chimeric monoclonal antibodies to tumor necrosis factor α" (1993) *Arthritis & Rheumatism*, 36(12):1681-1690.
Emery, P. "Adalimumab therapy: Clinical findings and implications for integration into clinical guidelines for rheumatoid arthritis." *Drugs of Today*, 41(3): p. 155-153. (2005).
Erbitux (cetuximab) label, Revised Aug. 2013.
Ewert et al., "Biophysical Properties of Human Antibody Variable Domains," J. Mol. Biol. 324: 531-; 553 (2003).
Exhibit dated Aug. 1, 2013 and cited by defendant in Civil Action No. 09-40089-FDS providing the Jun. 23, 2009 trial transcript of the PM session in the matter of *Centocor, et al.* v. *Abbott Laboratories*.
Exhibit dated Aug. 1, 2013 and cited by defendant in Civil Action No. 09-40089-FDS providing the trial transcript in the matter of *Abbott Laboratories, et al.* v. *The Mathilda and Terrance Kennedy Institute*, S.D.N.Y.
Exhibit dated Aug. 1, 2013 and cited by plaintiff in Civil Action No. 09-40089-FDS providing excerpts from the File History of U.S. Appl. No. 12/578,487.

(56) References Cited

OTHER PUBLICATIONS

Exhibit dated Aug. 1, 2013 and cited by defendant in Civil Action No. 09-40089-FDS providing the Jun. 24, 2009 trial transcript of the AM session in the matter of *Centocor, et al.* v. *Abbott Laboratories*, E.D. TX.
Exhibit dated Aug. 1, 2013 and cited by defendant in Civil Action No. 09-40089-FDS providing the Sep. 20, 2012 Day 8 trial transcript in the matter of *Abbott* v. *Centocor Ortho Biotech Inc.*, D. MA.
Exhibit dated Aug. 1, 2013 and cited by plaintiff in Civil Action No. 09-40089-FDS providing Declaration by Jochen Salfeld, dated Jan. 17, 2013.
FDA Package insert for Adalimumab, Sep. 26, 2003, pp. 1-18.
Feldmann, "Anti-TNF-alpha Therapy of Rheumatoid Arthritis: What Have We Learned?" (2001) *Annu. Rev. Immunol.*, 19:163-196.
Figini, "In Vitro assembly of Repertoires of Antibody Chains on the Surface of Phage by Renaturation" (1994) *J. Mol. Biol.*, 239:68-78.
Fishwild et al., "High-avidity human IgG kappa monoclonal antibodies from a novel strain of minilocus transgenic mice" (1996) *Nature Biotechnology*, 14:845-851.
Fomsgaard, "Auto-antibodies to Tumor Necrosis Factor α in Healthy Humans and Patients with Inflammatory Diseases and Gram-Negative Bacterial Infections" (1989) *Scand. J. Immunol.* 30:219-23.
Foote, J., "Antibody framework residues affecting the conformation of the hypervariable loops" (1992) *J. Mol .Biol.*, 224(2):487-499.
Freitag et al., "Displacement chromatography in biotechnological downstream processing," J. Chromatography, (1995) 691(1):101-112.
Gagnon et al., "A Systematic Approach to the Purification of Monoclonal Antibodies," *LC-GC* 11 (1):26-34 (1993).
Gatto, B. "Biologics targeted at TNF: design, production and challenges", Reumatismo 58(2):94-103, 2006.
Genbank Entry for CHO Cathepsin L., EGW13555, Aug. 25, 2011, pp. 1-2.
Ghaderi, et al., "Implications of the Presence of N-glycolylneuraminic acid in Recombinant Therapeutic Glycoproteins", *Nature Biotechnology*, 28(8):863-868 (2010).
Ghaderi, et al., "Production platforms for biotherapeutic glycoproteins. Occurrence, impact, and challenges of non-human sialylation", *Biotechnology and Genetic Engineering Reviews*, 28:147-176 (2012).
Gonzalez et al. "Purification of Lactic Acid from Fermentation Broths by Ion-Exchange Resins" Ind. Eng. Chem. Res. 45:3243 (2006).
Graf et al., "Ion exchange resins for the purification of monoclonal antibodies from animal cell culture" Bioseparation 4 (1) :7-20 (Feb. 1994). ;4 (1) :7-20 (Feb. 1994).
Gram et al., "In vitro selection and affinity maturation of antibodies from a naive combinatorial immunoglobulin library" (1992) *PNAS*, 89:3576-3580.
Gramer et al., "Glycosidase Activities of the 293 and NS0 Cell Lines, and of an Antibody-Producing Hybridoma Cell Line", *Biotechnology and Bioengineering*, 43:423-428 (1994).
Green et al., "Antigen-specific human monoclonal antibodies from mice engineered with human Ig heavy and light chain YACs" (1994) *Nature Genetics*, 7:13-21.
Griffiths et al., "Isolation of high affinity human antibodies directly from large synthetic repertoires" (1994) *EMBO J.*, 13:3245-3260.
Griffiths, "Human anti-self antibodies with high specificity from phage display libraries" (1993) *The EMBO J.* 12(2):725-34.
Grunberg, J. et al., "High-Yield Production of Recombinant Antibody Fragments in HEK-293 Cells Using Sodium Butyrate", BioTechniques 34(5):968-972, May 2003.
Han, Kyu Oh et al., "Effect of N-Acetylcystein on Butyrate-Treated Chinese Hamster Ovary Cells to Improve the Production of Recombinant Human Interferon-β-1a", Biotechnol. Prog. 21(4):1154-1164, 2005.
Harlow and Lane, Antibodies A Laboratory Manual, Purification of Antibodies by using a; Deae-matrix (Batch), Storing and Purifying Antibodies; Chapter 8: 302-303 (1988).
Harris et al. "Processing of C-terminal lysine and argnine residues of proteins isolated from mammalian cell culture" Journal of Chromatography, (1995) 705; 129-123.
Harrison et al., "Protein N-Glycosylation in the Baculovirus-Insect Cell Expression System and; Engineering of Insect Cells to Produce "Mammalianized" Recombinant Glycoproteins," Advances in; Virus Research, 68:159-191 (2006).
Hawkins, "Selection of Phage Antibodies by Binding Affinity Mimicking Affinity Maturation" (1992) *J. Mol. Biol.*, 226:889-896.
Heidemann, R. et al., "The use of peptones as medium additives for the production of a recombinant therapeutic protein in high density perfusion cultures of mammalian cells", Cytotechnology 32:157-167, 2000.
Helms et al., "Destabilizing loop swaps in the CDRs of an immunoglobulin VL domain," Protein; Science 4:2073-2081 (1995).
Hiatt et al., "Characterization and Applications of Antibodies Produced in Plants", *Intern. Rev. Immunol.*, 10:139-152 (1993).
Hiatt et al., "Production of Antibodies in Transgenic Plants", *Nature*, 342:76-78 (1989).
Hillgren, A. et al., "Protection mechanism of Tween 80 during freeze-thawing of a model protein LDH," *International Journal of Pharmaceutics*, vol. 237:57-69 (2002).
Hokke et al., "Sialylated Carbohydrate Chains of Recombinant Human Glycoproteins Expressed in Chinese Hamster Ovary Cells Contain Traces of N-glycolylneuraminic acid", *FEBS*, 275:9-14 (1990).
Holler, "Modulation of Acute Graft-Versus-Host Disease After Allogeneic Bone Marrow Transplantation by Tumor Necrosis Factor-alpha (TNF-alpha) Release in the Course of Pretransplant Conditioning: Role of Conditioning Regimens and Prophylactic Application of a Monoclonal Antibody Neutralizing Human TNF-alpha (MAK 195F)" (1995) *Blood*, 86(3):890-899.
Holt, L. et al., "Domain antibodies: proteins for therapy," Trends in Biotechnology, vol. 21(11):484-490 (2003).
Hoogenboom et al., "By-passing immunisation : Human antibodies from synthetic repertoires of germline VH gene segments rearranged in vitro" (1992) *J. Mol. Biol.*, 227:381-388.
Hoogenboom, "Converting rodent into human antibodies by guided selection" (1996) *Antibody Engineering*, Oxford University Press, pp. 169-185.
Horvath et al: "Characterization of a Monoclonal Antibody Cell Culture Production Process Using a Quality by; Design Approach", Molecular Biotechnology, vol. 45, No. 3, Jul. 1, 2010, pp. 203-206.
http://www.cygnustechnologies.com/product_detail/host-cell-protein-antibodies/anti-cho-h . . . Cygnus Technologies, Anti-CHO HCP (Apr. 18, 2012).
Huang et al. "Effects of anti-TNF monoclonal antibody infusion in patients with hairy cell leukaemia" (1992) *Br. J. Haematol.*, 81(2):231-234.
Hui et al., "Recovery and purification process development for monoclonal antibody production," MABS (2010) 2(5):480-499.
Humira (adalimumab) label, Revised Sep. 2013.
Huse, "Generation of a large combinatorial library of the immunoglobulin repertoire in phage lambda" (1989) *Science*, 246:1275-81.
International Preliminary Report on Patentability for Application No. PCT/US07/08359, dated Dec. 12, 2011.
International Preliminary Report on Patentability for Application No. PCT/US2011/060388, dated May 30, 2012.
International Search Report and Written Opinion for Application No. PCT/US2008/085066, dated May 12, 2009.
International Search Report and Written Opinion for Application No. PCT/US2010/033387, dated Aug. 7, 2012.
International Search Report and Written Opinion for Application No. PCT/US2013/031380, dated Feb. 5, 2014.
International Search Report and Written Opinion for Application No. PCT/US2013/041954, dated Dec. 17, 2013.
International Search Report and Written Opinion for Application No. PCT/US2013/041958, dated Dec. 17, 2013.
International Search Report and Written Opinion for Application No. PCT/US2013/065720, dated Dec. 16, 2013.
International Search Report and Written Opinion for Application No. PCT/US2013/065797, dated Nov. 26, 2013.

(56) References Cited

OTHER PUBLICATIONS

International Search Report for Application No. PCT/IB03/04502, dated May 26, 2004.
International Search Report for Application No. PCT/US2011/060388 dated May 30, 2012.
International Search Report for Application No. PCT/US2013/031352, Dated Apr. 25, 2013.
International Search Report for Application No. PCT/US2013/031389, Dated Jun. 3, 2013.
International Search Report for Application No. PCT/US2013/031485, Dated Jun. 25, 2013.
International Search Report for Application No. PCT/US2013/031681, Dated Jun. 14, 2013.
Invitation to Pay Additional Fees for International Application No. PCT/US2013/031380, Dated Nov. 28, 2013.
Jakobovits, A., "Production of fully human antibodies by transgenic mice" (1995) *Curr. Op. Biotechnol.*, 6:561-566.
Jespers, "Guiding the Selection of Human Antibodies from Phage Display Repertoires to a Single Epitope of an Antigen" (1994) *Bio/Technology*, 12:899-903.
Johnson et al. (Archives of Biochemistry and Biophysics 444 (2005) 7-14).
Kalyanpur, M., "Downstream Processing in the Biotechnology Industry" Molecular Biotechnology, vol. 22:87-98 (2002).
Karampetsou et al. (Q J Med 2010; 103:917-928).
Kaschak et al: "Characterization of the basic charge variants of a human IgGI: Effect of copper concentration in cell culture media", MABS, vol. 3, No. 6, Nov. 1, 2011, pp. 577-583.
Kazuaki, F. et al., "Enhancement of productivity of recombinant α-amidating enzyme by low temperature culture", Cytotechnology 31:85-94, 1999.
Kempeni, "Update on D2E7: a fully human anti-tumour necrosis factor-alpha monoclonal antibody" (2000) *Ann. Rheum. Dis.*, 59(Suppl. I):144-145.
Kempeni, J, "Preliminary results of early clinical trials with the fully human anti-TNFα monoclonal antibody D2E7", Ann. Rheum. Dis., 1999, pp. 170-172, vol. 58, (Suppl. I).
Kempf, C, et al. "Virus inactivation during production of intravenous immunoglobulin." *Transfusion* 1991; vol. 31: p. 423-427.
Khawli et al, "Charge variants in IgGI: Isolation, characterization, in vitro binding properties and pharmacokinetics in rats", MABS, vol. 2, No. 6, Nov. 1, 2010, pp. 613-624.
Kim, NS. et al., "Inhibition of sodium butyrate-induced apoptosis in recombinant Chinese hamster ovary cells by constitutively expressing antisense RNA of caspase-3", Biotechn. & Bioengin. 78(2):217-228, 2002.
Knight et al., "Construction and initial characterization of a mouse-human chimeric anti-TNF antibody" (1993) *Mol. Immunol.*, 30(16):1443-1453.
Kopaciewicz et al., "Retention Model for High-Performance Ion-Exchange Chromatography,"; Journal of Chromatoqraphy, 266:3-21 (1983).
Lerner, "Antibodies without immunization" (1992) *Science*, 258:1313-1314.
Lewis, "Use of alanine scanning mutagenesis to improve the affinity of an anti gp120 (HIV) antibody" (1994) *J. Cell. Biochem.*, 18D:215.
Li, F. et al., "Current Therapeutic Antibody Production and Process Optimization" BioProcessing Journal, vol. 4(5):23-30 (2005).
Lifely et al., "Glycosylation and Biological Activity of CAMPATH-1H Expressed in Different Cell Lines and Grown Under Different Culture Conditions", *Glycobiology*, 5(8):813-822 (1995).
Logan, John S. "Transgenic Animals: Beyond 'Funny Milk'", *Current Opinion in Biotechnology*, 4:591-595 (1993).
Lonberg et al., "Antigen-specific human antibodies from mice comprising four distinct genetic modifications" (1994) *Nature*, 368:856-859.
Lonberg et al., "Human Antibodies from Transgenic Mice" (1995) *Int. Rev. Immunol.*, 13:65-93.

Low, "Mimicking Somatic Hypermutation: Affinity Maturation of Antibodies Displayed on Bacteriophage Using a Bacterial Mutator Strain" (1996) *J. Mol. Biol.*, 260:359-368.
Low, Nigel: thesis extract (1996) *Cambridge University*.
Luo et al., "Understanding of C-terminal lysine variants in antibody production using mammalian cells" Abstract of papers, ACS, Anaheim, CA, US, Mar. 2011.
Luo et al: "Probing of C-terminal lysine variation in a recombinant monoclonal antibody production using Chinese hamster ovary cells with chemically defined media", Biotechnology and Bioengineering, vol. 109, No. 9, Apr. 11, 2012, pp. 2306-2315.
Ma, et al., "Generation and Assembly of Secretory Antibodies in Plants", *Science*, 268:716-719 (1995).
Maeda, et al., "Analysis of Nonhuman N-Glycans as the Minor Constituents in Recombinant Monoclonal Antibody Pharmaceuticals", *Anal. Chem.*, 84:2373-2379 (2012).
Mahler, et al. Induction and analysis of aggregates in a liquid IgG1-antibody formulation. Eur J Pharm Biopharm. 2005, 59(3):407-17; p. 408; col. 1-2; p. 409; col. 2, "2.2.2 Stirring stress".
Marks et al., "Human antibody fragments specific for human blood group antigens from a phage display library" (1993) *Bio/Technology*, 11:1145-1150.
Marks et al., "Molecular evolution of proteins on filamentous phage. Mimicking the strategy of the immune system" (1992) *J. Biol. Chem.* 267:16007-16010.
Marks, "By-passing immunization: Human antibodies from V-gene libraries displayed on phage" (1991) *J. Mol. Biol.*, 222:581-597.
Marks, "Human Monoclonal Antibodies from V-gene Repertoires Expressed on Bacteriophage." In *Antibody Engineering*, Second Edition, edited by Carl A.K. Borrebaeck (1995), pp. 53-88. New York: Oxford Univ. Press.
Marks, JD., "By-Passing Immunization: Building High Affinity Human Antibodies by Chain Shuffling" (1992) *Biotechnology*, 10:779-783.
Martin, A.C.R. "Accessing the Kabat antibody sequence database by computer" (1996)*Proteins: Structure, Function and Genetics*, 25:130-133.
Medynski, "Phage Display: All Dressed Up and Ready to Role" (1994) *Bio/Technology*, 12:1134-1136.
Mendez et al., "Functional transplant of megabase human immunoglobulin loci recapitulates human antibody response in mice" (1997) *Nature Genetics*, 15:146-156.
Meuwly, F. et al., "Conversion of a CHO cell culture process from perfusion to fed-batch technology without altering product quality", J.Biotechn. 123:106-116, 2006.
Miller et al. "Characterization of site-specific glycation during process development of a human therapeutic monoclonal antibody" Journal of Pharmaceutical Sciences, vol. 100, No. 7, Jul. 2011, 2543-2550.
Millipore, "Pellicon 2 Filters and Holders," 2003, pp. 1-8.
Moore, A., et al., "Effects of temperature shift on cell cycle, apoptosis and nucleotide pools in CHO cell batch cultures", Cytotechnology, 23:47-54, 1997.
Möller, Monoclonal antibodies to human tumor necrosis factor α: in vitro and vivo application (1990) *Cytokine*, 2(3):162-69.
Neuberger M. et al., "Mice perform a human repertoire" (1997) *Nature*, 386:25-26.
Ngo et al., "Kosmotropes enhance the yield of antibody purified by affinity chromatography using immobilized bacterial immunoglobulin binding proteins," Journal of Immunoassay & Immunochemistry, (2008) 29(1):105-115.
Nilsson, "Antibody engineering" (1995) *Current Opinion in Structural Biology*, 5:450-456.
Nogal, B., Chhiba, K. and Emery, J. C. (2012), Select host cell proteins coelute with monoclonal antibodies in protein a chromatography. Biotechnol Progress, 28: 454-458.
Noguchi et al., "Failure of Human Immunoresponse to N-Glycolylneuraminic Acid Epitope Contained in Recombinant Human Erythropoietin", *Nephron*, 72:599-603 (1996).
Noguchi et al., "Immunogenicity of N-Glycolylneuraminic Acid-Containing Carbohydrate Chains of Recombinant Human Erythropoietin Expressed in Chinese Hamster Ovary Cells", *J. Biochem.*, 117:59-62 (1995).

(56) References Cited

OTHER PUBLICATIONS

Oh, D-K. et al., "Increased erythritol production in fed-batch cultures of *Torula* sp. by controlling glucose concentration", J. Industrial Microb. & Biotechn. 26(4): 248-252, 2001.

Oh, SKW, et al., "Substantial Overproduction of Antibodies by Applying Osmotic Pressure and Sodium Butyrate", Biotechn. Bioengin. 42(5):601-610, 1993.

Osbourn, "From rodent reagents to human therapeutics using antibody guided selection" (2005) *Methods*, 36(1):61-68.

Perchiacca et al., "Aggregation-resistance domain antibodies engineered with charged mutations; near the edges of the complementarity-determining regions," Protein Engineering Design & Selection, 25: 10 (591-601) 2012.

Pietersz et al., "In vitro and in vivo Antitumor Activity of a Chimeric anti-CD19 Antibody", *Cancer Immunol. Immunother.*, 41:53-60 (1995).

Potter et al., "Antibody Production in the Baculovirus Expression System", *Intern. Rev. Immunol.*, 10:103-112 (1993).

Poul et al., "Design of Cassette Baculovirus Vectors for the Production of Therapeutic Antibodies in Insect Cells", *Immunotechnology*, 1:189-196 (1995).

Queen, C., "A humanized antibody that binds to the interleukin 2 receptor" (1989) *Proc. Natl. Acad. Sci. USA*, 86(24):10029-10033.

Rader et al. "A phage display approach to rapid antibody humanization: Designed combinatorial V gene libraries" (1998) *Proc Natl Acad Sci USA*, 95:8910-8915.

Raju, TS. "Glycosylation Variations with Expression Systems and Their Impact on Biological Activity of Therapeutic Immunoglobulins", *BioProcess International.*, 44-53 (2003).

Reichert JM., et al., "Monoclonal antibody successes in the clinic", Nature Biotech. 23(9):1073-1078, 2005.

Reinhart, "Assessment of the safety and efficacy of the monoclonal anti-tumor necrosis factor antibody-fragment, MAK 195F, in patients with sepsis and septic shock: a multicenter, randomized, placebo-controlled, dose-ranging study" (1996) *Crit. Care Med.*, 24(5):733-742.

Rheinwald JG, et al., "Growth of Cultured Mammalian Cells on Secondary Glucose Sources", Cell, 287-293, 1974.

Ridder et al., "Generation of Rabbit Monoclonal Antibody Fragments from a Combinatorial Phage Display Library and Their Production in Yeast *Pichia pastoris*", *Biotechnology*, 13:255-260 (1995).

Riechmann, "Phage display and selection of a site-directed randomized single-chain antibody Fv fragment for its affinity improvement" (1993) *Biochemistry*, 32(34):8848-8855.

Rube et al. (Int. J. Radiation Oncology Biol. Phys., vol. 56, No. 5, pp. 1414-1425,2003).

Rudikoff et al., "Single amino acid substitution altering antigen-binding specificity" (1982) *Proc. Natl. Acad. Sci. USA*, 70:1979-1983.

Salfeld, "Development of a Fully Human Antibody to TNF by Phage Display Technology," IBC Conference, *Antibody Engineering*, San Diego (Dec. 1996), pp. 1-36.

Sandadi, S. et al., "Heuristic Optimization of Antibody Production by Chinese Hamster Ovary Cells", Biotech. Progress, American Institute of Chem. Engineers: 21(5): 1537-1542, 2005.

Sandhu, J. "Protein engineering of antibodies" (1992) *Critical Reviews in Biotechnology*, 12:437-462.

Santora et al., "Characterization of recombinant human monoclonal tissue necrosis factor-alpha antibody using cation exchange HPLC and capillary isoelectric focusing," Analytical Biochemistry, (1999) 275:98-108.

Santora, "Characterization of Noncovalent Complexes of Recombinant Human Monoclonal Antibody and Antigen Using Cation Exchange, Size Exclusion Chromatography, and BIAcore" (2001) *Analytical Biochemistry*, 299:119-129.

Sato et al, "Stimulation of monoclonal antibody production by human-human hybridoma cells with an elevated concentration of potassium or sodium phosphate in serum-free medium," Cytotechnology 2:63-67, 1989.

Schwieterman, "Immunosuppression in Combination with Monoclonal Antibodies" in Biologic Agents in Autoimmune Disease (Mar. 2-4, 1995).

Seresht et al., "The impact of phosphate scarcity on pharmaceutical protein production in *S. cerevisiae*: linking transcriptomic insights to phenotypic responses" Microbial Cell Factories. 2011, 10: 104.

Sheeley et al., "Characterization of Monoclonal Antibody Glycosylation: Comparison of Expression Systems and Identification of Terminal α-Linked Galactose", *Anal. Biochem.*, 247(1):102-110 (1997).

Sheikh et al., "Studies of the digestion of bradykinin, lysyl bradykinin, and kinin-degradation products by carboxypeptidases A, B, and N;". Biochemical Pharmacology. 1986, 35: 1957-1963.

Shih, "Effects of Anions on the Deamidation of Soy Protein". Journal of Food Science. 1991, 56: 452-454.

Shukla et al., "Host cell protein clearance during protein A chromatography: development of an improved column wash step," Biotechnology Progress, (2008) 24(5):1115-1121.

Shukla et al., "Recent advances in large-scale production of monoclonal antibodies and related proteins," Trends in Biotechnology, (2010) 28(5):253-261.

Sioud et al., "Characterization of naturally occurring autoantibodies against tumour necrosis factor-alpha (TNF-α): in vitro function and precise epitope mapping by phage epitope library" (1994) *Clin. Exp. Immunol.*, 98:520-525.

Sung, Y.H. et al., "Yeast hydrolysate as a low-cost additive to serum-free medium for the production of human thrombpoietin in suspension cultures of Chinese hamster ovary cells", *Applied Microbilolgy and Biotechnology* 63:5, 527-536, 2004.

Takagi, M. et al., "The effect of osmolarity on metabolism and morphology in adhesion and suspension chinese hamster ovary cells producing tissue plasminogen activator", Cytochnology 32:171-179, 2000.

Tamura et al., "Structural correlates of an anticarcinoma antibody: identification of specificity-determining residues (SDRs) and development of a minimally immunogenic antibody variant by retention of SDFs only," *J. Immun.* (2000) 164:1432-1441.

Tan et al. (Biotechnol. Appl. Biochem. (1999) 30, 59-64).

Taylor et al., "Human immunoglobulin transgenes undergo rearrangement, somatic mutation and class switching in mice that lack endogenous IgM" (1994) *Int. Immunol.*, 6:579-591.

Teichmann, S. Declaration dated Dec. 7, 2010 from opposition proceedings in EP 0929578.

The MW Calculator available at the Sequence Manipulation Suite (see http://bioinformatics.org/sms2/index.html), downloaded Feb. 25, 2014.

The pI Calculator available at the Sequence Manipulation Suite (see <http://bioinformatics.org/sms2/index.html>), downloaded Feb. 25, 2014, p. 1).

The Statement on a Nonproprietary Name Adopted by the USAN Council for Adalimumab, p. 1, downloaded on May 19, 2011 from http://www.ama-assn.org/resources/doc/usan/adalimumab.doc.

Thompson, "Affinity maturation of a high-affinity human monoclonal antibody against the third hypervariable loop of human immunodeficiency virus: use of phage display to improve affinity and broaden strain reactivity" (1996) *J. Mol. Biol.*, 256(1):77-88.

Thorp, "Tumour Necrosis Factor Induction of ELAM-1 and ICAM-1 on Human Umbilical Vein Endothelial Cells—Analysis of Tumour Necrosis Factor Receptor Interaction" (1992) *Cytokine*, 4(4): 313-319.

Tomiya et al., "Comparing N-glycan processing in mammalian cell lines to native and engineered; lepidopteran insect cell lines," Glycoconjuqate Journal 21 :343-360 (2004).

Tomlinson, "The repertoire of human germline VH sequences reveals about fifty groups of VH segments with different hypervariable loops" (1992) *J. Mol. Biol.*, 227:776-98.

Tomlinson, "The structural repertoire of the human Vk domain" (1995) *The EMBO J.*, 14(18):4628-38.

Tracey, "Tumor necrosis factor: A pleiotropic cytokine and therapeutic target" (1994) *Annu. Rev. Med.*, 45:491-503.

Tsuchiyama et al., "Comparison of anti-TNF alpha autoantibodies in plasma and from EBV transformed lymphocytes of autoimmune and normal individuals" (1995) *Hum. Antibod. Hybridomas*, 6(2):73-76.

(56) References Cited

OTHER PUBLICATIONS

Vallee B et al. "The role of zinc in carboxypeptidase" The Journal of Biological Chemistry, (1960) 235, 1; 64-69.

Valliere-Douglass et al., "Glutamine-linked and Non-consensus Asparagine-linked Oligosaccharides Present in Human Recombinant Antibodies Define Novel Protein Glycosylation Motifs", *J. Biol. Chem.*, 285:16012-16022 (2010).

Van Der Poll, "Effect of postponed treatment with an anti-tumour necrosis factor (TNF) F(ab')2 fragment on endotoxin-induced cytokine and neutrophil responses in chimpanzees" (1995) *Clin. Exp. Immunol.*, 100:21-25.

Van Lent PL, et al. "The impact of protein size and charge on its retention in articular cartilage" J Rheumatol. Aug. 1987;14(4):798-805.

Varasteh et al. Optimization of Anti-Rh D Immunoglobulin Stability in the Lyphiliization Process. Iranian Journal of Basic Medical Sciences, Spring 2008, vol. 11, No. 1. pp. 55-61.

Vaughan, "Human antibodies by design" (1998) *Nature Biotechnology*, 16:535-539.

Wagner et al., "Antibodies generated from human immunoglobulin miniloci in transgenic mice" (1994) *Nucl. Acids Res.* 22:1389-1393.

Wagner et al., "The diversity of antigen-specific monoclonal antibodies from transgenic mice bearing human immunoglobulin gene miniloci" (1994) *Eur. J. Immunol.*, 24:2672-2681.

Ward, "Binding activities of a repertoire of single immunoglobulin variable domains secreted from *Escherichia coli*" (1989) *Nature*, 341:544-546.

Wedemayer et al., "Structural insights into the evolution of an antibody combining site" (1997) *Science,* 276:1665-1669.

Wiendl et al. (BioDrugs. 2002;16(3):183-200).

Williams et al., "Kinetic analysis by stopped-flow radiationless energy transfer studies: effect of anions on the activity of carboxypeptidase A". Biochemistry. 1986, 25, 94-100.

Winter, "Humanized antibodies" (1993) *Immunol. Today,* 14(6):243-246.

Winter, "Making antibodies by phage display technology" (1994) *Annu. Rev. Immunol.,* 12:433-455.

Wurm, FM, "Production of recombinant protein therapeutics in cultivated mammalian cells", Nature Biotechnology 22(11):1393-1398, 2004.

Yigzaw et al., "Exploitation of the adsorptive properties of depth filters for host cell protein removal during monoclonal antibody purification," Biotechnology Progress, (2006) 22(1):288-296.

Yumioka et al., "Screening of effective column rinse solvent for Protein-A chromatography," Protein Expression and Purification, (2010) 70(2): 218-223.

Zatarain-Rios E and Mannik M, "Charge-charge interactions between articular cartilage and cationic antibodies, antigens, and immune complexes," Arthritis Rheum. Nov. 1987;30(11):1265-73.

Zhang et al., "Isolation and characterization of charge variants using cation exchange displacement chromatography," 1218(31): 5079-5086, 2011.

Zou et al., "Dominant expression of a 1.3 Mb human Ig kappa locus replacing mouse light chain production" (1996) *FASEB J.,* 10:1227-1232.

\* cited by examiner

Figure 1: Process Chromatogram of pH Gradient Elution

Figure 2: Process Chromatogram of Linear Gradient Elution by increasing Anion Concentration Figure 3: Process Chromatogram of Fractionation of 300 g/L Load and Wash Figure 4: Effect of pH on AR reduction Figure 5: Process Chromotogram at Different Salt (Cation) Concentrations Note: AR reductions and protein recovery yields were calculated based on the Flow Through fractions at about loading 200 g protein per L of resin Effect of pH, conductivity and protein load amount on AR reduction and Yield Effect of pH, conductivity and protein load amount on AR reduction and Yield Figure 23: AR Growth at 25°C
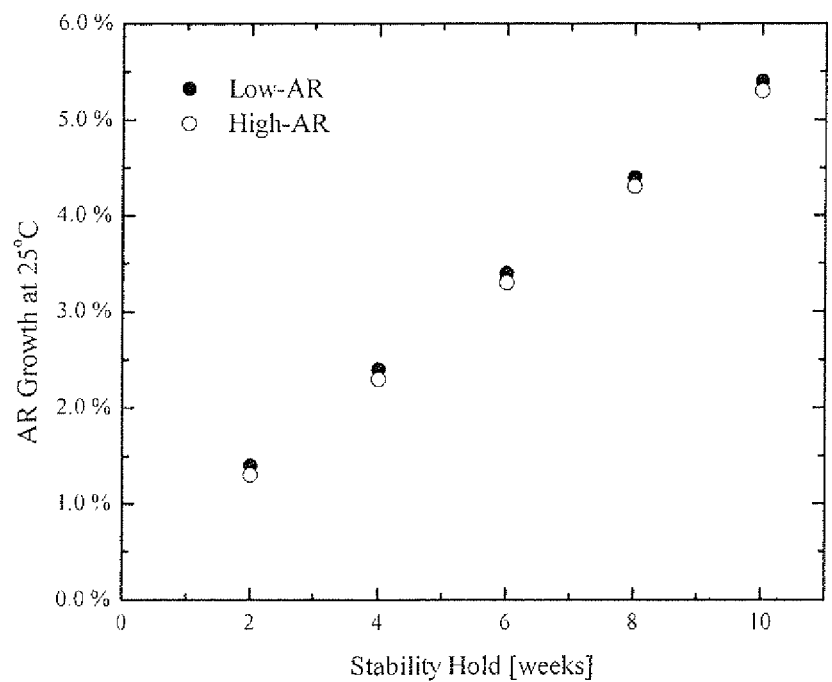

Figure 24: Effect of AEX adsorbent pKa
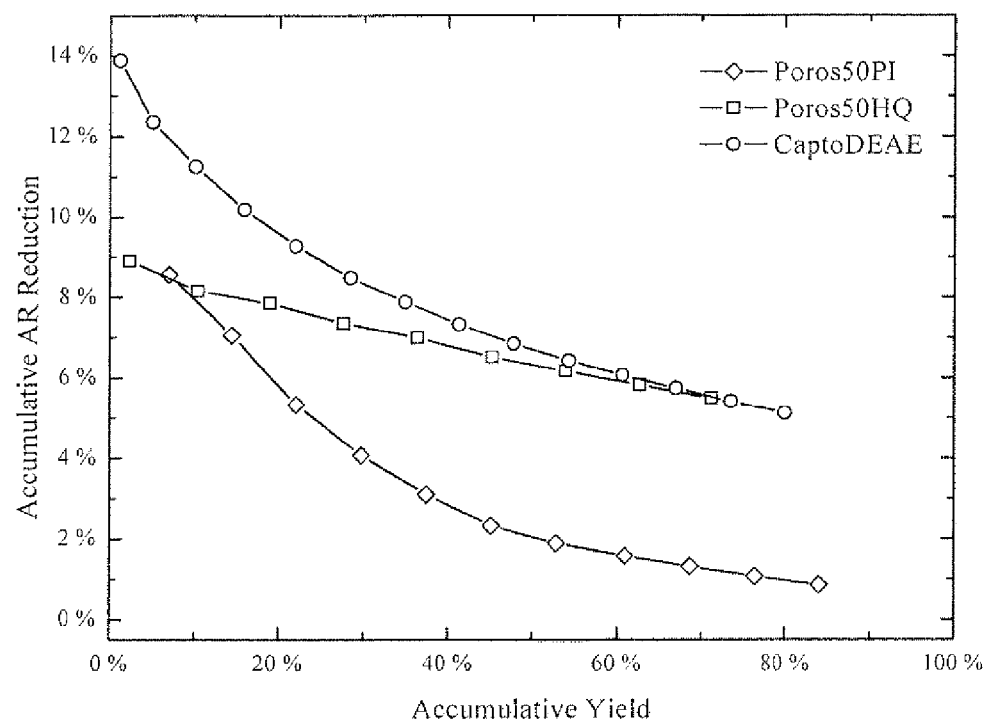

LOW ACIDIC SPECIES COMPOSITIONS

CROSS REFERENCE TO RELATED APPLICATIONS

The present application claims priority to U.S. Provisional Application No. 61/636,511, filed on Apr. 20, 2012.

1. INTRODUCTION

The instant invention relates to the field of protein production and purification, and in particular to compositions and processes for controlling the amount of product-related substances (e.g., product charge variants, aggregates, and fragments) and/or process-related impurities (e.g., host cell proteins and media components) present in purified preparations by applying particular chromatography conditions during such protein purification.

2. BACKGROUND OF THE INVENTION

The production of proteins for biopharmaceutical applications typically involves the use of cell cultures that are known to produce proteins exhibiting varying levels of heterogeneity. Such heterogeneity includes, but is not limited to, the presence of product-related species, such as charged species heterogeneity, consisting of acidic species and basic species. In monoclonal antibody (mAb) preparations, such acidic species heterogeneities can be detected by various methods, such as WCX-10 HPLC (a weak cation exchange chromatography) or IEF (isoelectric focusing). In certain embodiments, the acidic species identified using such techniques comprise a range of product-related substances such as antibody product fragments (e.g., Fc and Fab fragments), and/or post-translation modifications of the antibody product, such as, deamidated and/or glycoslyated antibodies. For example, in a sample of the human IgG antibody adalimumab, WCX-10 analysis measured the presence of acidic species that can be divided, based on residence time, into two groups: acidic region 1 (AR1) and acidic region 2 (AR2). Because of their similar chemical characteristics to the antibody molecules of interest, reduction of acidic species is a particular challenge in monoclonal antibody purification.

There remains a need in the art for high-efficiency methods of purifying proteins of interest, e.g., antibodies, away from product-related substances and process-related impurities at relatively low cost. Reduction of such substances and/or impurities is particularly advantageous in the context of commercially produced recombinant bio-therapeutics as such substances and/or impurities have the potential to impact numerous product characteristics, including, but not limited to, product stability, product safety and product efficacy.

3. SUMMARY OF THE INVENTION

In certain embodiments, the present invention is directed to process-related impurity-reduced and/or product-related substance-modulated preparations of a protein of interest. In certain embodiments, the process-related impurities include, but are not limited to host cell proteins (HCPs), host nucleic acids, chromatographic materials, and media components. In certain embodiments, the product-related substances include, but are not limited to charge variants, such as acidic species and basic species. In certain embodiments, such acidic species correspond to heterogeneity in the distribution of protein fragments (e.g., Fc and Fab fragments of antibodies), and/or post-translation modifications of the proteins, such as, deamidated and/or glycoslyated proteins, in the population of proteins, and such heterogeneity particularly of interest when it arises in the context of recombinant protein production. Further, the present invention is directed toward pharmaceutical compositions comprising one or more proteins purified by a method described herein. In another aspect, such compositions further comprise one or more pharmaceutical agents.

In certain embodiments, the present invention is directed to a method for preparing a process-related impurity-reduced and/or product-related substance-modulated composition comprising a protein of interest wherein a chromatographic separation is performed to identify the particular conditions, e.g., salt concentration, pH, temperature, load amount and conditions, and washing conditions, sufficient to elicit the desired fractionation profile, e.g., fractionation of product-related substances, such as acidic species and lysine variants, of a sample comprising the protein of interest and at least one process-related impurity and/or at least one product-related substance. In certain embodiments, the method will further comprise pooling of the resulting fractions comprising the desired process-related impurity-reduced and/or product-related substance-modulated composition comprising a protein of interest.

In certain embodiments, the present invention is directed to methods for isolating and purifying a protein, for example, an antibody, or an antigen-binding portion thereof, from a sample in order to exert control over the presence of process-related impurities and/or product-related substances.

In certain embodiments, the methods of purifying a protein, such as an antibody or antigen-binding portion thereof, from a sample, as described herein, reduces the amount of acidic species present in the resulting composition. In certain embodiments, the resulting composition is substantially free of acidic species. In certain embodiments, the resulting composition is substantially free of one or more acidic sub-species, for example, with regard to the purification of Adalimumab, the composition is substantially free of AR1 and/or AR2. In certain embodiments, the methods described herein reduce the amount of host cell proteins ("HCPs") present in the resulting composition. In certain embodiments, the resulting composition is substantially free of HCPs. In one aspect, the sample mixture to be purified comprises a partially purified cell line harvest wherein the cell line is employed to produce specific proteins of the present invention. In a particular aspect, the sample mixture is prepared from a cell line used to produce anti-TNF-α antibodies.

In certain aspects, the invention is directed to methods of protein purification employing chromatography, preferably chromatography that utilizes a multimodal (also known as "mixed mode" or "MM") media.

In certain embodiments, the multimodal media comprises functional groups which exhibit anion exchange and/or hydrophobic interactions. In certain embodiments, the multimodal media comprises a cross-linked agarose with a ligand, for example, N-Benzyl-N-methyl ethanol amine, that exhibits ionic interactions, hydrogen bonding and hydrophobic interactions. In certain embodiments, the cross-linked agarose with a ligand (N-Benzyl-N-methyl ethanol amine) has the following structure:

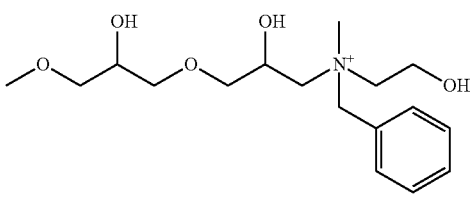 [SMILES: COCC(O)COCC(O)C[N+](C)(CCO)Cc1ccccc1]

In certain embodiments, the multimodal media comprises a cross-linked cellulose exhibiting porosity. In certain embodiments, the cross-linked cellulose is a phenylpropylamine having the following structure:

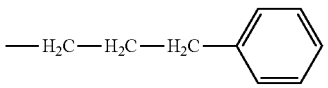

In certain embodiments, the cross-linked cellulose is a hexylamine having the following structure:

In certain embodiments of the present invention, a sample comprising the protein of interest, such as an antibody or antigen-binding portion thereof, is subjected to chromatography that utilizes a multimodal media, wherein the sample is subjected to a pH adjustment during loading. In one aspect, the pH is adjusted to a basic pH, or an increase in pH. An example of a suitable pH is between about a pH of 7 and 8.2, preferably a pH of between about 7.5 and 8.2. In certain embodiments the selection of appropriate pH will be based on the characteristics of the antibody and/or acidic species of interest. In certain embodiments, the pH will be selected to be about 0 to 3 units lower than the pI of the protein. In certain embodiments, it is in the range of 1 to 2 units lower. In certain embodiments, it is in the range of 1 to 1.5 units lower.

Certain embodiments of the present invention involve subjecting a sample mixture comprising a protein of interest, such as an antibody or antigen-binding portion thereof, to chromatography that utilizes a multimodal media, wherein the sample is subjected to a conductivity adjustment during loading. In one aspect, the conductivity is adjusted to between about 1 and 86 mS/cm, preferably between about 2 and 14 mS/cm. In certain embodiments, alternative ranges of conductivity are employed, which would be based on the characteristics of the antibody and/or acidic species of interest.

Certain embodiments of the present invention involve subjecting a sample comprising a protein of interest, such as an antibody or antigen-binding portion thereof, to chromatography that utilizes a multimodal media, wherein the sample is subjected to an adjustment in the amount of protein load used in the multimodal chromatography. In one aspect, the total protein load to the column is of between about 5 and 1000 g/L, or between about 50 and 500 g/L, between about 75 and 300 g/L, or between about 100 and 250 g/L. In certain embodiments, the protein concentration of the load protein mixture is adjusted to a protein concentration of the material loaded to the column of about 0.5 and 50 g/L, or between about 1 and 20 g/L.

In certain embodiments, the methods of the present invention involves subjecting a sample comprising a protein of interest, such as an antibody or antigen-binding portion thereof, to chromatography that utilizes an anion exchange (AEX) adsorbent material and an aqueous salt solution under loading conditions that permit both the protein of interest and non-target proteins to bind to the AEX adsorbent and collecting any unbound material with reduced levels of acidic species (and optionally reduced levels of one or more product related impurities/substances or process related impurities) and subsequently wing the adsorbent with awash buffer comprising the same, or substantially similar, aqueous salt solution used in the loading sample and collecting the effluent containing reduced levels of acidic species (and optionally reduced levels of one or more product related impurities/substances or process related impurities). In certain embodiments, the salt concentration is between 0.5 mM and 50 mM, or 2 mM and 40 mM, or 5 mM and 20 mM, depending on the salt type and AEX adsorbent being used. In certain embodiments, the concentration of the anionic and/or cationic agent in aqueous salt solution is increased or decreased to achieve a pH of between about 5 and 10, or between about 7 and 9. In certain embodiments, the aqueous salt solution comprises an anionic agent at a concentration of about 5 mM, 10 mM or 18.5 mM, and an amount of a cationic agent sufficient to achieve a pH of 8.8 or 9.0.

In certain embodiments of the present invention involve subjecting a sample comprising the putative protein of interest, such as an antibody or antigen-binding portion thereof, to chromatography that utilizes a AEX, wherein the sample is subjected to an adjustment in the amount of protein concentration and load. In one aspect, the total protein load to the column of between about 50 and 500 g/L, or between about 75 and 350 g/L, or between about 200 and 300 g/L. In certain embodiments, the protein concentration of the load protein mixture is adjusted to a protein concentration of the material loaded to the column of about 0.5 and 50 g/L, between about 1 and 20 g/L, or between 3 and 10 g/L.

In certain embodiments, the methods of the present invention involves subjecting a sample comprising a putative protein of interest, such as an antibody or antigen-binding portion thereof, to chromatography that utilizes a cation exchange (CEX) adsorbent material and an aqueous solution under loading conditions that permit both the protein of interest and non-target proteins to bind to the CEX adsorbent, wherein acidic species and non-target proteins are washed from the CEX adsorbent material using a wash buffer comprising the same, or substantially similar, aqueous solution as the loading buffer, and wherein the bound protein of interest is subsequently recovered with an elution buffer having a higher conductivity than the loading buffer.

In certain embodiments of the present invention involve subjecting a sample comprising the protein of interest, such as an antibody or antigen-binding portion thereof, to chromatography that utilizes a CEX, wherein the aqueous solution for loading and wash is a combination of pH and ionic concentration to allow the removal the acidic species in the unbound wash fractions. The pH employed in certain of such embodiments is adjusted such that it is below the pI of the protein of interest.

In certain embodiments of the present invention involve subjecting a sample comprising the putative protein of interest, such as an antibody or antigen-binding portion thereof, to chromatography that utilizes a CEX, wherein the sample is subjected to an adjustment in the amount of protein concentration and load. In one aspect, the total protein load to the column of between about 5 and 150 g/L, or between about 10 and 100 g/L, between about 20 and 80 g/L, or between about 30 and 50 g/L. In certain embodiments, the protein concentration of the load protein mixture is adjusted to a protein concentration of the material loaded to the column of about 0.5 and 50 g/L, or between about 1 and 20 g/L.

In certain embodiments, control over the amount of acidic species in the protein compositions described herein is exerted by employing one or more of the foregoing methods during the production and purification of the desired proteins, such as antibodies or antigen-binding portions thereof, described herein.

In certain embodiments, the sample is subject to a first chromatographic step prior to the multimodal/AEX or CEX media chromatography described above. The sample in each case is prepared appropriately to achieve the target pH and ion concentration prior to separation on the different modes of chromatography. Such prior chromatographic steps include ion exchange and/or affinity chromatography. Non-limiting examples of chromatographic supports for use in the first chromatographic step include, but are not limited to, affinity chromatographic resins, such as, but not limited to, Protein A resin and Protein G resin, or other affinity supports such as those comprising the antigen against which an antibody of interest was raised, as well as affinity supports comprising an Fc binding protein. In one aspect, where the protein of interest is an antibody, a sample is loaded on a protein A affinity column chromatography and eluted with a buffer system containing buffer components to be used in the multimodal media chromatography. During low pH viral inactivation, the pH is adjusted to pH 3.5 to 3.7 with acid (e.g., the same as the acidic component of the multimodal media chromatography equilibration buffer system) and held for about 30 to 90 minutes. The material is then neutralized with base) to the designed pH. In certain embodiments, the buffer is a Tris/acetate buffer system. In certain embodiments, the buffer is a trolamine/NaCl buffer. The material is then clarified with filters. The eluate can be monitored using techniques well known to those skilled in the art. For example, the absorbance at $OD_{280}$ can be followed. The eluated fraction(s) of interest can then be prepared for further processing with multimodal chromatography, AEX or CEX media chromatography.

The purity of the proteins of interest, including but not limited process-related impurities and product-related substances, in the sample resulting from practice of the chromatographic strategies described herein can be analyzed using methods well known to those skilled in the art, e.g., weak cation exchange chromatography (WCX), capillary isoelectric focusing (cIEF), size-exclusion chromatography, Poros™ A HPLC Assay, HCP ELISA, Protein A ELISA, and western blot analysis.

4. BRIEF DESCRIPTIONS OF THE DRAWINGS

FIG. 23 depicts the AR Growth at 25° C. of low and high AR containing samples.

FIG. 24 depicts the effect of AEX adsorbent pKa for mAb B with several different AEX adsorbents, with different pKa values, run at with an acetate/Tris buffer at pH 9.1.

5. DETAILED DESCRIPTION OF THE INVENTION

Figure 1:
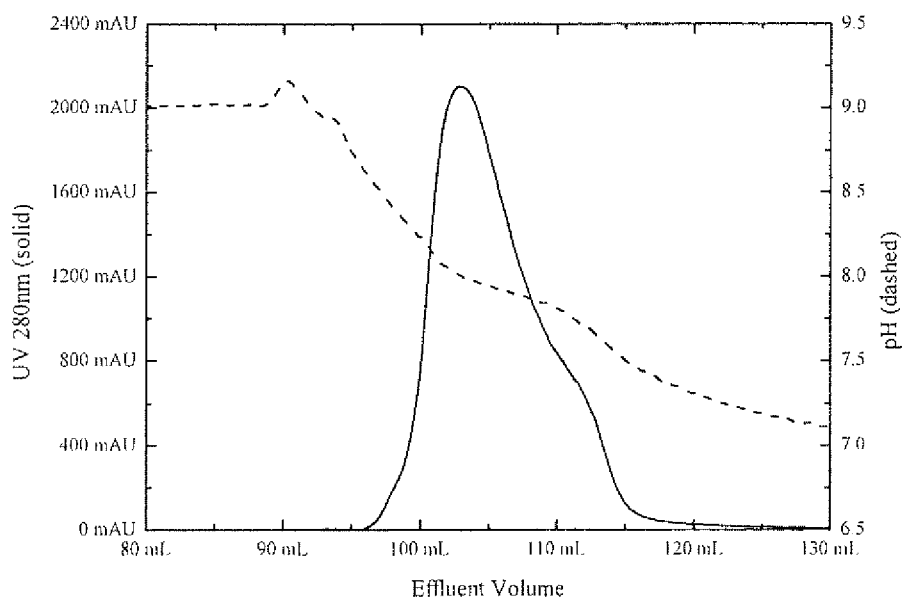
FIG. 1 depicts a process chromatogram of pH gradient elution in the context of AEX chromatography.

The instant invention relates to the field of protein purification. In particular, the instant invention relates to compositions and processes for controlling the amount of product-related substances (e.g., product charge variants, aggregates, and fragments) and/or process-related impurities (e.g., host cell proteins and media components) present in purified preparations of a protein of interest. In certain embodiments, the methods described herein involve the purification of a protein, such as, but not limited to an antibody or antigen-binding portion thereof, by multimodal chromatography, wherein the multimodal (MM) media comprises both ion exchange and hydrophobic interaction functional groups and an aqueous salt solution, wherein the same or substantially the same aqueous salt solution is used as a loading buffer and a wash buffer using which the said protein of interested is collected with, in the column effluent.

In certain embodiments, the methods described herein involve the purification of a protein, such as, but not limited to an antibody or antigen-binding portion thereof, by chromatography comprising an anion exchange (AEX) adsorbent material and an aqueous salt solution, wherein the same or substantially the same aqueous salt solution is used as a loading buffer and a wash buffer using which the said protein of interested is collected with, in the column effluent. In certain embodiments, the methods described herein involve the purification of a protein, such as, but not limited to an antibody or antigen-binding portion thereof, by chromatography comprising a cation exchange (CEX) adsorbent material and an aqueous salt solution, wherein the same or substantially the same aqueous salt solution is used as a loading buffer and a wash buffer, wherein the wash buffer removes acidic species and non-target proteins bound to the CEX adsorbent material, and wherein the target protein bound to the CEX adsorbent material is eluted with a buffer having a higher conductivity and/or pH than the loading/wash buffer. In certain embodiments, the present invention is directed toward pharmaceutical compositions comprising one or more proteins, such as, but not limited to an antibody or antigen-binding portion thereof, purified by a method described herein.

For clarity and not by way of limitation, this detailed description is divided into the following sub-portions:
 5.1. Definitions;
 5.2. Antibody Generation;
 5.3. Antibody Production;
 5.4. Antibody Purification;
 5.5. Methods of Assaying Sample Purity;
 5.6. Further Modifications; and
 5.7. Pharmaceutical Compositions
 5.1. Definitions In order that the present invention may be more readily understood, certain terms are first defined.

The term "product", as used herein refers to a protein of interest, which may be present in the context of a sample comprising one or more process-related impurities and/or product-related substances. In certain embodiments, the product, i.e., the protein of interest is an antibody or antigen binding fragment thereof.

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region (CH). The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The term "antibody", as used herein, also includes alternative antibody and antibody-like structures, such as, but not limited to, dual variable domain antibodies (DVD-Ig).

The term "antigen-binding portion" of an antibody (or "antibody portion") includes fragments of an antibody that retain the ability to specifically bind to an antigen (e.g., hIL-12, hTNFα, or hIL-18). It has been shown that the antigen-binding function of an antibody can be performed by fragments of a full-length antibody. Examples of binding fragments encompassed within the term "antigen-binding portion" of an antibody include (i) a Fab fragment, a monovalent fragment comprising the VL, VH, CL and CH1 domains; (ii) a F(ab')2 fragment, a bivalent fragment comprising two Fab fragments linked by a disulfide bridge at the hinge region; (iii) a Fd fragment comprising the VH and CH1 domains; (iv) a Fv fragment comprising the VL and VH domains of a single arm of an antibody, (v) a dAb fragment (Ward et al., (1989) Nature 341:544-546, the entire teaching of which is incorporated herein by reference), which comprises a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-426; and Huston et al. (1988) Proc. Natl. Acad. Sci. USA 85:5879-5883, the entire teachings of which are incorporated herein by reference). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al. (1993) Proc. Natl. Acad. Sci. USA 90:6444-6448; Poljak, R. J., et al. (1994) Structure 2:1121-1123, the entire teachings of which are incorporated herein by reference). Still further, an antibody may be part of a larger immunoadhesion molecule, formed by covalent or non-covalent association of the antibody with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101, the entire teaching of which is incorporated herein by reference) and use of a cysteine residue, a marker peptide and a C-terminal polyhistidine tag to make bivalent and biotinylated scFv molecules (Kipriyanov, S. M., et al. (1994) Mol. Immunol. 31:1047-1058, the entire teaching of which is incorporated herein by reference). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. In one aspect, the antigen binding portions are complete domains or pairs of complete domains.

The terms "Kabat numbering" "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242, the entire teachings of which are incorporated herein by reference). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

The term "human antibody" includes antibodies having variable and constant regions corresponding to human germline immunoglobulin sequences as described by Kabat et al. (See Kabat, et al. (1991) Sequences of proteins of Immunological Interest, Fifth Edition, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), e.g., in the CDRs and in particular CDR3. The mutations can be introduced using the "selective mutagenesis approach." The human antibody can have at least one position replaced with an amino acid residue, e.g., an activity enhancing amino acid residue which is not encoded by the human germline immunoglobulin sequence. The human antibody can have up to twenty positions replaced with amino acid residues which are not part of the human germline immunoglobulin sequence. In other embodiments, up to ten, up to five, up to three or up to two positions are replaced. In one embodiment, these replacements are within the CDR regions. However, the term "human antibody", as used herein, is not intended to include antibodies in which CDR sequences derived from the germline of another mammalian species, such as a mouse, have been grafted onto human framework sequences.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see, e.g., Taylor, L. D., et al. (1992) Nucl. Acids Res. 20:6287-6295, the entire teaching of which is incorporated herein by reference) or antibodies prepared, expressed, created or isolated by any other means that involves splicing of human immunoglobulin gene sequences to other DNA sequences. Such recombinant human antibodies have variable and constant regions derived from human germline immunoglobulin sequences (see, Kabat, E. A., et al. (1991) Sequences of Proteins of Immunological Interest, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis approach or back-mutation or both.

An "isolated antibody" includes an antibody that is substantially free of other antibodies having different antigenic specificities. Moreover, an isolated antibody may be substantially free of other cellular material and/or chemicals.

The term "Koff", as used herein, is intended to refer to the off rate constant for dissociation of an antibody from the antibody/antigen complex.

The term "Kd", as used herein, is intended to refer to the dissociation constant of a particular antibody-antigen interaction.

The phrase "nucleic acid molecule" includes DNA molecules and RNA molecules. A nucleic acid molecule may be single-stranded or double-stranded, but in one aspect is double-stranded DNA.

The phrase "isolated nucleic acid molecule," as used herein in reference to nucleic acids encoding antibodies or antibody portions (e.g., VH, VL, CDR3), e.g. an antibody having a weak binding capacity for a Protein A resin. The phrase "isolated nucleic acid molecule" is also intended to include sequences encoding bivalent, bispecific antibodies, such as diabodies in which VH and VL regions contain no other sequences other than the sequences of the diabody.

The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "modifying", as used herein, is intended to refer to changing one or more amino acids in the antibodies or antigen-binding portions thereof. The change can be produced by adding, substituting or deleting an amino acid at one or more positions. The change can be produced using known techniques, such as PCR mutagenesis.

The term "about", as used herein, is intended to refer to ranges of approximately 10-20% greater than or less than the referenced value. In certain circumstances, one of skill in the art will recognize that, due to the nature of the referenced value, the term "about" can mean more or less than a 10-20% deviation from that value.

The term "preparative scale", as used herein, refers to a scale of purification operation that can be readily scaled-up and implemented at large scale manufacturing while still providing desired separation. For instance, one skilled in the field may develop a process using, e.g., a 0.5 cm (i.d.)×20 cm (L) column in the lab, and transfer it to large scale production using, e.g., a 30 cm (i.d.)×20 cm (L) column packed with the same resin and operated with the same set of buffers, same linear flow rates (or residence times) and buffer volumes. In preparative scale separation, column bed height is typically ≤about 30 cm and column pressure drop ≤about 5 bar.

The term "aggregates" used herein means agglomeration or oligomerization of two or more individual molecules, including but not limiting to, protein dimers, trimers, tetramers, oligomers and other high molecular weight species. Protein aggregates can be soluble or insoluble.

The term "fragments" used herein refers to any truncated protein species from the target molecule due to dissociation of peptide chain, enzymatic and/or chemical modifications. For instance, antibody fragments include, but not limited to, Fab, F(ab')$_2$, Fv, scFv, Fd, dAb, or other compositions that contain a portion of the antibody molecule.

The term "charge variants", as used herein, refers to the full complement of product variants including, but not limited to acidic species and basic species (e.g., Lys variants). In certain embodiments, such variants can include product aggregates and/or product fragments, to the extent that such aggregation and/or fragmentation results in a product charge variation.

As used herein, the term "lysine variant heterogeneity" refers to a characteristic of a population of proteins wherein the population consists of proteins of substantially identical amino acid sequence, but where the population exhibits variation in the presence or absence of C-terminal lysine residues. Although such lysine variant heterogeneity can be observed under general cell culture conditions, the use of particular cell culture conditions, as detailed below, can increase or decrease the distribution or amount of lysine variant heterogeneity.

In certain embodiments, the protein is an antibody, and the distribution of lysine variant heterogeneity comprises a distribution of the lysine variants Lys 0, Lys 1 and Lys 2, wherein the Lys 0 lysine variant comprises an antibody with heavy chains that do not comprise a C-terminal lysine, wherein the Lys 1 lysine variant comprises an antibody with one heavy chain that comprises a C-terminal lysine, and wherein the Lys 2 lysine variant comprises an antibody wherein both heavy chains comprise a C-terminal lysine.

In certain embodiments, C-terminal lysine variants are associated with charge heterogeneities present in protein preparations, for example, monoclonal antibody (mAb) preparations, produced through a cell culture process. These heterogeneities can be detected by various methods, such as, for example, WCX-10 HPLC (a weak cation exchange chromatography), or IEF (isoelectric focusing).

In certain embodiments, the heterogeneity arises from subspecies of protein differing by the presence or absence of C-terminal lysines. For example, the population of proteins may comprise more than one subspecies of lysine variant. In one non-limiting example, the lysine variants may comprise at least two of Lys 0, Lys 1 and Lys 2 lysine variants which can be detected by weak cation exchange chromatography of the expression product of a host cell expressing Adalimumab.

In certain embodiments, the heterogeneity arises from the size of subpopulations having different C-terminal lysine profiles. For example, the population of proteins may comprise more than one subspecies of C-terminal lysine variant, and each of the variants may be present in different amounts. In one non-limiting example, the C-terminal lysine variants may be at least two of the Lys 0, Lys 1 and Lys 2 lysine variants detected by weak cation exchange chromatography of the expression product of a host cell expressing Adalimumab. In certain embodiments, Lys 0, Lys 1 or Lys 2 subspecies are present in different amounts.

In certain embodiments, the heterogeneity arises from both a difference in the amount of lysine variants in the population of proteins and the type of lysine variants present in the population of proteins.

As used herein, the terms "acidic species", "acidic region" and "acidic species heterogeneity" refer to a characteristic of a population of proteins wherein the population includes a distribution of product-related impurities identifiable by the presence of charge heterogeneities. For example, in monoclonal antibody (mAb) preparations, such acidic species heterogeneities can be detected by various methods, such as, for example, WCX-10 HPLC (a weak cation exchange chromatography), or IEF (isoelectric focusing). In certain embodiments, the acidic species identified using such techniques comprise a mixture of product-related impurities containing antibody product fragments (e.g., Fc and Fab fragments), and/or post-translation modifications of the antibody product, such as, deamidated and/or glycoslyated antibodies.

In certain embodiments, the acidic species heterogeneity comprises a difference in the type of acidic species present in the population of proteins. For example, the population of proteins may comprise more than one acidic species variant.

In certain embodiments, the heterogeneity of the distribution of acidic species comprises a difference in the amount of acidic species in the population of proteins. For example, the population of proteins may comprise more than one acidic species variant, and each of the variants may be present in different amounts.

5.2. Antibody Generation

The term "antibody" as used in this section refers to an intact antibody or an antigen binding fragment thereof.

The antibodies of the present disclosure can be generated by a variety of techniques, including immunization of an animal with the antigen of interest followed by conventional monoclonal antibody methodologies e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

In certain embodiments, the animal system for preparing hybridomas is the murine system. Hybridoma production is a very well-established procedure. Immunization protocols and techniques for isolation of immunized splenocytes for fusion are known in the art. Fusion partners (e.g., murine myeloma cells) and fusion procedures are also known.

An antibody can be, in certain embodiments, a human, a chimeric, or a humanized antibody. Humanized antibodies of the present disclosure can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

Human monoclonal antibodies can be generated using transgenic or transchromosomic mice carrying parts of the human immune system rather than the mouse system. These transgenic and transchromosomic mice include mice referred to herein as the HuMAb Mouse® (Medarex, Inc.), KM Mouse® (Medarex, Inc.), and XenoMouse® (Amgen).

Moreover, alternative transchromosomic animal systems expressing human immunoglobulin genes are available in the art and can be used to raise antibodies of the disclosure. For example, mice carrying both a human heavy chain transchromosome and a human light chain tranchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (e.g., Kuroiwa et al. (2002) Nature Biotechnology 20:889-894 and PCT application No. WO 2002/092812) and can be used to raise the antibodies of this disclosure.

In certain embodiments, the antibodies of this disclosure are recombinant human antibodies, which can be isolated by screening of a recombinant combinatorial antibody library, e.g., a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia Recombinant Phage Antibody System, catalog no. 27-9400-01; and the Stratagene SurfZAP™ phage display kit, catalog no. 240612, the entire teachings of which are incorporated herein), examples of methods and reagents particularly amenable for use in generating and screening antibody display libraries can be found in, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum Antibod Hybridomas 3:81-85; Huse et al. (1989) Science 246:1275-1281; McCafferty et al., Nature (1990) 348:552-554; Griffiths et al. (1993) EMBO J. 12:725-734; Hawkins et al. (1992) J Mol Biol 226:889-896; Clackson et al. (1991) Nature 352:624-628; Gram et al. (1992) PNAS 89:3576-3580; Garrard et al. (1991) Bio/Technology 9:1373-1377; Hoogenboom et al. (1991) Nuc Acid Res 19:4133-4137; and Barbas et al. (1991) PNAS 88:7978-7982; the entire teachings of which are incorporated herein.

Human monoclonal antibodies of this disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

The antibodies or antigen-binding portions thereof, of this disclosure can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see, e.g., Canfield and Morrison (1991) J. Exp. Med. 173:1483-1491; and Lund et al. (1991) J. of Immunol. 147:2657-2662, the entire teachings of which are incorporated herein). Reduction in FcR binding ability of the antibody may also reduce other effector functions which rely on FcR interactions, such as opsonization and phagocytosis and antigen-dependent cellular cytotoxicity.

5.3. Antibody Production

To express an antibody of the invention, DNAs encoding partial or full-length light and heavy chains are inserted into one or more expression vector such that the genes are operatively linked to transcriptional and translational control sequences. (See, e.g., U.S. Pat. No. 6,914,128, the entire teaching of which is incorporated herein by reference.) In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into a separate vector or, more typically, both genes are inserted into the same expression vector. The antibody genes are inserted into an expression vector by standard methods (e.g., ligation of complementary restriction sites on the antibody gene fragment and vector, or blunt end ligation if no restriction sites are present). Prior to insertion of the antibody or antibody-related light or heavy chain sequences, the expression vector may already carry antibody constant region sequences. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, a recombinant expression vector of the invention can carry one or more regulatory sequence that controls the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, e.g., in Goeddel; Gene Expression Technology: Methods in Enzymology 185, Academic Press, San Diego, Calif. (1990), the entire teaching of which is incorporated herein by reference. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al. and U.S. Pat. No. 4,968,615 by Schaffner et al., the entire teachings of which are incorporated herein by reference.

In addition to the antibody chain genes and regulatory sequences, a recombinant expression vector of the invention may carry one or more additional sequences, such as a sequence that regulates replication of the vector in host cells (e.g., origins of replication) and/or a selectable marker gene. The selectable marker gene facilitates selection of host cells into which the vector has been introduced (see e.g., U.S. Pat. Nos. 4,399,216, 4,634,665 and 5,179,017, all by Axel et al., the entire teachings of which are incorporated herein by reference). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in dhfr-host cells with methotrexate selection/amplification) and the neo gene (for G418 selection).

An antibody of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel et al. (eds.) Current Protocols in Molecular Biology, Greene Publishing Associates, (1989) and in U.S. Pat. Nos. 4,816,397 & 6,914,128, the entire teachings of which are incorporated herein.

For expression of the light and heavy chains, the expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, such as mammalian host cells, is suitable because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss and Wood (1985) Immunology Today 6:12-13, the entire teaching of which is incorporated herein by reference).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, e.g., Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. lichenifonnis* (e.g., *B. licheniformis* 41P disclosed in DD 266,710 published Apr. 12, 1989), *Pseudomonas* such as *P. aeruginosa*, and *Streptomyces*. One suitable *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

Suitable mammalian host cells for expressing the recombinant antibodies of the invention include Chinese Hamster Ovary (CHO cells) (including dhfr-CHO cells, described in Urlaub and Chasin, (1980) PNAS USA 77:4216-4220, used with a DHFR selectable marker, e.g., as described in Kaufman and Sharp (1982) Mol. Biol. 159:601-621, the entire teachings of which are incorporated herein by reference), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Other examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/–DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2), the entire teachings of which are incorporated herein by reference.

Host cells are transformed with the above-described expression or cloning vectors for antibody production and cultured in conventional nutrient media modified as appropriate for inducing promoters, selecting transformants, or amplifying the genes encoding the desired sequences.

The host cells used to produce an antibody may be cultured in a variety of media. Commercially available media such as Ham's F10™ (Sigma), Minimal Essential Medium™ ((MEM), (Sigma), RPMI-1640 (Sigma), and Dulbecco's Modified Eagle's Medium™ ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells, the entire teachings of which are incorporated herein by reference. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Host cells can also be used to produce portions of intact antibodies, such as Fab fragments or scFv molecules. It is understood that variations on the above procedure are within the scope of the present invention. For example, in certain embodiments it may be desirable to transfect a host cell with DNA encoding either the light chain or the heavy chain (but not both) of an antibody of this invention. Recombinant DNA technology may also be used to remove some or the entire DNA encoding either or both of the light and heavy chains that is not necessary for binding to the antigen to which the putative antibody of interest binds. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the one to which the putative antibody of interest binds, depending on the specificity of the antibody of the invention, by crosslinking an antibody of the invention to a second antibody by standard chemical crosslinking methods.

In a suitable system for recombinant expression of an antibody of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

When using recombinant techniques, the antibody can be produced intracellularly, in the periplasmic space, or directly secreted into the medium. In one aspect, if the antibody is produced intracellularly, as a first step, the particulate debris, either host cells or lysed cells (e.g., resulting from homogenization), can be removed, e.g., by centrifugation or ultrafiltration. Where the antibody is secreted into the medium, supernatants from such expression systems can be first concentrated using a commercially available protein concentration filter, e.g., an Amicon™ or Millipore Pellicon™ ultrafiltration unit.

Prior to the process of the invention, procedures for purification of antibodies from cell debris initially depend on the site of expression of the antibody. Some antibodies can be secreted directly from the cell into the surrounding growth media; others are made intraceilularly. For the latter antibodies, the first step of a purification process typically involves: lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. Where the antibody is secreted, supernatants from such expression systems are generally first concentrated using a commercially available protein concentration filter, e.g., an Amicon™ or Millipore Pellicon™ ultrafiltration unit. Where the antibody is secreted into the medium, the recombinant host cells can also be separated from the cell culture medium, e.g., by tangential flow filtration. Antibodies can be further recovered from the culture medium using the antibody purification methods of the invention.

5.4. Antibody Purification 5.4.1. Antibody Purification Generally

In certain embodiments, the invention provides methods and compositions for producing a purified or partially purified (e.g., process-related impurity-reduced and/or product-related substance-modulated) protein preparation from a mixture comprising a protein of interest, e.g., an antibody, and at least one process-related impurity or product-related substance. In certain embodiments, the modulation of product-related substances involves the reduction of certain of such substances, while in other embodiments, such modulation can be to increase certain of such substances. For example, in certain embodiments, it is desired to match the product-related substance profile of a sample to that of a reference sample by the methods described herein.

In certain embodiments, the compositions of the present invention include, but are not limited to, process-related impurity-reduced and/or product-related substance-modulated compositions comprising a protein of interest. For example, but not by way of limitation, the present invention is directed to process-related impurity-reduced and/or product-related substance-modulated compositions comprising Adalimumab. Such process-related impurity-reduced and/or product-related substance-modulated compositions process-related impurity-reduced and/or product-related substance-modulated compositions address the need for improved product characteristics, including, but not limited to, product stability, product safety and product efficacy.

In certain embodiments, the present invention is directed to a method for preparing a process-related impurity-reduced and/or product-related substance-modulated composition comprising a protein of interest wherein a chromatographic separation is performed to identify the particular conditions, e.g., salt concentration, pH, temperature, load amount and conditions, and washing conditions, sufficient to elicit the desired fractionation profile, e.g., fractionation of product-related substances, such as acidic species and lysing variants, of a sample comprising the protein of interest and at least one process-related impurity and/or at least one product-related substance. In certain embodiments, the method will further comprise pooling of the resulting fractions comprising the desired process-related impurity-reduced and/or product-related substance-modulated composition comprising a protein of interest.

In certain embodiments, the purification process of the invention begins at the separation step when the antibody has been produced using production methods described above and/or by alternative production methods conventional in the art. Once a clarified solution or mixture comprising the protein of interest, e.g., an antibody, has been obtained, separation of the protein of interest from process-related impurities, such as the other proteins produced by the cell, as well as product-related substances, such as charge variants and/or size variants (aggregates and fragments) is performed. In certain non-limiting embodiments, such separation is performed using CEX, AEX, and/or MM chromatography. In certain embodiments, a combination of one or more different purification techniques, including affinity separation step(s), ion exchange separation step(s), mixed-mode step(s), and/or hydrophobic interaction separation step(s) can also be employed. Such additional purification steps separate mixtures of proteins on the basis of their charge, degree of hydrophobicity, and/or size. In one aspect of the invention, such additional separation steps are performed using chromatography, including hydrophobic, anionic or cationic interaction (or a combination thereof). Numerous chromatography resins are available for each of these techniques, allowing accurate tailoring of the purification scheme to the particular protein involved. The essence of each of the separation methods is that proteins can either traverse at different rates down a column, achieving a physical separation that increases as they pass further down the column, or to adhere selectively to the separation medium, being then differentially eluted by different solvents. In some cases, the protein of interest is separated from impurities and or product-related substances when the impurities and/or product-related substances specifically adhere to the column and the protein of interest does not, i.e., the protein of interest is washed from the column, while in other cases the protein of interest will adhere to the column, while the impurities and/or product-related substances are washed from the column.

5.4.2. Primary Recovery

In certain embodiments, the initial steps of the purification methods of the present invention involve the clarification and primary recovery of antibody from a sample matrix. In certain embodiments, the primary recovery will include one or more centrifugation steps to separate the antibody product from the cells and cell debris. Centrifugation of the sample can be run at, for example, but not by way of limitation, 7,000×g to approximately 12,750×g. In the context of large scale purification, such centrifugation can occur on-line with a flow rate set to achieve, for example, but not by way of limitation, a turbidity level of 150 NTU in the resulting supernatant. Such supernatant can then be collected for further purification, or in-line filtered through one or more depth filters for further clarification of the sample.

In certain embodiments, the initial steps of the purification methods of the present invention involve the clarification and primary recovery of antibody from a sample matrix. In certain embodiments, the primary recovery will include one or more centrifugation steps to separate the antibody product from the cells and cell debris. Centrifugation of the sample can be run at, for example, but not by way of limitation, 7,000×g to approximately 12,750×g. In the context of large scale purification, such centrifugation can occur on-line with a flow rate set to achieve, for example, but not by way of limitation, a turbidity level of 150 NTU in the resulting supernatant. Such supernatant can then be collected for further purification, or in-line filtered through one or more depth filters for further clarification of the sample, In certain embodiments, the primary recovery will include the use of one or more depth filtration steps to clarify the sample matrix and thereby aid in purifying the antibodies of interest in the present invention. In other embodiments, the primary recovery will include the use of one or more depth filtration steps post centrifugation to further clarify the sample matrix. Non-limiting examples of depth filters that can be used in the context of the instant invention include the Millistak+ X0HC, F0HC, D0HC, A1HC, B1HC depth filters (EMD Millipore), Cuno™ model 30/60ZA, 60/90 ZA, VR05, VR07, delipid depth filters (3M Corp.). A 0.2 μm filter such as Sartorius's 0.45/0.2 μm Sartopore™ bi-layer or Millipore's Express SHR or SHC filter cartridges typically follows the depth filters.

In certain embodiments, the primary recovery process can also be a point at which to reduce or inactivate viruses that can be present in the sample matrix. For example, any one or more of a variety of methods of viral reduction/inactivation can be used during the primary recovery phase of purification including heat inactivation (pasteurization), pH inactivation, solvent/detergent treatment, UV and γ-ray irradiation and the addition of certain chemical inactivating agents such as β-propiolactone or e.g., copper phenanthroline as in U.S. Pat. No. 4,534,972. In certain embodiments of the present invention, the sample matrix is exposed to detergent viral inactivation during the primary recovery phase. In other embodiments, the sample matrix may be exposed to low pH inactivation during the primary recovery phase.

In those embodiments where viral reduction/inactivation is employed, the sample mixture can be adjusted, as needed, for further purification steps. For example, following low pH viral inactivation, the pH of the sample mixture is typically adjusted to a more neutral pH, e.g., from about 4.5 to about 8.5, prior to continuing the purification process. Additionally, the mixture may be diluted with water for injection (WFI) to obtain a desired conductivity.

5.4.3. Protein A Affinity Chromatography

In certain embodiments, particularly where the protein of interest is an antibody, the primary recovery sample is subjected to Protein A affinity chromatography to purify the antibody of interest away from process-related impurities, such as HCPs. There are a variety of commercial sources for Protein A resin. Suitable resins include, but not limited to, MabSelect SuRe™, MabSelect SuRe LX, MabSelect, MabSelect Xtra, rProtein A Sepharose from GE Healthcare, ProSep HC, ProSep Ultra, and ProSep Ultra Plus from EMD Millipore, MapCapture from Life Technologies.

In certain embodiments, the Protein A column can be equilibrated with a suitable buffer prior to sample loading. Following the loading of the column, the column can be washed one or multiple times using a suitable sets of buffers. The Protein A column can then be eluted using an appropriate elution buffer. The eluate can be monitored using techniques well known to those skilled in the art. The eluate fractions of interest can be collected and then prepared for further processing.

The Protein A eluate may subject to a viral inactivation step either by detergent or low pH, provided this step is not performed prior to the Protein A capture operation. A proper detergent concentration or pH and time can be selected to obtain desired viral inactivation results. After viral inactivation, the Protein A eluate is usually pH and/or conductivity adjusted for subsequent purification steps.

The Protein A eluate may be subjected to filtration through a depth filter to remove turbidity and/or various impurities from the antibody of interest prior to additional chromatographic polishing steps. Examples of depth filters include, but not limited to, Millistak+ X0HC, F0HC, D0HC, A1HC, and B1HC Pod filters (EMD Millipore), or Zeta Plus 30ZA/60ZA, 60ZA/90ZA, delipid, VR07, and VR05 filters (3M). The Protein A eluate pool may need to be conditioned to proper pH and conductivity to obtain desired impurity removal and product recovery from the depth filtration step.

5.4.5. Anion Exchange Chromatography

In certain embodiments, the instant invention provides methods for producing a process-related impurity and/or product-related substance-reduced protein preparation from a mixture comprising a protein of interest (i.e., a product) and at least one process-related impurity and/or product-related substance by subjecting the mixture to at least one anion exchange separation step. In certain embodiments, the anion exchange step will occur after the above-described Protein A affinity step.

The use of an anionic exchange material versus a cationic exchange material, such as those cation exchange materials discussed in detail below, is based on the local charges of the protein of interest in a given solution. Therefore, it is within the scope of this invention to employ an anionic exchange step prior to the use of a cationic exchange step, or a cationic exchange step prior to the use of an anionic exchange step. Furthermore, it is within the scope of this invention to employ only an anionic exchange step, only an cationic exchange step, or any serial combination of the two (including serial combinations of one or both ion exchange steps with the other chromatographic separation technologies described herein).

In performing the separation, the initial protein mixture can be contacted with the anion exchange material by using any of a variety of techniques, e.g., using a batch purification technique or a chromatographic technique.

For example, in the context of batch purification, anion exchange material is prepared in, or equilibrated to, the desired starting buffer. Upon preparation, or equilibration, a slurry of the anion exchange material is obtained. The protein of interest, e.g., antibody, solution is contacted with the slurry to allow for protein adsorption to the anion exchange material. The solution comprising the process-related impurities and/or product-related substances that do not bind to the AEX material is separated from the slurry, e.g., by allowing the slurry to settle and removing the supernatant. The slurry can be subjected to one or more washing steps and/or elution steps.

In the context of chromatographic separation, a chromatographic apparatus, commonly cylindrical in shape, is employed to contain the chromatographic support material (e.g., AEX material) prepared in an appropriate buffer solution. The chromatographic apparatus, if cylindrical, can have a diameter of about 5 mm to about 2 meters, and a height of 5 cm to 50 cm, and in certain embodiments, particularly for large scale processing, a height of ≤30 cm is employed. Once the chromatographic material is added to the chromatographic apparatus, a sample containing the protein of interest, e.g., an antibody, is contacted to the chromatographic material to induce the separation. Any portion of the solution that does not bind to the chromatographic material, e.g., which may comprise, depending on the AEX material being employed, the protein of interest, process-related impurities, and/or product-related substances, is separated from the chromatographic material by washing the material and collecting fractions from column. The chromatographic material can be subjected to one or more wash steps. If desired, the chromatographic material can then be contacted with a solution designed to desorb any components of the solution that have bound to the chromatographic material.

In certain embodiments, a wash step can be performed in the context of AEX chromatography using conditions similar to the load conditions or alternatively by decreasing the pH and/or increasing the ionic strength/conductivity of the wash in a step wise or linear gradient manner. The resulting flow through and wash fractions can be analyzed and appropriate fractions pooled to achieve the desired reduction in charged variant species. In certain embodiments, the aqueous salt solution used as both the loading and wash buffer has a pH that at or near the isoelectric point (pI) of the protein of interest. In certain embodiments the pH is about 0 to 2 units higher or lower than the pI of the protein of interest. In certain embodiments, it will be in the range of 0 to 0.5 units higher or lower. In certain embodiments, it will be at the pI of the antibody.

In certain non-limiting embodiments, the anionic agent is selected from the group consisting of acetate, formate, or combinations thereof. In certain non-limiting embodiments, the cationic agent is selected from the group consisting of Tris, arginine, or combinations thereof.

A packed anion-exchange chromatography column, anion-exchange membrane device, anion-exchange monolithic device, or depth filter media can be operated either in bind-elute mode, flow-through mode, or a hybrid mode wherein the product exhibits binding to the chromatographic material, yet can be washed from the column using a buffer that is the same or substantially similar to the loading buffer. In the bind-elute mode, the column or the membrane device is first conditioned with a buffer with appropriate ionic strength and pH under conditions where certain proteins will be immobilized on the resin based matrix. For example, in certain embodiments, during the feed load, the protein of interest will be adsorbed to the resin due to electrostatic attraction. After washing the column or the membrane device with the equilibration buffer or another buffer with different pH and/or conductivity, the product recovery is achieved by increasing the ionic strength (i.e., conductivity) of the elution buffer to compete with the solute for the charged sites of the anion exchange matrix. Changing the pH and thereby altering the charge of the solute is another way to achieve elution of the solute. The change in conductivity or pH may be gradual (gradient elution) or stepwise (step elution). In the flow-through mode, the column or the membrane device is operated at selected pH and conductivity such that the protein of interest does not bind to the resin or the membrane while the process-related impurities and product-related substances will either be retained on the column or will have a distinct elution profile as compared to the protein of interest. In the context of this hybrid strategy, process-related impurities and product-relates substances will bind to the chromatographic material (or flow through) in a manner distinct from the protein of interest, e.g., while the protein of interest and certain aggregates and/or fragments of the protein of interest may bind the chromatographic material, washes that preferentially remove the protein of interest can be applied. The column is then regenerated before next use.

Non-limiting examples of anionic exchange substituents include diethylaminoethyl (DEAE), quaternary aminoethyl (QAE) and quaternary amine (Q) groups. Additional non-limiting examples include: Poros 50PI and Poros 50HQ, which are a rigid polymeric bead with a backbone consisting of cross-linked poly[styrene-divinylbenzene]; Capto Q Impres and Capto DEAE, which are a high flow agarose bead; Toyopearl QAE-550, Toyopearl DEAE-650, and Toyopearl GigaCap Q-650, which are a polymeric base bead; Fractogel® EMD TMAE Hicap, which is a synthetic polymeric resin with a tentacle ion exchanger; Sartobind STIC® PA nano, which is a salt-tolerant chromatographic membrane with a primary amine ligand; Sartobind Q nano; which is a strong anion exchange chromatographic membrane; CUNO BioCap; which is a zeta-plus depth filter media constructed from inorganic filter aids, refined cellulose, and an ion exchange resin; and X0HC, which is a depth-filter media constructed from inorganic filter aid, cellulose, and mixed cellulose esters. The detailed information is listed in Table 1.

TABLE 1

List of AEX Adsorbent Properties

| AEX Adsorbent | Vendor | Media Type | Ligand Type | Particle/Pore Size | Catalog Number |
|---|---|---|---|---|---|
| Poros PI | Applied Biosystems | Resin | Weak | ~50 μm | 1-2459-11 |
| Poros HQ | | | Strong | ~50 μm | 1-2559-11 |
| Capto DEAE | GE | | Weak | ~90 μm | 17-5443-10 |
| CaptoQ Impres | | | Strong | ~90 μm | 17-5316-10 |

TABLE 1-continued

List of AEX Adsorbent Properties

| AEX Adsorbent | Vendor | Media Type | Ligand Type | Particle/Pore Size | Catalog Number |
|---|---|---|---|---|---|
| QAE-550 | Tosoh | | Strong | ~100 μm | 43271 |
| DEAE-650 | | | Weak | ~65 μm | 43201 |
| GigaCap Q-650 | | | Strong | ~75 μm | 21854 |
| TMAE HiCap | EMD/Millipore | | Strong | ~40-90 μm | 1.16881.0013 |
| Sartobind STIC ® PA Nano | Sartorius | Membrane | Weak | 3-5 μm | 92STPA42DN-11-A |
| Sartobind Q Nano | | | Strong | 3-5 μm | 92IEXQ42DN-11 |
| CUNO BioCap 25 | 3M | Depth Filter | NA | NA | BC0025L60ZA05A |
| X0HC | Millipore | | NA | NA | MX0HC23CL3 |

In certain embodiments, the protein load of the mixture comprising protein of interest is adjusted to a total protein load to the column of between about 50 and 500 g/L, or between about 75 and 350 g/L, or between about 200 and 300 g/L. In certain embodiments, the protein concentration of the load protein mixture is adjusted to a protein concentration of the material loaded to the column of about 0.5 and 50 g/L, between about 1 and 20 g/L, or between 3 and 10 g/L, In certain embodiments, additives such as poly ethylene glycol, detergents, amino acids, sugars, chaotropic agents can be added to enhance the performance of the separation, so as to achieve better recovery or product quality.

In certain embodiments, including, but not limited to those relating to Adalimumab, the methods of the instant invention can be used to selectively remove, significantly reduce, or essentially remove all of AR charge variants in the flow through and wash fractions while enriching for the same in the flow elution fraction, thereby producing protein preparations with reduced or free of AR variants. In certain embodiments relating to the purification of Adalimumab, the methods of the instant invention can be used to selectively remove, significantly reduce, or essentially remove all of AR1 charge variants in the flow through and wash fractions while enriching for the same in the flow elution fraction, thereby producing protein preparations with reduced or free of AR1 variants. In certain embodiments relating to Adalimumab, the methods of the instant invention can be used to selectively remove, significantly reduce, or essentially remove all of AR2 charge variants in the flow-through and wash fractions while enriching for the same in the flow elution fraction, thereby producing protein preparations with reduced or free of AR2 variants.

In certain embodiments, including but not limited to those relating to Adalimiumab, the methods of the instant invention can be used to selectively remove, significantly reduce, or essentially remove all of the methylglyoxal (MGO) variants in the flow through and wash fractions while enriching for the same in the elution fraction, thereby producing protein preparations with reduced or free of MGO variants (for example, see U.S. patent application Ser. No. 14/078,181). In certain embodiments, including, but not limited to those relating to Adalimumab, the methods of the instant invention can be used to selectively remove, significantly reduce, or essentially remove all of the glycated variants (schiff's base and permanently glycated forms) in the flow through and wash fractions while enriching for the same in the elution fraction, thereby producing protein preparations with reduced or free of glycated variants.

In certain embodiments, the loading, pH, conductivity of the AEX chromatography step, as well as elution pH conductivity, can be modified to achieve a desired distribution of process-related impurities and/or product-relates substances.

For example, but not by way of limitation, certain embodiments are directed to the modulation of the lysine distribution of purified sample of a protein of interest, e.g., increasing Lys0 and decreasing Lys1 and Lys2. In certain embodiments, the methods of the present invention allow for the preparation of samples wherein the amount of Lys0 is decreased, while the amount of Lys1 and/or Lys2 is increased.

In certain embodiments, an AEX chromatographic separation can be performed and combinations of fractions can be pooled to achieve a combination of desired process-related impurity and/or product-relates substance levels, in addition to, or in place of merely modulating charge variant concentration.

In certain embodiments, spectroscopy methods such as UV, NIR, FTIR, Fluorescence, Raman may be used to monitor levels of product-related charge variants, aggregates, low molecular weight variants (e.g., fragments of the protein of interest) in an on-line, at-line or in-line mode, which can then be used to control the level of charge variants, e.g., acidic species, in the pooled material collected from the AEX effluent. In certain embodiments, specific signals arising from the chemical modification of the proteins such as glycation, MGO modification, deamidation, glycosylation may be specifically measurable by spectroscopic methods through such in-line, on-line or at-line methods, enabling realtime or near-real time control of product quality of the resulting product. In certain embodiments, on-line, at-line or in-line monitoring methods can be used either on the effluent line of the chromatography step or in the collection vessel, to enable achievement of the desired product quality/recovery. In certain embodiments, the UV signal can be used as a surrogate to achieve an appropriate product quality/recovery, wherein the UV signal can be processed appropriately, including, but not limited to, such processing techniques as integration, differentiation, moving average, such that normal process variability can be addressed and the target product quality can be achieved. In certain embodiments, such measurements can be combined with in-line dilution methods such that ion concentration/conductivity of the load/wash can be controlled by feedback and hence facilitate product quality control.

In certain embodiments, a combination of AEX and CEX and MM methods can be used to prepare product-related substance-modulated materials, including certain embodiments where one technology is used in a complementary/supplementary manner with another technology. In certain embodiments, such a combination can be performed such that certain sub-species are removed predominantly by one technology, such that the combination provides the desired final composition/product quality. In certain embodiments, such combinations include the use of additional intervening chromatography, filtration, pH adjustment, UF/DF steps so as to achieve the desired product quality, ion concentration, and/or viral reduction.

5.4.6. Cation Exchange Chromatography

In certain embodiments, the instant invention provides methods for producing a process-related impurity and/or product-related substance-reduced protein preparation from a mixture comprising a protein of interest (i.e., a product) and at least one process-related impurity and/or product-related substance by subjecting the mixture to at least one cation exchange separation step. In certain embodiments, the CEX step will occur after the above-described Protein A affinity step.

The use of a cationic exchange material versus a anionic exchange material, such as those anionic exchange materials discussed in detail above, is based on the local charges of the protein of interest in a given solution. Therefore, it is within the scope of this invention to employ a cationic exchange step prior to the use of an anionic exchange step, or an anionic exchange step prior to the use of a cationic exchange step. Furthermore, it is within the scope of this invention to employ only a cationic exchange step, only an anionic exchange step, or any serial combination of the two (including serial combinations of one or both ion exchange steps with the other chromatographic separation technologies described herein).

In performing the separation, the initial protein mixture can be contacted with the cation exchange material by using any of a variety of techniques, e.g., using a batch purification technique or a chromatographic technique, as described above in connection with Protein A or AEX.

In certain embodiments, the aqueous salt solution used as both the loading and wash buffer has a pH that is lower than the isoelectric point (pI) of the protein of interest. In certain embodiments, the pH is about 0 to 5 units lower than the pI of the protein. In certain embodiments, it is in the range of 1 to 2 units lower. In certain embodiments, it is in the range of 1 to 1.5 units lower.

In certain embodiments, the concentration of the anionic agent in aqueous salt solution is increased or decreased to achieve a pH of between about 3.5 and 10.5, or between about 4 and 10, or between about 4.5 and 9.5, or between about 5 and 9, or between about 5.5 and 8.5, or between about 6 and 8, or between about 6.5 and 7.5. In certain embodiments, the concentration of anionic agent is increased or decreased in the aqueous salt solution to achieve a pH of 5, or 5.5, or 6, or 6.5, or 6.8, or 7.5.

In certain embodiments, the conductivity and pH of the aqueous salt solution is adjusted by increasing or decreasing the concentration of a cationic agent. In certain embodiments, the cationic agent is maintained at a concentration of between about range of 20 mM to 500 mM, or between about 50 to 350 mM or between about 100 to 300 mM or between about 100 to 200 mM.

In certain non-limiting embodiments, the cationic agent is selected from the group consisting of sodium, Tris, tromethalmine, ammonium, arginine, or combinations thereof. In certain non-limiting embodiments, the anionic agent is selected from the group consisting of acetate, citrate, chloride anion, sulphate, phosphate or combinations thereof.

A packed cation-exchange chromatography column or a cation-exchange membrane device can be operated either in bind-elute mode, flow-through mode, or a hybrid mode wherein the product exhibits binding to the chromatographic material, yet can be washed from the column using a buffer that is the same or substantially similar to the loading buffer. The details of these modes are outlined above.

Cationic substituents include carboxymethyl (CM), sulfoethyl (SE), sulfopropyl (SP), phosphate (P) and sulfonate (S). Additional cationic materials include, but are not limited to: Capto SP ImpRes, which is a high flow agarose bead; CM Hyper D grade F; which is a ceramic bead coated and permeated with a functionalized hydrogel, 250-400 ionic groups μeq/mL; Eshmuno S, which is a hydrophilic polyvinyl ether base matrix with 50-100 μeq/mL ionic capacity; Nuvia C Prime, which is a hydrophobic cation exchange media composed of a macroporous highly crosslinked hydrophilic polymer matrix 55-75 μeq/mL; Nuvia S, which has a UNOsphere base matrix with 90-150 μeq/mL ionic groups; Poros HS; which is a rigid polymetic bead with a backbone consisting of cross-linked poly[styrene-divinylbenzene]; Poros XS; which is a rigid polymetic bead with a backbone consisting of cross-linked poly[styrene-divinylbenzene]; Toyo Pearl Giga Cap CM 650M, which is a polymeric base bead with 0.225 meq/mL ionic capacity; Toyo Pearl Giga Cap S 650M which is a polymeric base bead; Toyo Pearl MX TRP, which is a polymeric base bead. Detailed information concerning the aforementioned materials is listed in Table 2.

TABLE 2

Cationic Materials

| Resin | Vendor | type | particle size | Catalog Number |
|---|---|---|---|---|
| Capto SP ImpRes | GE | Strong | ~40 μm | 17-5468-10 |
| CM Hyper D | Pail | Weak | ~50 μm | 20050-027 |
| Eshmuno S | Millipore | Strong | ~85 μm | 1.20078 |
| Nuvia C Prime | Biorad | Mix Mode | ~70 μm | 156-3401 |
| Nuvia S | Biorad | Strong | ~85 μm | 156-0315 |
| Poros HS | Applied Biosystems | Weak | ~50 μm | 13359-06 |
| Poros XS | Applied Biosystems | Strong | ~50 μm | 4404337 |
| Toyo Pearl Giga Cap CM 650M | Tosoh | Weak | ~75 μm | 21946 |
| Toyo Pearl Giga Cap S 650M | Tosoh | Strong | ~75 μm | 21833 |
| Toyo Pearl MX Trp 650M | Tosoh | Mix Mode | ~75 μm | 22817 |

In certain embodiments, the protein load of the mixture comprising protein of interest is adjusted to a total protein load to the column of between about 5 and 150 g/L, or between about 10 and 100 g/L, between about 20 and 80 g/L, or between about 30 and 50 g/L. In certain embodiments, the protein concentration of the load protein mixture is adjusted to a protein concentration of the material loaded to the column of about 0.5 and 50 g/L, or between about 1 and 20 g/L.

In certain embodiments, additives such as poly ethylene glycol, detergents, amino acids, sugars, chaotropic agents can be added to enhance the performance of the separation, so as to achieve better recovery or product quality.

In certain embodiments, including, but not limited to those relating to Adalimumab, the methods of the instant invention can be used to selectively remove, significantly reduce, or essentially remove all of AR charge variants in the elution fractions while enriching for the same in the flow through and wash fractions, thereby producing protein preparations with reduced or free of AR variants. In certain embodiments relating to the purification of Adalimumab, the methods of the instant invention can be used to selectively remove, significantly reduce, or essentially remove all of AR1 charge variants in the elution fractions while enriching for the same in the flow through and wash fractions, thereby producing protein preparations with reduced or free of AR1 variants. In certain embodiments relating to the purification of Adalimumab, the methods of the instant invention can be used to selectively remove, significantly reduce, or essentially remove all of AR2 charge variants in the elution fractions while enriching for the same in the flow through and wash fractions, thereby producing protein preparations with reduced or free of AR2 variants.

In certain embodiments, including, but not limited to those relating to Adalimumab, the methods of the instant invention can be used to selectively remove, significantly reduce, or essentially remove all of the Methyl Glycoxol (MGO) variants in the elution fractions while enriching for the same in the flow through and wash fractions, thereby producing protein preparations with reduced or free of MGO variants. In certain embodiments, including, but not limited to those relating to Adalimumab, the methods of the instant invention can be used to selectively remove, significantly reduce, or essentially remove all of the glycated variants (schiffs base and permanently glycated forms) in the elution fractions while enriching for the same in the flow through and wash fractions, thereby producing protein preparations with reduced or free of glycated variants.

In certain embodiments, the loading, pH, conductivity of the CEX chromatography step, as well as elution pH conductivity, can be modified to achieve a desired distribution of process-related impurities and/or product-relates substances. For example, but not by way of limitation, certain embodiments are directed to the modulation of the lysine distribution of a purified sample of a protein of interest, e.g., increasing Lys0 and decreasing Lys1 and Lys2. In certain embodiments, the methods of the present invention allow for the preparation of samples wherein the amount of Lys0 is decreased, while the amount of Lys1 and/or Lys2 is increased.

In certain embodiments, a CEX chromatographic separation can be performed and combinations of fractions can be pooled to achieve a combination of desired process-related impurity and/or product-relates substance levels, in addition to, or in place of merely modulating charge variant concentration.

In certain embodiments, spectroscopy methods such as UV, NIR, FTIR, Fluorescence, Raman may be used to monitor levels of product-related charge variants, aggregates, low molecular weight variants (e.g., fragments of the protein of interest) in an on-line, at-line or in-line mode, which can then be used to control the level of charge variants, e.g., acidic species, in the pooled material collected from the CEX effluent. In certain embodiments, specific signals arising from the chemical modification of the proteins such as glycation, MGO modification, deamidation, glycosylation may be specifically measurable by spectroscopic methods through such in-line, on-line or at-line methods, enabling realtime or near-real time control of product quality of the resulting product. In certain embodiments, on-line, at-line or in-line monitoring methods can be used either on the effluent line of the chromatography step or in the collection vessel, to enable achievement of the desired product quality/recovery. In certain embodiments, the UV signal can be used as a surrogate to achieve an appropriate product quality/recovery, wherein the UV signal can be processed appropriately, including, but not limited to, such processing techniques as integration, differentiation, moving average, such that normal process variability can be addressed and the target product quality can be achieved. In certain embodiments, such measurements can be combined with in-line dilution methods such that ion concentration/conductivity of the load/wash can be controlled by feedback and hence facilitate product quality control.

In certain embodiments, a combination of CEX and AEX and MM methods can be used to prepare product-related substance-modulated materials, including certain embodiments where one technology is used in a complementary/supplementary manner with another technology. In certain embodiments, such a combination can be performed such that certain sub-species are removed predominantly by one technology, such that the combination provides the desired final composition/product quality. In certain embodiments, such combinations include the use of additional intervening chromatography, filtration, pH adjustment, UF/DF steps so as to achieve the desired product quality, ion concentration, and/or viral reduction.

5.4.7. Mixed Mode Chromatography

Mixed mode ("MM") chromatography, also referred to herein as "multimodal chromatography", is a chromatographic strategy that utilizes a support comprising a ligand that is capable of providing at least two different, in certain embodiments co-operative, sites that interact with the substance to be bound. In certain embodiments, one of these sites gives an attractive type of charge-charge interaction between the ligand and the substance of interest and the other site provides for electron acceptor-donor interaction and/or hydrophobic and/or hydrophilic interactions. Electron donor-acceptor interactions include interactions such as hydrogen-bonding, $\pi$-$\pi$, cation-$\pi$, charge transfer, dipole-dipole, induced dipole etc.

In certain embodiments, the resin employed for a mixed mode separation is Capto Adhere. Capto Adhere is a strong anion exchanger with multimodal functionality. Its base matrix is a highly cross-linked agarose with a ligand (N-Benzyl-N-methyl ethanol amine) that exhibits many functionalities for interaction, such as ionic interaction, hydrogen bonding and hydrophobic interaction. In certain embodiments, the resin employed for a mixed mode separation is selected from PPA-HyperCel and HEA-HyperCel. The base matrices of PPA-HyperCel and HEA-HyperCel are high porosity cross-linked cellulose. Their ligands are Phenylpropylamine and Hexylamine, respectively. Phenylpropylamine and Hexylamine offer different selectivity and hydrophobicity options for protein separations. Additional mixed mode chromatographic supports include, but are not limited to, Nuvia C Prime, Toyo Pearl MX Trp 650M, and Eshmuno® HCX.

In certain embodiments, the mixed mode chromatography resin is comprised of ligands coupled to an organic or inorganic support, sometimes denoted a base matrix, directly or via a spacer. The support may be in the form of particles, such as essentially spherical particles, a monolith, filter, membrane, surface, capillaries, etc. In certain embodiments, the support is prepared from a native polymer, such as cross-linked carbohydrate material, such as agarose, agar, cellulose, dextran, chitosan, konjac, carrageenan, gellan, alginate etc. To obtain high adsorption capacities, the support can be porous, and ligands are then coupled to the external surfaces as well as to the pore surfaces. Such native polymer supports can be prepared according to standard methods, such as inverse suspension gelation (S Hjerten: Biochim Biophys Acta 79(2), 393-398 (1964). Alternatively, the support can be prepared from a synthetic polymer, such as cross-linked synthetic polymers, e.g. styrene or styrene derivatives, divinylbenzene, acrylamides, acrylate esters, methacrylate esters, vinyl esters, vinyl amides etc. Such synthetic polymers can be produced according to standard methods, see e.g. "Styrene based polymer supports developed by suspension polymerization" (R Arshady: Chimica e L'Industria 70(9), 70-75 (1988)). Porous native or synthetic polymer supports are also available from commercial sources, such as Amersham Biosciences, Uppsala, Sweden.

In certain embodiments, the protein load of the mixture comprising protein of interest is adjusted to a total protein load to the column of between about 50 and 750 g/L, or between about 75 and 500 g/L, or between about 100 and 300 g/L. In certain embodiments, the protein concentration of the load protein mixture is adjusted to a protein concentration of the material loaded to the column of about 1 and 50 g/L, or between about 9 and 25 g/L.

In certain embodiments, additives such as poly ethylene glycol, detergents, amino acids, sugars, chaotropic agents can be added to enhance the performance of the separation, so as to achieve better recovery or product quality.

In certain embodiments, including, but not limited to those relating to Adalimumab, the methods of the instant invention can be used to selectively remove, significantly reduce, or essentially remove all of AR charge variants in the flow through and wash fractions while enriching for the same in the flow elution fraction, thereby producing protein preparations with reduced or free of AR variants. In certain embodiments relating to Adalimumab, the methods of the instant invention can be used to selectively remove, significantly reduce, or essentially remove all of AR1 charge variants in the flow through and wash fractions while enriching for the same in the flow elution fraction, thereby producing protein preparations with reduced or free of AR1 variants. In certain embodiments relating to Adalimumab, the methods of the instant invention can be used to selectively remove, significantly reduce, or essentially remove all of AR2 charge variants in the flow-through and wash fractions while enriching for the same in the flow elution fraction, thereby producing protein preparations with reduced or free of AR2 variants.

In certain embodiments, including, but not limited to those relating to Adalimumab, the methods of the instant invention can be used to selectively remove, significantly reduce, or essentially remove all of the methylglyoxal (MGO) variants in the flow through and wash fractions while enriching for the same in the elution fraction, thereby producing protein preparations with reduced or free of MGO variants. In certain embodiments, including, but not limited to those relating to Adalimumab, the methods of the instant invention can be used to selectively remove, significantly reduce, or essentially remove all of the glycated variants (schiff's base and permanently glycated forms) in the flow through and wash fractions while enriching for the same in the elution fraction, thereby producing protein preparations with reduced or free of glycated variants.

In certain embodiments, the loading, pH, conductivity of the MM chromatography step, wash pH and conductivity, as well as elution pH conductivity, can be modified to achieve a desired distribution of process-related impurities and/or product-relates substances. For example, but not by way of limitation, certain embodiments are directed to the modulation of the lysine distribution of a purified sample of a protein of interest, e.g., increasing Lys0 and decreasing Lys1 and Lys2. In certain embodiments, the methods of the present invention allow for the preparation of samples wherein the amount of Lys0 is decreased, while the amount of Lys1 and/or Lys2 is increased.

In certain embodiments, a MM chromatographic separation can be performed and combinations of fractions can be pooled to achieve a combination of desired process-related impurity and/or product-relates substance levels, in addition to, or in place of merely modulating charge variant concentration.

In certain embodiments, spectroscopy methods such as UV, NIR, FTIR, Fluorescence, Raman may be used to monitor levels of product-related charge variants, aggregates, low molecular weight variants (e.g., fragments of the protein of interest) in an on-line, at-line or in-line mode, which can then be used to control the level of charge variants, e.g., acidic species, in the pooled material collected from the MM effluent. In certain embodiments, specific signals arising from the chemical modification of the proteins such as glycation, MGO modification, deamidation, glycosylation may be specifically measurable by spectroscopic methods through such in-line, on-line or at-line methods, enabling realtime or near-real time control of product quality of the resulting product. In certain embodiments, on-line, at-line or in-line monitoring methods can be used either on the effluent line of the chromatography step or in the collection vessel, to enable achievement of the desired product quality/recovery. In certain embodiments, the UV signal can be used as a surrogate to achieve an appropriate product quality/recovery, wherein the UV signal can be processed appropriately, including, but not limited to, such processing techniques as integration, differentiation, moving average, such that normal process variability can be addressed and the target product quality can be achieved. In certain embodiments, such measurements can be combined with in-line dilution methods such that ion concentration/conductivity of the load/wash can be controlled by feedback and hence facilitate product quality control In certain embodiments, a combination of mixed mode and AEX and CEX methods can be used to prepare product-related charge variant-reduced materials, including certain embodiments where one technology is used in a complementary/supplementary manner with another technology. In certain embodiments, such a combination can be performed such that certain sub-species are removed predominantly by one technology, such that the combination provides the desired final composition/product quality. In certain embodiments, such combinations include the use of additional intervening chromatography, filtration, pH adjustment, UF/DF steps so as to achieve the desired product quality, ion concentration, and/or viral reduction.

5.4.8. Hydrophobic Interaction Chromatography

The present invention also features methods for producing a process-related impurity and/or product-related substance-reduced protein preparation from a mixture comprising a protein of interest, e.g., an antibody, and at least one process-related impurity and/or product-related substance further comprising a hydrophobic interaction chromatography (HIC) step in addition to the displacement chromatography step.

In performing the separation, the sample mixture is contacted with the HIC material, e.g., using a batch purification technique or using a column or membrane chromatography. Prior to HIC purification it may be desirable to adjust the concentration of the salt buffer to achieve desired protein binding to the resin or the membrane.

Whereas ion exchange chromatography relies on the local charge of the protein of interest for selective separation, hydrophobic interaction chromatography employs the hydrophobic properties of the proteins to achieve selective separation. Hydrophobic groups on the protein interact with hydrophobic groups of the resin or the membrane. The more hydrophobic a protein is the stronger it will interact with the column or the membrane. Thus the HIC step removes process-related impurities (e.g., HCPs) as well as product-related substances (e.g., aggregates and fragments).

Like ion exchange chromatography, a HIC column or membrane device can also be operated in product a bind-elute mode, a flow-through, or a hybrid mode wherein the product exhibits binding to the chromatographic material, yet can be washed from the column using a buffer that is the same or substantially similar to the loading buffer. The details of these modes are outlined above in connection with AEX purification.

As hydrophobic interactions are strongest at high ionic strength, this form of separation is conveniently performed following salt elution step, such as those that are typically used in connection with ion exchange chromatography. Alternatively, salts can be added into a low salt level feed stream before this step. Adsorption of the antibody to a HIC column is favored by high salt concentrations, but the actual concentrations can vary over a wide range depending on the nature of the protein of interest, salt type and the particular HIC ligand chosen. Various ions can be arranged in a so-called soluphobic series depending on whether they promote hydrophobic interactions (salting-out effects) or disrupt the structure of water (chaotropic effect) and lead to the weakening of the hydrophobic interaction. Cations are ranked in terms of increasing salting out effect as $Ba^{2+}$; $Ca^{2+}$; $Mg^{2+}$; $Li^+$; $Cs^+$; $Na^+$; $K^+$; $Rb^+$; $NH_4^+$, while anions may be ranked in terms of increasing chaotropic effect as $PO_4^{3-}$; $SO_4^{2-}$; $CH_3CO_3^-$; $Cl^-$; $Br^-$; $NO_3^-$; $ClO_4^-$; $I^-$; $SCN^-$.

In general, $Na^+$, $K^+$ or $NH_4^+$ sulfates effectively promote ligand-protein interaction in HIC. Salts may be formulated that influence the strength of the interaction as given by the following relationship: $(NH_4)_2SO_4 > Na_2SO_4 > NaCl > NH_4Cl > NaBr > NaSCN$. In general, salt concentrations of between about 0.75 M and about 2 M ammonium sulfate or between about 1 and 4 M NaCl are useful.

HIC media normally comprise a base matrix (e.g., cross-linked agarose or synthetic copolymer material) to which hydrophobic ligands (e.g., alkyl or aryl groups) are coupled. A suitable HIC media comprises an agarose resin or a membrane functionalized with phenyl groups (e.g., a Phenyl Sepharose™ from GE Healthcare or a Phenyl Membrane from Sartorius). Many HIC resins are available commercially. Examples include, but are not limited to, Capto Phenyl, Phenyl Sepharose™ 6 Fast Flow with low or high substitution, Phenyl Sepharose™ High Performance, Octyl Sepharose™ High Performance (GE Healthcare); Fractogel™ EMD Propyl or Fractogel™ EMD Phenyl (E. Merck, Germany); Macro-Prep™ Methyl or Macro-Prep™ t-Butyl columns (Bio-Rad, California); WP HI-Propyl (C3)™ (J. T. Baker, New Jersey); and Toyopearl™ ether, phenyl or butyl (TosoHaas, PA).

5.4.9. Viral Filt Ration

Viral filtration is a dedicated viral reduction step in the entire purification process. This step is usually performed post chromatographic polishing steps. Viral reduction can be achieved via the use of suitable filters including, but not limited to, Planova 20N™, 50 N or BioEx from Asahi Kasei Pharma, Viresolve™ filters from EMD Millipore, ViroSart CPV from Sartorius, or Ultipor DV20 or DV50™ filter from Pall Corporation. It will be apparent to one of ordinary skill in the art to select a suitable filter to obtain desired filtration performance.

5.4.10. Ultrafiltration/Diafiltration

Certain embodiments of the present invention employ ultrafiltration and diafiltration steps to further concentrate and formulate the protein of interest, e.g., an antibody product. Ultrafiltration is described in detail in: Microfiltration and Ultrafiltration: Principles and Applications, L. Zeman and A. Zydney (Marcel Dekker, Inc., New York, N.Y., 1996); and in: Ultrafiltration Handbook, Munir Cheryan (Technomic Publishing, 1986; ISBN No. 87762-456-9). One filtration process is Tangential Flow Filtration as described in the Millipore catalogue entitled "Pharmaceutical Process Filtration Catalogue" pp. 177-202 (Bedford, Mass., 1995/96). Ultrafiltration is generally considered to mean filtration using filters with a pore size of smaller than 0.1 µm. By employing filters having such small pore size, the volume of the sample can be reduced through permeation of the sample buffer through the filter membrane pores while proteins, such as antibodies, are retained above the membrane surface.

Diafiltration is a method of using membrane filters to remove and exchange salts, sugars, and non-aqueous solvents, to separate free from bound species, to remove low molecular-weight species, and/or to cause the rapid change of ionic and/or pH environments. Microsolutes are removed most efficiently by adding solvent to the solution being diafiltered at a rate approximately equal to the permeate flow rate. This washes away microspecies from the solution at a constant volume, effectively purifying the retained protein of interest. In certain embodiments of the present invention, a diafiltration step is employed to exchange the various buffers used in connection with the instant invention, optionally prior to further chromatography or other purification steps, as well as to remove impurities from the protein preparations.

One of ordinary skill in the art can select appropriate membrane filter device for the UF/DF operation. Examples of membrane cassettes suitable for the present invention include, but not limited to, Pellicon 2 or Pellicon 3 cassetts with 10 kD, 30 kD or 50 kD membranes from EMD Millipore, Kvick 10 kD, 30 kD or 50 kD membrane cassettes from GE Healthcare, and Centramate or Centrasette 10 kD, 30 kD or 50 kD cassettes from Pall Corporation.

5.4.11. Exemplary Purification Strategies

In certain embodiments, primary recovery can proceed by sequentially employing pH reduction, centrifugation, and filtration steps to remove cells and cell debris (including HCPs) from the production bioreactor harvest. In certain embodiments, the present invention is directed to subjecting a sample mixture from said primary recovery to one or more AEX, CEX, and/or MM purification steps. Certain embodiments of the present invention will include further purification steps. Examples of additional purification procedures which can be performed prior to, during, or following the ion exchange chromatography method include ethanol precipitation, isoelectric focusing, reverse phase HPLC, chromatography on silica, chromatography on heparin Sepharose™, further anion exchange chromatography and/or further cation exchange chromatography, chromatofocusing, SDS-PAGE, ammonium sulfate precipitation, hydroxylapatite chromatography, gel electrophoresis, dialysis, and affinity chromatography (e.g., using protein G, an antibody, a specific substrate, ligand or antigen as the capture reagent).

Specific examples of such combinations of strategies is presented below, with specific data relating to particular combinations useful in the context of the instant invention included in Tables 44-51 and 72-74.

In certain embodiments the unbound flow through and wash fractions can be further fractionated and a combination of fractions providing a target product purity can be pooled.

In certain embodiments the protein concentration can be adjusted to achieve a differential partitioning behavior between the antibody product and the product-related substances such that the purity and/or yield can be further improved. In certain embodiments the loading can be performed at different protein concentrations during the loading operation to improve the product quality/yield of any particular purification step.

In certain embodiments the column temperature, can be independently varied to improve the separation efficiency and/or yield of any particular purification step.

In certain embodiments, the loading and washing buffer matrices can be different or composed of mixtures of chemicals, while achieving similar "resin interaction" behavior such that the above novel separation can be effected. For example, but not by way of limitation, the loading and washing buffers can be different, in terms of ionic strength or pH, while remaining substantially similar in function in terms of the washout of the product achieved during the wash step. In certain embodiments, additives such as amino acids, sugars, PEG, etc can be added to the load or wash steps to modulate the partitioning behavior to achieve the separation efficiency and/or yield.

In certain embodiments, the loading & washing steps can be controlled by in-line, at-line or off-line measurement of the product related impurity/substance levels, either in the column effluent, or the collected pool or both, so as to achieve the target product quality and/or yield. In certain embodiments, the loading concentration can be dynamically controlled by in-line or batch or continuous dilutions with buffers or other solutions to achieve the partitioning necessary to improve the separation efficiency and/or yield.

5.5. Methods of Assaying Sample Purity

5.5.1. Assaying Host Cell Protein

The present invention also provides methods for determining the residual levels of host cell protein (HCP) concentration in the isolated/purified antibody composition. As described above, HCPs are desirably excluded from the final target substance product. Exemplary HCPs include proteins originating from the source of the antibody production. Failure to identify and sufficiently remove HCPs from the target antibody may lead to reduced efficacy and/or adverse subject reactions.

As used herein, the term "HCP ELISA" refers to an ELISA where the second antibody used in the assay is specific to the HCPs produced from cells, e.g., CHO cells, used to generate the antibody of interest. The second antibody may be produced according to conventional methods known to those of skill in the art. For example, the second antibody may be produced using HCPs obtained by sham production and purification runs, i.e., the same cell line used to produce the antibody of interest is used, but the cell line is not transfected with antibody DNA. In an exemplary embodiment, the second antibody is produced using HCPs similar to those expressed in the cell expression system of choice, i.e., the cell expression system used to produce the target antibody.

Generally, HCP ELISA comprises sandwiching a liquid sample comprising HCPs between two layers of antibodies, i.e., a first antibody and a second antibody. The sample is incubated during which time the HCPs in the sample are captured by the first antibody, for example, but not limited to goat anti-CHO, affinity purified (Cygnus). A labeled second antibody, or blend of antibodies, specific to the HCPs produced from the cells used to generate the antibody, e.g., anti-CHO HCP Biotinylated, is added, and binds to the HCPs within the sample. In certain embodiments the first and second antibodies are polyclonal antibodies. In certain aspects the first and second antibodies are blends of polyclonal antibodies raised against HCPs. The amount of HCP contained in the sample is determined using the appropriate test based on the label of the second antibody.

HCP ELISA may be used for determining the level of HCPs in an antibody composition, such as an eluate or flow-through obtained using the process described above. The present invention also provides a composition comprising an antibody, wherein the composition has no detectable level of HCPs as determined by an HCP Enzyme Linked Immunosorbent Assay ("ELISA").

5.5.2. Assaying Charge Variants and Aggregates

In certain embodiments, the levels of acidic species and other charge variants in the chromatographic samples produced using the techniques described herein are analyzed. In certain embodiments a CEX-HPLC method is employed. For example, but not by way of limitation, cation exchange chromatography can be performed on a Dionex ProPac WCX-10, Analytical column 4 mm×250 mm (Dionex, Calif.). An Agilent 1200 HPLC system can then be used as the HPLC. In certain embodiments, mobile phases such as 10 mM Sodium Phosphate dibasic pH 7.5 (Mobile phase A) and 10 mM Sodium Phosphate dibasic, 500 mM Sodium Chloride pH 5.5 (Mobile phase B) can be used. In certain embodiments, a binary gradient (94% A, 6% B: 0-20 min; 84% A, 16% B: 20-22 min; 0% A, 100% B: 22-28 min; 94% A, 6% B: 28-34 min) can be used with detection at 280 nm. In certain embodiments, quantitation is based on the relative area percent of detected peaks. In certain embodiments, the peaks that elute at relative residence time less than a certain time are together represented as the acidic peaks.

In certain embodiments, the levels of aggregates, monomer, and fragments in the chromatographic samples produced using the techniques described herein are analyzed. In certain embodiments, the aggregates, monomer, and fragments are measured using a size exclusion chromatographic (SEC) method for each molecule. For example, but not by way of limitation, a TSK-gel G3000SWxL, 5 μm, 125 Å, 7.8×300 mm column (Tosoh Bioscience) can be used in connection with certain embodiments, while a TSK-gel Super SW3000, 4 μm, 250 Å, 4.6×300 mm column (Tosoh Bioscience) can be used in alternative embodiments. In certain embodiments, the aforementioned columns are used along with an Agilent or a Shimazhu HPLC system. In certain embodiments, sample injections are made under isocratic elution conditions using a mobile phase consisting of, for example, 100 mM sodium sulfate and 100 mM sodium phosphate at pH 6.8, and detected with UV absorbance at 214 nm. In certain embodiments, the mobile phase will consist of 1×PBS at pH 7.4, and elution profile detected with UV absorbance at 280 nm. In certain embodiments, quantification is based on the relative area of detected peaks.

5.6. Further Modifications

The purified proteins, e.g., antibodies and antibody-binding portions thereof, of the present invention can be modified. In some embodiments, the antibodies are chemically modified to provide a desired effect. For example, but not by way of limitation, pegylation of antibodies or antibody fragments of the invention may be carried out by any of the pegylation reactions known in the art, as described, e.g., in the following references: Focus on Growth Factors 3:4-10 (1992); EP 0 154 316; and EP 0 401 384, each of which is incorporated by reference herein in its entirety. In one aspect, the pegylation is carried out via an acylation reaction or an alkylation reaction with a reactive polyethylene glycol molecule (or an analogous reactive water-soluble polymer). A suitable water-soluble polymer for pegylation of the antibodies and antibody fragments of the invention is polyethylene glycol (PEG). As used herein, "polyethylene glycol" is meant to encompass any of the forms of PEG that have been used to derivatize other proteins, such as mono (C1—C10) alkoxy- or aryloxy-polyethylene glycol.

Methods for preparing pegylated antibodies and antibody fragments of the invention will generally comprise the steps of (a) reacting the antibody or antibody fragment with polyethylene glycol, such as a reactive ester or aldehyde derivative of PEG, under suitable conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

Generally the pegylated antibodies and antibody fragments have increased half-life, as compared to the nonpegylated antibodies and antibody fragments. The pegylated antibodies and antibody fragments may be employed alone, together, or in combination with other pharmaceutical compositions.

An antibody of the invention can be derivatized or linked to another functional molecule (e.g., another peptide or protein). For example, an antibody of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody of the invention may be derivatized include fluorescent compounds. Exemplary fluorescent detectable agents include fluorescein, fluorescein isothiocyanate, rhodanine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

5.7. Pharmaceutical Compositions

The proteins of interest, e.g., antibodies and antibody-binding portions thereof, of the invention can be incorporated into pharmaceutical compositions suitable for administration to a subject. In certain embodiments, the pharmaceutical composition comprises an antibody of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is desirable to include isotonic agents, e.g., sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody.

The antibodies and antibody-binding portions thereof, of the invention can be incorporated into a pharmaceutical composition suitable for parenteral administration. The antibody or antibody-portions can be prepared as an injectable solution containing, e.g., 0.1-250 mg/mL antibody. The injectable solution can be composed of either a liquid or lyophilized dosage form in a flint or amber vial, ampule or pre-filled syringe. The buffer can be L-histidine approximately 1-50 mM, (optimally 5-10 mM), at pH 5.0 to 7.0 (optimally pH 6.0). Other suitable buffers include but are not limited to sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 24%). Stabilizers can be used in both liquid and lyophilized dosage forms, principally 1-50 mM L-methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

In one aspect, the pharmaceutical composition includes the antibody at a dosage of about 0.01 mg/kg-10 mg/kg. In another aspect, the dosages of the antibody include approximately 1 mg/kg administered every other week, or approximately 0.3 mg/kg administered weekly. A skilled practitioner can ascertain the proper dosage and regime for administering to a subject.

The compositions of this invention may be in a variety of forms. These include, e.g., liquid, semi-solid and solid dosage forms, such as liquid solutions (e.g., injectable and infusible solutions), dispersions or suspensions, tablets, pills, powders, liposomes and suppositories. The form depends on, e.g., the intended mode of administration and therapeutic application. Typical compositions are in the form of injectable or infusible solutions, such as compositions similar to those used for passive immunization of humans with other antibodies. One mode of administration is parenteral (e.g., intravenous, subcutaneous, intraperitoneal, intramuscular). In one aspect, the antibody is administered by intravenous infusion or injection. In another aspect, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the methods of preparation are vacuum drying and spray-drying that yields a powder of the active ingredient plus any additional desired ingredient from a previously sterile-filtered solution thereof. The proper fluidity of a solution can be maintained, e.g., by the use of a coating such as lecithin, by the maintenance of the required particle size in the case of dispersion and by the use of surfactants. Prolonged absorption of injectable compositions can be brought about by including in the composition an agent that delays absorption, e.g., monostearate salts and gelatin.

The antibodies and antibody-binding portions thereof, of the present invention can be administered by a variety of methods known in the art, one route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978, the entire teaching of which is incorporated herein by reference.

In certain aspects, an antibody or antibody-binding portion thereof, of the invention may be orally administered, e.g., with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain aspects, an antibody or antibody-binding portion thereof, of the invention is co-formulated with and/or co-administered with one or more additional therapeutic agents that are useful for treating disorders. Such combination therapies may advantageously utilize lower dosages of the administered therapeutic agents, thus avoiding possible toxicities or complications associated with the various monotherapies. It will be appreciated by the skilled practitioner that when the antibodies of the invention are used as part of a combination therapy, a lower dosage of antibody may be desirable than when the antibody alone is administered to a subject (e.g., a synergistic therapeutic effect may be achieved through the use of combination therapy which, in turn, permits use of a lower dose of the antibody to achieve the desired therapeutic effect).

It should be understood that the antibodies of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent which imparts a beneficial attribute to the therapeutic composition, e.g., an agent which affects the viscosity of the composition.

6. EXAMPLES

6.1. Anion Exchange Chromatography Examples
6.1.1. Materials & Methods
6.1.1.1. Chromatography Method Except where noted, the materials and methods described in connection with the instant example were also employed in the examples of Sections 6.2., 6.3., and 6.4., below.

Pre-packed resin columns were used in the following experiments, except where specified. The column was equilibrated in a buffer system with appropriate pH and conductivity. The column load was prepared from Protein A affinity chromatography eluates or concentrated CEX chromatography elutes by buffer exchange (if the eluates were with different buffer components from the mixed mode target buffer system) or addition of the stock solutions and/or water to obtain the target pH and conductivity as specified (if the eluates were with the same buffer components as the mixed mode target buffer system). The prepared load material was filtered and loaded on the column according to the target load amount (g protein/L resin) as specified followed by washing with the equilibration buffer or buffer similar to equilibration buffer with volumes as specified. The column Flow Through/Wash were collected as fractions or as a pool. Mixed mode column was regenerated with 0.1M acetic acid, 0.15M NaCl pH3, or 0.1M Acetic acid solution, pH 3, or as specified. 1M NaOH solution was used for column cleaning.

6.1.1.2. Buffer Preparation Method

Buffers were prepared targeting specific ion concentration for the anion by fixing the anion concentration (acid) to the target value, and adjusting the solution with the cationic component (base) to achieve the appropriate pH. For example to prepare a 10 mM Acetate-Tris buffer solution, pH 8.7, glacial acetic acid was dissolved in water to a target concentration of 10 mM and adjusted with concentrated Tris-base to pH 8.7.

6.1.1.3. AR Reduction and Recovery Calculations

In general, the Flow Through/Wash fractions were collected and analyzed with WCX-10 method for AR levels. By actual or calculated pooling of the fractions the recovery and the corresponding AR levels were calculated.

6.1.1.4. WCX-10 for Adalimumab

The acidic species and other charge variants present in the Adalimumab process samples were quantified according to the following methods. Cation exchange chromatography was performed on a Dionex ProPac WCX-10, Analytical column 4 mm×250 mm (Dionex, Calif.). An Agilent 1200 HPLC system was used as the HPLC. The mobile phases used were 10 mM Sodium Phosphate dibasic pH 7.5 (Mobile phase A) and 10 mM Sodium Phosphate dibasic, 500 mM Sodium Chloride pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm.

Quantitation was based on the relative area percent of detected peaks. The peaks that elute at relative residence time less than a certain time are together represented as the acidic peaks.

6.1.1.5. WCX-10 for mAb-B

The acidic species and other charge variants present in the mAb-B process samples were quantified according to the following methods. Cation exchange chromatography was performed on a Dionex ProPac WCX-10, Analytical column 4 mm×250 mm (Dionex, Calif.). An Agilent 1200 HPLC system was used as the HPLC. The mobile phases used were 20 mM 4-Morpholineethanesulfonic acid (MES), pH 6.5 (Mobile phase A) and 20 mM 4-Morpholineethanesulfonic acid (MES), 500 mM Sodium Chloride pH 6.5 (Mobile phase B). A binary gradient (87% A, 13% B: 0-5 min; 87% A, 13% B: 5-35 min; 75% A, 25% B: 35-40 min; 0% A, 100% B: 40-43 min; 87% A, 13% B: 43-46 min; 87% A, 13% B: 46-55 min) was used with detection at 280 nm, bw 8 nm; ref 360 nm, bw 100 nm.

Quantitation was based on the relative area percent of detected peaks. All peaks eluting prior to the Main Isoform peak were summed as the acidic region, and all peaks eluting after the LYS-2 peaks will be summed as the basic region.

6.1.1.6. WCX-10 for mAb-C

The mAb-C method was employed towards the quantification of the acidic species and other charge variants present mAb-C process samples. Cation exchange chromatography was performed on a Dionex ProPac WCX-10, Analytical column 4 mm×250 mm (Dionex, Calif.). An Agilent 1200 HPLC system was used as the HPLC. The mobile phases used were 20 mM 4-Morpholineethanesulfonic acid (MES), pH 6.0 (Mobile phase A) and 20 mM 4-Morpholineethanesulfonic acid (MES), 250 mM Sodium Chloride pH 6.0 (Mobile phase B). A binary gradient (97% A, 3% B: 0-1 min; 79% A, 21% B: 1-46 min; 0% A, 100% B: 46-47 min; 0% A, 100% B: 47-52 min; 97% A, 3% B: 52-53 min; 97% A, 3% B: 53-60 min) was used with detection at 280 nm, bw 8 nm; ref 360 nm, bw 100 nm.

Quantitation was based on the relative area percent of detected peaks. All peaks eluting prior to the Main Isoform peak will be summed as the acidic region, and all peaks eluting after the Main Isoform peak will be summed as the basic region.

6.1.1.7. Size Exclusion Chromatography

The molecular weight distribution of collected samples were quantified according to the following methods. Size exclusion chromatography (SEC) was performed using a TSK-gel G3000SWxL, 5 μm, 125 Å, 7.8×300 mm column (Tosoh Bioscience) on an HP Agilent HPLC system. Injections were made under isocratic elution conditions using a mobile phase of 200 mM sodium sulfate, 100 mM sodium phosphate, pH 6.8, and detected with absorbance at 214 nm. Quantification is based on the relative area of detected peaks.

6.1.1.8. Host Cell Protein (HCP) ELISA

HCP assay is based on process specific antigen based ELISA. Sample dilutions were applied to achieve readings within the calibration range. The limit of quantitation of the assay is 0.625 ng/mL.

6.1.1.9. UV spectroscopy $A_{280}$

UV A280 was used to determine protein concentrations for the samples post protein A elution. The assay was performed on an Agilent UV Spectrophotometer following the method. The protein concentration was determined using Beer-Lambert's Law, $A=\epsilon lc$, where A is Absorbance, E is the extinction coefficient, l is the path length, and c is the concentration. The absorbance was taken at 280 nm, the path length was 1 cm, and the extinction coefficients were 1.39 for Adalimumab, 1.38 for mAb B, and 1.43 for mAb C.

6.1.2 Example AEX 1: Determining Operating Conditions Appropriate for a Mab: Media: Buffer Combination The demonstration of the current invention for a specific antibody & resin is provided in this example, and consists of
1. Choosing an anion concentration that allows product and impurities to bind at a given pH above the pI of the product.
2. Performing a pH gradient elution covering a range above, at, and below the pI of the product.
3. Determining pH range in which the protein elutes from the anion exchange media.

In this example, adalimumab and Poros 50PI were chosen. The experiment was performed at acetate (anion) concentration of 5 mM. The column was equilibrated with 5 mM acetate/iTris at a pH of 9.0. Adalimumab was prepared at 5 mM acetate/Tris pH 9.0 and loaded to the column at 20 g-protein/L of resin. The column was washed with 10 CVs of the equilibration buffer. A pH gradient from 9.0 to 7.0 at an anion concentration of 5 mM acetate/Tris was then performed. The process chromatograms are shown in FIG. 1.

The demonstration of the current invention for a specific antibody & resin is provided in this example, and consists of
1. For a given pH, choosing a starting anion concentration that allows product and impurities to bind to the AEX adsorbent.
2. Loading a small amount of protein to the column and then performing a linear gradient elution by increasing the anion concentration keeping pH constant.
3. Determining anion concentration range in which the protein elutes from the anion exchange media.

Figure 2:
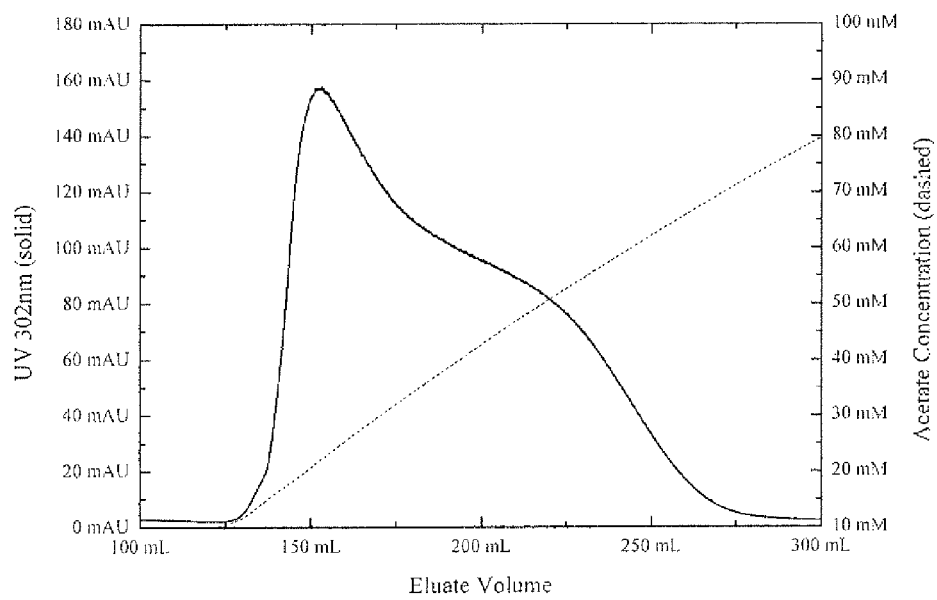
FIG. 2 depicts a process chromatogram of a linear gradient elution by increasing anion concentration in the context of AEX chromatography.

In this example, adalimumab and Poros 50HQ were chosen. The experiment was performed at a pH 8.7. The column was equilibrated with 10 mM acetate/Tris at pH 8.7. Adalimumab was prepared at 10 mM acetate/Tris pH 8.7 and loaded to the column at 20 g-protein/L of resin. The column was washed with 10 CVs of the equilibration buffer. A linear gradient from 10-100 mM Acetate/Tris at pH 8.7 was performed. The process chromatograms are shown in FIG. 2.

This general approach is used to determine the appropriate operating condition, example shown in Table 3, for any resin/mAb combination, to implement the invention.

TABLE 3

Example Experimental Design Scope determined from pH and anion gradient elution
Poros 50HQ - 300 g/L Loading - 30 g/L Fractionation

| | |
|---|---|
| pH Range | 8.2-9.0 |
| Anion Concentration (acetate) | 10-20 mM |

In practicing the current invention, the acidic species reduction desired can be achieved by appropriate pooling of the load and wash fractions. By collecting and subsequently determining the product quality of each fraction throughout the load and wash, the accumulative AR reduction and accumulative yield can be calculated using the weighted averages up to a given fraction. Additionally, the instantaneous yield can be estimated by comparing the protein recovered against the total protein loaded to the column at a given fraction. Sample calculations are shown below:

Sample Calculation A: Accumulative Yield up to a given fraction $$\text{Accumulative Yield} = \frac{\text{Accumulated Protein Mass Recovered up to Fraction}}{\text{Total Mass Protein Load}}$$

Sample Calculation B: Accumulative AR Reduction up to a given fraction $$\text{Accumulative } AR \text{ Reduction} = \text{Load } AR\ \% - \frac{\text{Accumulated Acidic Species Mass Recovered up to Fraction}}{\text{Accumulated Total Protein Mass Recovered up to Fraction}}$$

Sample Calculation C: Instantaneous Yield up to a given fraction $$\text{Instantaneous Yield} = \frac{\text{Accumulated Protein Mass Recovered up to Fraction}}{\text{Total Protein Mass Loaded to Column at Fraction}}$$

The demonstration of the current invention for a specific antibody & resin is provided in this example, and consists of
1. For a given pH and anion concentration and anion exchange media.
2. Loading the anion exchange media in excess of the dynamic binding capacity for the product for the given condition.

3. Washing the column with a buffer containing a similar pH and anion concentration used for the equilibration and loading steps.
4. Collecting fractions throughout the loading and wash steps and subsequently determining the product quality profile (e.g. AR, aggregate, etc.)

In this example, adalimumab and Poros 50PI were chosen. The experiment was performed at 5 mM acetate/arginine pH 8.8. The column was equilibrated with 5 mM acetate/arginine at pH 8.8. Adalimumab was prepared at 5 mM acetate/arginine pH 8.8 and loaded to the column at 300 g-protein/L-resin. The column was washed with 20 CVs of the equilibration buffer. Fractions were collected in volumes representing 30 g-protein/L-resin, shown in FIG. 3. Each fraction was then analyzed for product quality and the accumulative yield and AR reduction calculated, shown in Table 4. From this example, it is clear to one skilled in the art to determine a run condition which delivers a targeted product quality and/or step yield.

This general approach is used to evaluate the performance for a given operating condition for any resin/mAb/buffer combination.

TABLE 4

Figure 3:
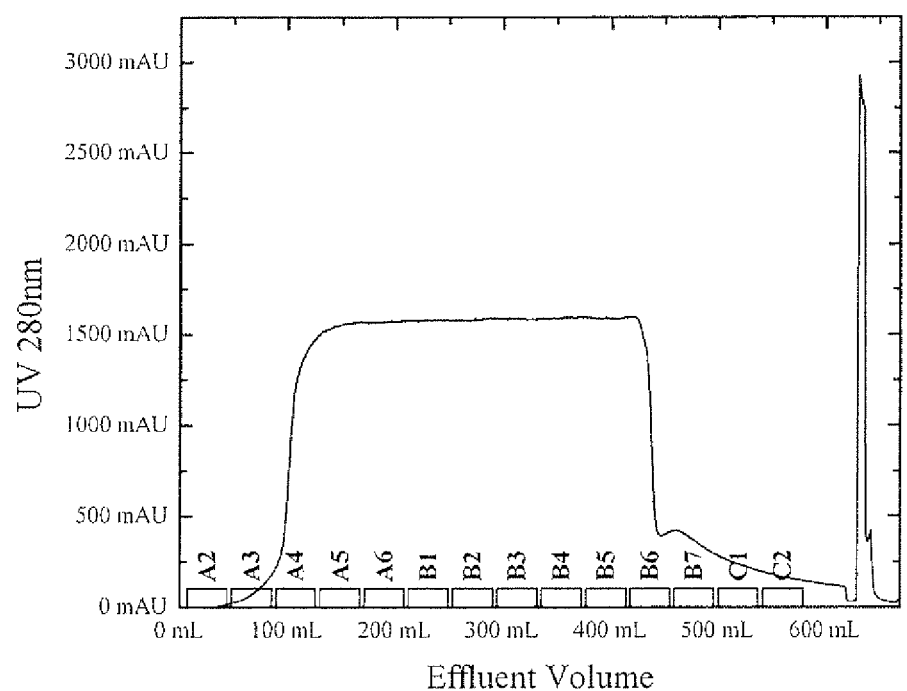
FIG. 3 depicts a process chromatogram of fractionation of 300 g/L load and wash in the context of AEX chromatography.

Accumulative Yield and AR Reduction from FIG. 3

| Fraction | Load | Accumulative Yield | ΔAR |
|---|---|---|---|
| A2 | 7 g/L | 0.0% | 10.8% |
| A3* | 37 g/L | 0.5% | 10.8% |
| A4 | 67 g/L | 6.7% | 9.7% |
| A5 | 97 g/L | 16.7% | 8.9% |
| A6 | 127 g/L | 26.9% | 8.4% |
| B1 | 157 g/L | 37.0% | 7.7% |
| B2 | 187 g/L | 47.1% | 7.1% |
| B3 | 217 g/L | 57.4% | 6.4% |
| B4 | 247 g/L | 67.8% | 5.8% |
| B5 | 277 g/L | 78.0% | 5.3% |
| B6 | 300 g/L | 84.4% | 5.0% |
| B7 | Wash | 87.0% | 4.8% |
| C1 | Wash | 88.5% | 4.7% |
| C2 | Wash | 89.6% | 4.6% |

*Dynamic Binding Capacity (DBC) = 39 g/L 6.1.3. Example AEX 2: Demonstration of AR Reduction with AEX Adsorbents This data set is compiled to demonstrate the AR reduction achieved with three different AEX adsorbents. Each resin was evaluated using adalimumab at an acetate concentration determined from the process outlined in Example 6.1.2. and at pH values below, near, and above the pI (e.g. pH 8.5 to 9.0). Table 5 outlines the results from these experiments.

TABLE 5

Effect of AEX Resins on AR reduction of Adalimumab

| Resin | Buffer Condition | Load | Yield | ΔAR |
|---|---|---|---|---|
| Poros 50PI | 5 mM Acetate/Tris pH 8.5 | 150 g/L | 90% | 2.4% |
| | 5 mM Acetate/Tris pH 8.5 | 300 g/L | 94% | 0.9% |
| | 5 mM Acetate/Tris pH 8.7 | 150 g/L | 87% | 3.6% |
| | 5 mM Acetate/Tris pH 8.7 | 300 g/L | 94% | 1.2% |
| | 5 mM Acetate/Tris pH 9.0 | 150 g/L | 83% | 3.9% |
| | 5 mM Acetate/Tris pH 9.0 | 300 g/L | 92% | 1.5% |
| Poros 50HQ | 18 mM Acetate/Tris pH 8.5 | 250 g/L | 91% | 3.8% |
| | 18 mM Acetate/Tris pH 8.5 | 350 g/L | 88% | 2.2% |
| | 18 mM Acetate/Tris pH 8.7 | 250 g/L | 85% | 6.0% |
| | 18 mM Acetate/Tris pH 8.7 | 350 g/L | 84% | 3.1% |

TABLE 5-continued

Effect of AEX Resins on AR reduction of Adalimumab

| Resin | Buffer Condition | Load | Yield | ΔAR |
|---|---|---|---|---|
| | 18 mM Acetate/Tris pH 8.9 | 250 g/L | 67% | 5.9% |
| | 18 mM Acetate/Tris pH 8.9 | 350 g/L | 75% | 3.6% |
| CaptoDEAE | 10 mM Acetate/Tris pH 8.5 | 150 g/L | 98% | 0.7% |
| | 10 mM Acetate/Tris pH 8.5 | 300 g/L | 97% | 0.1% |
| | 10 mM Acetate/Tris pH 8.7 | 150 g/L | 78% | 7.1% |
| | 10 mM Acetate/Tris pH 8.7 | 300 g/L | 95% | 2.5% |
| | 10 mM Acetate/Tris pH 9.0 | 150 g/L | 29% | 9.2% |
| | 10 mM Acetate/Tris pH 9.0 | 300 g/L | 82% | 5.0% |

This data set is compiled to demonstrate the AR reduction achieved with eight different AEX adsorbents. Each resin was tested using an advanced screening method using the process outlined in Example 6.1.2., and subjected to four runs using adalimumab at two different pH (e.g. pH 8.7 and 9.0) and two different acetate concentrations (e.g. 10 mM and 20 mM). In these experiments, the instantaneous (e.g. not accumulative) AR reduction was measured by analyzing the load fraction at 150 g/L and subsequently compared across all resins. Table 6 outlines the results from these experiments.

TABLE 6

Advanced Screen of AEX Resins for AR reduction of Adalimumab

| Resin | pH | Acetate | Instantaneous AR Reduction @ 150 g/L |
|---|---|---|---|
| Poros 50HQ | 8.7 | 10 mM | 15.0% |
| | | 20 mM | 10.7% |
| | 9.0 | 10 mM | 8.6% |
| | | 20 mM | 13.4% |
| Poros 50PI | 8.7 | 10 mM | 6.2% |
| | | 20 mM | −0.1% |
| | 9.0 | 10 mM | 6.5% |
| | | 20 mM | 3.0% |
| Capto DEAE | 8.7 | 10 mM | 9.3% |
| | | 20 mM | −0.2% |
| | 9.0 | 10 mM | 8.6% |
| | | 20 mM | 7.8% |
| Capto Q Impres | 8.7 | 10 mM | 12.3% |
| | | 20 mM | 4.2% |
| | 9.0 | 10 mM | 12.3% |
| | | 20 mM | 6.5% |
| QAE-550C | 8.7 | 10 mM | 10.1% |
| | | 20 mM | 3.5% |
| | 9.0 | 10 mM | 7.8% |
| | | 20 mM | 4.5% |
| DEAE 650M | 8.7 | 10 mM | 5.2% |
| | | 20 mM | 0.1% |
| | 9.0 | 10 mM | 6.9% |
| | | 20 mM | −2.7% |
| GigaCap Q 650M | 8.7 | 10 mM | 8.1% |
| | | 20 mM | 5.8% |
| | 9.0 | 10 mM | 1.8% |
| | | 20 mM | 0.4% |
| TMAE HiCap | 8.7 | 10 mM | 4.1% |
| | | 20 mM | 2.8% |
| | 9.0 | 10 mM | 1.2% |
| | | 20 mM | −0.1% |

This data set is compiled to demonstrate the AR reduction achieved with two different AEX chromatographic membranes. Each membrane was tested using conditions outlined in Table 6. The results from these experiments are presented in Table 7.

TABLE 7

Effect of AEX Chromatographic Membrane on AR reduction of Adalimumab

| Chromatographic Membrane | Equil/Wash Buffer | Load | Yield | ΔAR |
|---|---|---|---|---|
| Sartobind STIC | 10 mM Acetate/Tris pH 8.7 | 500 g/L | 94% | 1.7% |
|  | 20 mM Acetate/Tris pH 9.0 | 500 g/L | 100% | 0.7% |
| Sartobind Q | 20 mM Acetate/Tris pH 9.0 | 500 g/L | 100% | 0.3% |

This data set is compiled to demonstrate the AR reduction achieved with two different charged depth filters. The results from these experiments are presented in Table 8.

TABLE 8

Effect of Charged Depth Filters on AR reduction of Adalimumab

| Depth Filter Media | Equil/Wash Buffer | Load | Yield | ΔAR |
|---|---|---|---|---|
| CUNO BioCap 25 | 18 mM Acetate/Tris pH 8.7 | 500 g/m$^2$ | 92% | 1.9% |
| X0HC | 18 mM Acetate/Tris pH 8.7 | 500 g/m$^2$ | 84% | 1.1% |

6.1.4. Example AEX 3: Demonstration of AR Reduction with Other Antibodies, Mab B And Mab C AR reduction technology of the current invention has been demonstrated with multiple antibodies using AEX adsorbents. Antibodies have different amount charged residues and at different positions, leading to a charge interaction behavior on an AEX column that differs from one antibody to another, Therefore the impact of anion type, anion concentration is different for each antibody.

Table 9 and Table 10 below show the data for MAB B and MAB C. The data clearly demonstrates that the AR reduction technology works very effectively for other antibodies.

TABLE 9

AR reduction for mAb B, pI ~9.1

| Resin | Buffer Condition | pH | Load | Yield | ΔAR |
|---|---|---|---|---|---|
| Poros 50PI | 5 mM Acetate/Tris | 9.5 | 300 g/L | 83% | 1.1% |
|  |  | 9.1 | 300 g/L | 94% | 1.6% |
|  |  | 8.5 | 300 g/L | 98% | <0.5% |
| Poros 50HQ | 10 mM Acetate/Tris | 9.5 | 300 g/L | 69% | <0.5% |
|  |  | 9.1 | 300 g/L | 78% | 5.7% |
|  |  | 8.5 | 300 g/L | 81% | 3.4% |
| Capto DEAE | 10 mM Acetate/Tris | 9.5 | 300 g/L | 69% | 4.2% |
|  |  | 9.1 | 300 g/L | 82% | 4.9% |
|  |  | 8.5 | 300 g/L | 96% | <0.5% |

TABLE 10

AR reduction for mAb C, pI ~7.0

| Resin | Buffer Condition | pH | Load | Yield | ΔAR |
|---|---|---|---|---|---|
| Poros 50PI | 12 mM Acetate/Tris | 7.5 | 300 g/L | 90% | 2.6% |
|  |  | 7.0 | 300 g/L | 89% | 2.2% |
|  |  | 6.5 | 300 g/L | 87% | 4.0% |
| Poros 50HQ | 45 mM Acetate/Tris | 7.5 | 300 g/L | 86% | 1.2% |
|  |  | 7.0 | 300 g/L | 88% | 1.2% |
|  |  | 6.5 | 300 g/L | 91% | 0.7% |
| Capto DEAE | 25 mM Acetate/Tris | 7.5 | 300 g/L | 79% | 1.8% |
|  |  | 7.0 | 300 g/L | 80% | 1.9% |
|  |  | 6.5 | 300 g/L | 89% | 1.8% |

6.1.5. Example AEX 4: Demonstration of AR Reduction with Different pH Conditions—Adalimumab The AR species in the current invention is bound during the loading step; therefore the binding pH is a key variable. The anion concentration that provides the desired performance will vary with the operational pH.

Figure 4:
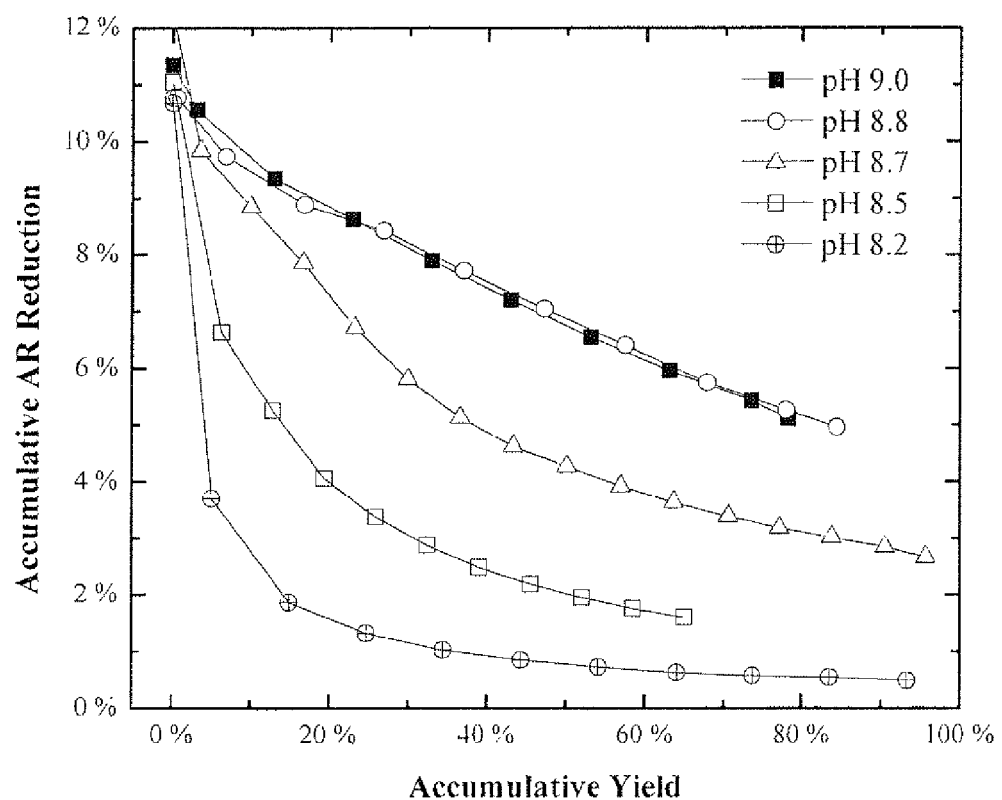
FIG. 4 depicts the effect of pH on AR reduction in the context of AEX chromatography.

In this example, data compiled from different experiments is shown to demonstrate the impact of the pH choice, relative to the pI of the protein on AR reduction. This data set provides the basis for one skilled in the art to determine a pH range to perform the experiments to implement the current invention. Furthermore, this reiterates the fact that the pH choice depends on several factors and the relationship between pH and AR reduction is also mAb dependent In this example, adalimumab and Poros 50PI were chosen. The experiments were performed at a concentration of 5 mM acetate/arginine at each pH specified. Adalimumab was prepared at 5 mM acetate/arginine at each pH specified and loaded to the column at 300 g-protein/L of resin. The column was washed with 20 CVs of the equilibration buffer. The results showing the pH effect on AR reduction is shown in FIG. 4.

It is also clear that the AR reduction can be achieved with the present invention with a range of pH choices in the range of ±0.5 pH units from the pI of multiple mAbs, which are listed in Table 11. Each of these experiments was performed with Poros50HQ resin at a 300 g/L load with an acetate/Tris buffer system.

TABLE 11

AR reduction at pH above, at, and below protein pI

| Range | pH-pI | Molecule | Yield | ΔAR |
|---|---|---|---|---|
| pH > pI | 0.2 | Adalimumab | 71% | 7.0% |
|  | 0.5 | mAb B | 69% | 3.4% |
|  | 0.5 | mAb C | 86% | 1.2% |
| pH~pI | 0 | Adalimumab | 86% | 5.9% |
|  | 0 | mAb B | 78% | 5.7% |
|  | 0 | mAb C | 88% | 1.2% |
| pH < pI | -0.2 | Adalimumab | 93% | 4.1% |
|  | -0.5 | mAb B | 81% | <0.5% |
|  | -0.5 | mAb C | 91% | 0.7% |

6.1.6. Example AEX 5: Demonstration of AR Reduction with Different Ion Concentrations—Adalimumab Anion concentration is a key variable in the performance of anion exchange chromatography. For every combination of antibody/resin/pH there is a range of anion concentrations that provides AR reduction; the strategy outlined in Example 6.1.2. can be followed to determine the AR reduction and the corresponding recovery for each anion concentration.

Table 12 below shows the effect of anion concentration on AR reduction. The table also includes the effect of anion concentration for different pH values. The data demonstrates that the AR reduction can be effectively achieved over a range of anion concentrations at each pH and that the concentration ranges depend on the pH.

TABLE 12

Effect of Anion Concentration and pH on AR reduction

| Resin | pH | Buffer Condition | Load | Yield | ΔAR |
|---|---|---|---|---|---|
| Poros 50PI | 9 | 5 mM Acetate/Arginine | 300 g/L | 81% | 4.8% |
|  |  | 10 mM Acetate/Arginine | 227 g/L | 80% | 2.4% |
|  |  | 18.5 mM Acetate/Arginine | 107 g/L | 88% | 1.0% |

TABLE 12-continued

Effect of Anion Concentration and pH on AR reduction

| Resin | pH | Buffer Condition | Load | Yield | ΔAR |
|---|---|---|---|---|---|
| | 8.8 | 5 mM Acetate/Arginine | 300 g/L | 93% | 4.5% |
| | | 10 mM Acetate/Arginine | 227 g/L | 88% | 2.5% |
| | | 18.5 mM Acetate/Arginine | 108 g/L | 96% | 1.2% |

6.1.7 Example AEX 6: Demonstration of AR Reduction with Different Buffer Systems with Adalimumab The anion type and concentration are key variables in Anion Exchange Chromatography. The invention has been demonstrated with Acetate and Formate as the anion type and Tris and Arginine as the counter cation type. As one skilled in the art would appreciate the optimal pH and cation concentration is different for each cation type/mixture and was derived by using the strategy outlined in Example 6.1.2. Table 13 shows the data of AR reduction and corresponding recovery for the different anion/cation types.

TABLE 13

Effect of Anion/Cation Type AR reduction

| Resin | Buffer Condition | Load | Yield | ΔAR |
|---|---|---|---|---|
| Poros 50PI | 5 mM Acetate/Tris, pH 8.7 | 300 g/L | 94% | 1.2% |
| | 2.5 mM Formate/Tris, pH 8.7 | 300 g/L | 92% | 1.3% |
| | 5 mM Acetate/Arginine, pH 8.8 | 300 g/L | 93% | 4.5% |
| Poros 50HQ | 15 mM Acetate/Arginine, pH 8.7 | 300 g/L | 89% | 3.2% |
| | 10 mM Formate/Tris, pH 8.7 | 300 g/L | 83% | 4.9% |
| | 18 mM Acetate/Tris, pH 8.7 | 300 g/L | 86% | 5.9% |
| Capto DEAE | 10 mM Acetate/Tris, pH 8.7 | 300 g/L | 95% | 2.5% |
| | 10 mM Formate/Tris, pH 8.7 | 300 g/L | 94% | 1.0% |
| | 5 mM Acetate/Arginine, pH 9.0 | 200 g/L | 41% | 7.5% |

6.1.8. Example AEX 7: Demonstration of Ar Reduction with Different Loading

Furthermore, the strategy outlined in Example 6.1.2. to reduce acidic species through careful control of buffer anion type, anion concentration, AEX adsorbent, and pH can be applied to any range of protein loading. A range of relevant protein loadings (e.g. 100-350 g/L) for Poros 50HQ at pH 8.7 using Acetate as the anion is shown in Table 14, displaying a robust AR reduction across the loading range investigated.

TABLE 14

Impact of Column loading

| Load | Yield (100-100 mAU) | ΔAR |
|---|---|---|
| 100 g/L | 78% | 9.7% |
| 200 g/L | 78% | 4.7% |
| 250 g/L | 85% | 6.0% |
| 300 g/L | 89% | 3.9% |
| 350 g/L | 84% | 3.1% |

6.1.9. Example AEX 8: Demonstration of Ar Reduction with Different Load Concentration Furthermore, the strategy outlined in Example 6.1.2. to reduce acidic species through careful control of buffer anion type, anion concentration, AEX adsorbent, and pH can be applied to any range of column feed streams of varying protein concentration. A range of varying protein load concentration for a 300 g/L load of adalimumab to Poros 50HQ at 15 mM acetate/Tris pH 8.7 is shown in Table 15.

TABLE 15

Effect of Protein Load concentration

| Load Concentration | Yield (100-100 mAU) | ΔAR |
|---|---|---|
| 5 mg/mL | 90% | 4.7% |
| 10 mg/mL | 86% | 4.5% |
| 15 mg/mL | 85% | 6.3% |
| 20 mg/mL | 84% | 6.2% |

6.2.10. Example AEX 9: Alternative Wash Modalities

In this example, adalimumab and Poros50HQ resin were selected. In each experiment, variations were made in the equilibration, loading, and washing pH values at a given acetate concentration (as specified). Table 16 and Table 17 show the effect of the pH variation in the step yield and AR reduction.

TABLE 16

Differences in pH in Equil/Wash/Load
Poros 50HQ - 15 mM Acetate/Tris - pH 8.7 - 200 g/L

| Equilibration pH | Load pH | Wash pH | Yield (100-100 mAU) | ΔAR |
|---|---|---|---|---|
| 8.7 | 8.7 | 8.5 | 83% | 8.7% |
| 9 | 8.5 | 8.5 | 89% | 5.1% |
| 9 | 100 g/L at pH 9.0<br>100 g/L at pH 8.5 | 8.5 | 94% | 4.5% |

TABLE 17

Differences in pH in Load/Wash
Poros 50HQ - 18 mM Acetate/Tris pH 8.7

| Load pH | Wash pH | Load | Yield | ΔAR |
|---|---|---|---|---|
| 8.6 | 8.4 | 75 g/L | 88.8% | 4.1% |
| 8.6 | 8.5 | 125 g/L | 89.5% | 4.2% |
| 8.6 | 8.6 | 100 g/L | 75.5% | 5.3% |
| 8.7 | 8.4 | 100 g/L | 93.8% | 4.1% |
| 8.7 | 8.5 | 100 g/L | 81.7% | 3.5% |
| 8.7 | 8.5 | 75 g/L | 94.5% | 4.0% |
| 8.7 | 8.6 | 125 g/L | 81.1% | 5.4% |
| 8.7 | 8.6 | 75 g/L | 65.8% | 6.5% |
| 8.8 | 8.4 | 125 g/L | 93.5% | 3.8% |
| 8.8 | 8.5 | 100 g/L | 83.7% | 5.8% |
| 8.8 | 8.6 | 100 g/L | 78.4% | 6.4% |
| 8.8 | 8.6 | 75 g/L | 72.7% | 7.0% |

As discussed in the previous sections, the operational pH and its relation to the product pI is important in the reduction of AR species in AEX. Similarly, the operational pH relative to the pKa of the AEX adsorbent is also important as many mAbs have pI similar to the pKa of the AEX adsorbent. This effect is shown in FIG. 24 for mAb B with several different AEX adsorbents, with different pKa values, run at with an acetate/Tris buffer at pH 9.1.

As described in previous sections the Acidic Region for Adalimumab is further grouped into two regions termed AR1 and AR2, based on a certain retention time of the peaks seen on the WCX-10 method. The characteristics of the variants in these two regions are expected to be different and hence the methods that reduce variants belonging to these groups can be specifically delineated.

Further, in addition to achieving a certain AR reduction, it may be desirable to achieve a certain absolute level of AR levels, in consideration of reducing or removing certain variants. The capability of the current invention in achieving a certain absolute level of AR, AR1 and AR2 is demonstrated in Table 18. The method of the current invention can effectively reduce AR2 levels, as an overall decrease in AR levels is achieved. The method can be used to achieve a target absolute level, as exemplified by the data presented in Table 18. Multiple species are present under the group of AR2 and that the current method of invention can be used to reduce such subspecies. The method of the current invention can effectively achieve AR reduction as well as achieve a target absolute level of acidic species as exemplified by the data presented in Table 18.

TABLE 18

AR1, AR2, and AR removal

| Resin | Buffer Condition | pH | Load | Yield | ΔAR1 | Final AR1 | ΔAR2 | Final AR2 | ΔAR |
|---|---|---|---|---|---|---|---|---|---|
| Poros 50PI | 5 mM Acetate/Tris | 8.5 | 150 g/L | 90% | 0.7% | 1.5% | 1.7% | 9.4% | 2.4% |
| | | | 300 g/L | 94% | 0.3% | 1.9% | 0.6% | 10.5% | 0.9% |
| | | 8.7 | 150 g/L | 87% | 0.9% | 1.2% | 2.7% | 8.2% | 3.6% |
| | | | 300 g/L | 94% | 0.4% | 1.7% | 0.8% | 10.1% | 1.2% |
| | | 8.9 | 150 g/L | 83% | 1.1% | 1.4% | 2.8% | 8.4% | 3.9% |
| | | | 300 g/L | 92% | 0.7% | 1.8% | 0.7% | 10.5% | 1.5% |
| Poros 50HQ | 18 mM Acetate/Tris | 8.5 | 250 g/L | 91% | 2.9% | 1.1% | 0.9% | 10.8% | 3.8% |
| | | | 350 g/L | 88% | 2.7% | 1.3% | −0.5% | 12.2% | 2.2% |
| | | 8.7 | 250 g/L | 88% | 3.1% | 0.9% | 2.9% | 9.0% | 6.0% |
| | | | 350 g/L | 84% | 2.8% | 1.2% | 0.3% | 11.6% | 3.1% |
| | | 8.9 | 250 g/L | 67% | 2.6% | 1.4% | 3.2% | 8.6% | 5.9% |
| | | | 350 g/L | 75% | 2.3% | 1.7% | 1.3% | 10.5% | 3.6% |
| CaptoDEAE | 10 mM Acetate/Tris | 8.5 | 150 g/L | 98% | −0.1% | 2.1% | 0.8% | 10.0% | 0.7% |
| | | | 300 g/L | 97% | 0.0% | 2.0% | 0.1% | 10.8% | 0.1% |
| | | 8.7 | 150 g/L | 78% | 2.4% | 0.8% | 4.7% | 6.4% | 7.1% |
| | | | 300 g/L | 95% | 1.5% | 1.7% | 1.0% | 10.1% | 2.5% |
| | | 8.9 | 150 g/L | 29% | 2.1% | 0.8% | 8.0% | 3.0% | 10.2% |
| | | | 300 g/L | 82% | 1.7% | 1.2% | 3.3% | 7.7% | 5.0% |

6.1.11. Example AEX 10: Demonstration of HCP and Aggregate Reduction in Addition to AR Reduction AEX chromatography is effective in reducing aggregate and HCP levels. In the present invention, it has been demonstrated that HCP and aggregate levels can be effectively reduced under operating conditions selected for AR reduction. Table 19 and Table 20 shows the aggregate and HCP removal achieved along with AR reduction. The data clearly shows that other process related and product related substances/impurities can be achieved using the current invention on the AEX adsorbents, and hence functions as an effective polishing step in the large scale purification of monoclonal antibodies.

TABLE 19

Aggregate removal during AEX Chromatography

| Buffer Condition | Load | Yield | ΔAggregate Absolute | Relative | ΔAR |
|---|---|---|---|---|---|
| 5 mM Acetate/Tris, pH 9.0 | 300 g/L | 81% | 0.92% | 93% | 4.5% |
| 10 mM Acetate/Tris, pH 9.0 | 227 g/L | 80% | 0.81% | 88% | 2.4% |
| 18.5 mM Acetate/Tris, pH 9.0 | 107 g/L | 88% | 0.37% | 41% | 1.0% |
| 5 mM Acetate/Tris, pH 8.8 | 300 g/L | 93% | 0.91% | 91% | 4.5% |
| 10 mM Acetate/Arginine, pH 8.8 | 227 g/L | 88% | 0.67% | 77% | 2.5% |
| 18.5 mM Acetate/Arginine, pH 8.8 | 108 g/L | 96% | 0.34% | 40% | 1.2% |

TABLE 20

HCP Removal during AEX Chromatography
Poros 50PI - D2E7 - 300 g/L

| Buffer Condition | Yield | Load HCP (ng/mL) | Pool HCP (ng/mL) | HCP (LRF) | ΔAR |
|---|---|---|---|---|---|
| 5 mM Acetate/Tris, pH 9.0 | 81% | 11,617 | 69 | 2.2 | 4.8% |
| 10 mM; Acetate/Tris, pH 9.0 | 95% | | 83 | 2.1 | 0.8% |

TABLE 20-continued

HCP Removal during AEX Chromatography
Poros 50PI - D2E7 - 300 g/L

| Buffer Condition | Yield | Load HCP (ng/mL) | Pool HCP (ng/mL) | HCP (LRF) | ΔAR |
|---|---|---|---|---|---|
| 5 mM Acetate/Tris, pH 8.8 | 93% | 13,507 | 51 | 2.4 | 4.5% |
| 10 mM Acetate/Arginine, pH 8.8 | 97% | | 84 | 2.2 | 1.5% |

6.1.12. Example AEX 11: Demonstration of Means of Controlling AR Reduction

Controlling the final product quality by modifying the process based on the quality of the intermediate material is an approach that has been proposed as an effective way of ensuring product quality, with the view of ensuring safety and efficacy.

Considering that the AR levels generated during cell culture and other upstream steps can be variable, it is desirable to design a downstream process step that implements a means of controlling the product quality; and to further have a specific means of controlling a process parameter to influence the quality of the product.

In the current invention, such a control is possible, as the pH and load (i.e. g/L) are parameters that can be modified to achieve a desired separation of the AR species. For example, to achieve a higher level of AR reduction at a given anion concentration and pH, the load to the column can be reduced. Additionally, for a given anion concentration and loading, the pH can be increased in order to achieve a higher reduction in AR species.

As an example, and not to be restrictive in any manner, it has been demonstrated in this example that the AR levels can be controlled by changing the pH of the load and wash solutions as well as the total load to the column. A pilot scale Poros HQ column (10 cm diameter×22.5 cm height, 1.8 L), was used for this study.

The load material and the stock buffer are both prepared at 18 mM Acetate/Tris the specified pH by titrating the affinity captured material with a stock Tris solution. The AR level of the load material was the same for both runs. This experiment demonstrates how the final AR level can be modulated, while maintaining acceptable yields, by adjusting the pH and protein load to the column, shown in Table 21.

TABLE 21

Modulating AR Reduction using Process Analytical Technology approach

| Buffer Condition | Load | Yield | ΔAR | Final AR |
|---|---|---|---|---|
| 18 mM Acetate/Tris, pH 8.7 | 200 g/L | 77% | 5.6% | 5.5% |
| 18 mM Acetate/Tris, pH 8.5 | 300 g/L | 89% | 3.1% | 8.2% |

Figure 5:
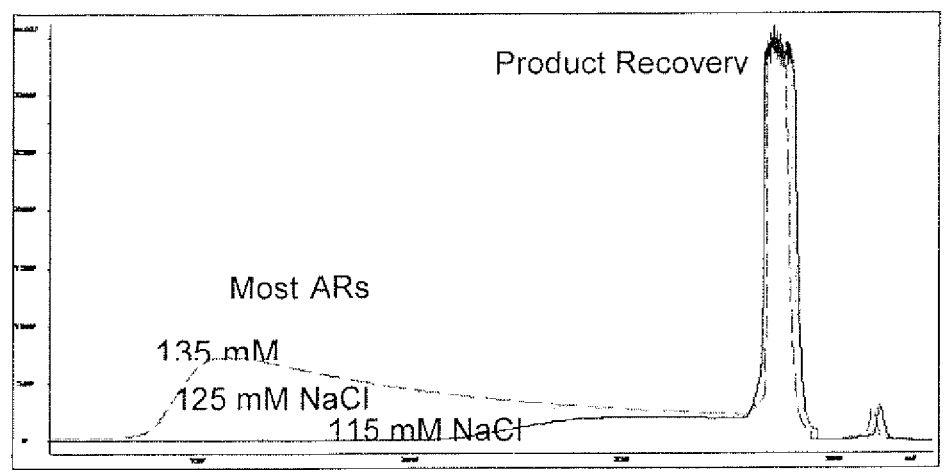
FIG. 5 depicts a process chromatogram at different salt (cation) concentrations in the context of CEX chromatography.
Figure 6:
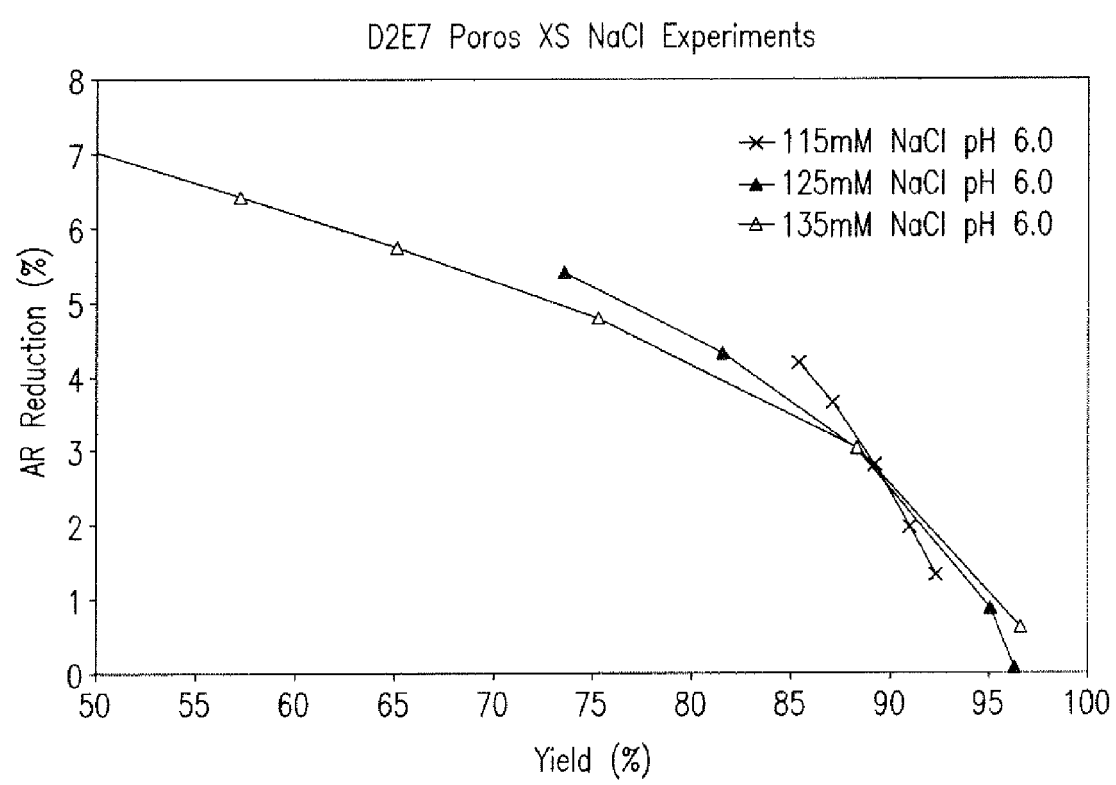
FIG. 6 depicts recovery versus AR reduction in the context of CEX purification of adalimumab.

6.2. Cation Exchange Chromatography Examples 6.2.1. Example CEX 1: Determining Operating Conditions Appropriate for A Mab: Resin: Buffer Combination The demonstration of the current invention for a specific antibody & resin is provided in this example, and consists of
1. Choosing a pH that is below the pI of the protein.
2. Choosing a NaCl concentration in the range of 100 to 150 mM and performing the experiments at, for example, 115, 125, 135 concentrations.
3. Determining the acidic species distribution in the ft/wash fraction vs the elution.
4. Choosing a NaCl concentration that provides the desired acidic species levels and recovery In this example, adalimumab was chosen and Poros XS was chosen. The experiments were performed at pH 6.0. The process chromatograms are shown in FIG. 5. The recovery vs AR reduction curves for each of the experiments is shown in FIG. 6 and Table 22. From this set of experiments, a sodium concentration of 125 mM can be chosen and such that the recovery of the eluate is 74%, which provides an AR reduction of 5.4%. Alternately, an AR reduction value of 5.4% can be chosen which will provide a recovery of ~75%.

This general approach is used to determine the appropriate operating condition for any resin/mAb combination, to implement the invention.

In practicing certain embodiments of the current invention, the acidic species reduction desired can be achieved by appropriate pooling of the elution fraction with the wash fractions. In the example described in the previous section the elution fractions can be pooled with wash fractions as shown in Table 22 to achieve AR reductions from about 1 percent to 7 percent depending on the fractions pooled. This approach can be implemented to achieve a target yield and AR reduction as exemplified in FIG. 6.

TABLE 22

Wash fractions and eluate combination versus AR reduction

| Wash Fractions | Recovery (%) | % AR Reduction |
|---|---|---|
| Eluate | 74 | 5.4 |
| Eluate + Fraction 1 | 82 | 4.3 |
| Eluate + Fraction 1 + Fraction 2 | 88 | 3.0 |
| Eluate + Fraction 1 + Fraction 2 + Fraction 3 | 95 | 0.9 |
| Eluate + Fraction 1 + Fraction 2 + Fraction 3 + Fraction 4 | 96 | 0.1 |

6.2.2. Example CEX 2: Demonstration of AR reduction with CEX Adsorbents

This data set is compiled to demonstrate the AR reduction achieved with 8 different CEX adsorbents. Conditions were derived for each resin based on the strategy outlined in Example 6.2.1. Table 23 outlines the conditions used and the AR reduction achieved and the corresponding recovery achieved.

The data clearly shows that the technology is robust in delivering AR reduction in all the 10 resins. As described in Example 6.2.1., the AR reduction can be balanced with recovery and an optimal condition can be chosen. Experiments were performed at pH 7.5. 29 mM Tris-acetate was used for pH control.

TABLE 23

Effect of CEX adsorbents on AR reduction

| Resin | Tris concentration (mM) | Yield (%) | % AR Reduction |
|---|---|---|---|
| Poros XS | 135 | 103.3 | 0.7 |
|  | 140 | 78.6 | 6.8 |
|  | 145 | 72.6 | 7.3 |
| Poros HS | 100 | 70.0 | 6.7 |
|  | 105 | 68.7 | 7.1 |
|  | 110 | 60.6 | 7.6 |
| Capto SP ImpRes | 50 | 71.5 | 5.7 |
|  | 55 | 61.0 | 6.3 |
|  | 60 | 46.2 | 6.8 |
| Nuvia S | 75 | 67.6 | 10.0 |
|  | 80 | 54.3 | 10.8 |
|  | 85 | 41.0 | 12.2 |
| Giga Cap CM 650 | 55 | 70.3 | 6.0 |
|  | 57.5 | 62.7 | 7.0 |
|  | 60 | 55.6 | 8.6 |
| Eshmuno S | 65 | 52.7 | 9.0 |
|  | 70 | 35.4 | 11.2 |
|  | 75 | 22.7 | 12.2 |
| Giga Cap S 650 | 65 | 66.3 | 8.4 |
|  | 70 | 43.6 | 11.1 |
|  | 75 | 31.4 | 12.1 |
| CM Hyper D | 45 | 72.2 | 8.9 |
|  | 47.5 | 63.2 | 9.9 |
|  | 50 | 51.5 | 10.3 |

6.2.3. Example CEX 3: Demonstration of AR Reduction with Other Antibodies: mAb B And mAb C AR reduction technology of the current invention has been demonstrated with multiple antibodies using CEX Adsorbents. Antibodies have different amounts of charged residues and at different positions, leading to a charge interaction behavior on a CEX column that differs from one antibody to another. Therefore the impact of cation type, cation concentration is different for each antibody.

For each antibody/resin combination, the experimental strategy outlined in Example 6.2.1. was employed to determine the cation concentration for each cation type that provided AR reduction.

Table 24 and Table 25 below shows the data for MAB B and MAB C. The data clearly demonstrates that the AR reduction technology works very effectively for other antibodies. It is also clear that the concentration ranges are different between different antibodies. The pH range chosen was related to the isoelectric point of the antibody and was chosen to be approximately 1 to 2 units less than the pI of the molecule.

TABLE 24

AR reduction for molecule B

| Resin | Buffer System | Concentration (mM) | pH | Yield (%) | % AR Reduction |
|---|---|---|---|---|---|
| Poros XS | Tris Acetate | 120 | 7.5 | 57.2 | 8.4 |
| | | 125 | | 46.5 | 9.3 |
| | | 130 | | 37.1 | 10.3 |
| Nuvia S | | 85 | | 72.5 | 16.6 |
| | | 90 | | 56.1 | 16.9 |
| | | 95 | | 44.2 | 17 |
| CM Hyper D | | 50 | | 73 | 8.2 |
| | | 55 | | 62 | 9.2 |
| | | 60 | | 52.6 | 9.2 |

TABLE 25

AR reduction for molecule C

| Resin | Buffer System | Concentration (mM) | pH | Yield (%) | Load % AR | % AR Reduction |
|---|---|---|---|---|---|---|
| Poros XS | Tris Acetate | 40 | 6.0 | 87.4 | 15.6 | 8.5 |
| | | 45 | | 56.8 | 15.7 | 12.8 |
| | | 50 | | 31.3 | 15.7 | 14.3 |
| Nuvia S | | 35 | | 45.1 | 11.5 | 11.2 |
| | | 37 | | 28.5 | 15.4 | 15.2 |
| | | 40 | | 15.3 | 15.2 | 15.2 |
| CM Hyper D | | 18 | | 83.6 | 16.3 | 6.3 |
| | | 20 | | 64.9 | 16.3 | 11.2 |
| | | 22 | | 50.7 | 16.4 | 12.3 |

6.2.4. Example CEX 4: Demonstration of AR Reduction with Different pH Conditions—Adalimumab The AR species in the current invention is removed in the Flow through/Wash fraction. Therefore the binding pH is a key variable. The cation concentration that provides the desired performance will vary with the binding pH. Therefore for each binding pH, the experimental strategy outlined in Example 6.2.1. is carried out to determine the range of ion concentration that results in AR reduction.

The results of the experiments with different pHs for Adalimumab is shown in Table 26. As can be seen, at lower pH, the cation concentration required to achieve AR removal in the wash fraction is higher. It is unexpected that the AR reduction is significantly more robust and optimal at higher pHs (closer to pI) than at lower pHs. It is not obvious to one skilled in the art to operate a cation exchange chromatography at pH closer to pI as shown in Table 27. Literature data suggests an optimal pH of at least 3 units less than the pI of the molecule.

TABLE 26

Effect of pH on AR reduction

| pH | Resin | Buffer System | Buffer Concentration (mM) | Yield (%) | % AR Reduction |
|---|---|---|---|---|---|
| 5.5 | Poros XS | Tris Acetate | 350 | 58.2 | 5.9 |
| 6.5 | | | 225 | 61.4 | 6.4 |
| 7 | | | 170 | 75.3 | 5.6 |
| 7.5 | | | 140 | 78.6 | 6.8 |
| 8 | | | 125 | 75.8 | 5.7 |

TABLE 26-continued

Effect of pH on AR reduction

| pH | Resin | Buffer System | Buffer Concentration (mM) | Yield (%) | % AR Reduction |
|---|---|---|---|---|---|
| 7.5 | CM Hyper D | Ammonium Sulfate | 4 | 77.9 | 7.4 |
| 6 | | Sodium Chloride | 45 | 86.1 | 4 |
| 6.8 | | | 30 | 71.5 | 7 |
| 7.5 | | | 10 | 71.3 | 6.8 |
| 7.5 | | Tris Acetate | 45 | 72.2 | 8.9 |

TABLE 27

Effect of delta pH and pI on AR reduction

| pI-pH | Molecule | Resin | Buffer system | [Cation] (mM) | Yield (%) | % AR Reduction |
|---|---|---|---|---|---|---|
| 1.1 | Adalimumab | Poros XS | Arginine/Tris Acetate | 60/29 | 58.9 | 7.8 |
| 2.2 | | | Sodium Chloride | 125 | 73.5 | 5.4 |
| 1.8 | | | | 75 | 90 | 1.5 |
| 1.1 | | | | 50 | 72.1 | 7.2 |
| 3.1 | | | Tris Acetate | 350 | 58.2 | 5.9 |
| 2.1 | | | | 225 | 61.4 | 6.4 |
| 1.6 | | | | 170 | 75.3 | 5.6 |
| 1.1 | | | | 145 | 72.6 | 7.3 |
| 0.6 | | | | 125 | 75.8 | 5.7 |
| 1.6 | mAb B | Poros XS | Tris Acetate | 120 | 57.2 | 8.4 |
| 1.6 | | CM Hyper D | Tris Acetate | 50 | 73 | 8.2 |
| 1.6 | | Nuvia S | Tris Acetate | 85 | 72.5 | 8.4 |
| 1.0 | mAb C | Poros XS | Tris Acetate | 40 | 87.4 | 8.5 |
| 1.0 | | CM Hyper D | Tris Acetate | 18 | 83.6 | 6.3 |
| 1.0 | | Nuvia S | Tris Acetate | 35 | 45.1 | 11.2 |

6.2.5. Example CEX 5: Demonstration of AR Reduction with Different Ion Concentrations—Adalimumab Cation concentration is a key variable in the performance of cation exchange chromatography. For every combination of antibody/resin/pH there is a range of cation concentrations that provides AR reduction; the strategy outlined in Example 6.2.1 can be followed to determine the AR reduction and the corresponding recovery for each cation concentration.

Table 28 below shows the effect of cation concentration on AR reduction. The table also includes the effect of cation concentration for different pH values. The data demonstrates that the AR reduction can be effectively achieved over a range of cation concentrations at each pH and that the concentration ranges depend on the pH. The table also includes an example of the concentration range for a different cation type.

TABLE 28

Effect of cation concentration and pH on AR reduction

| Cation concentration (mM) | Buffer system | pH | Resin | Yield (%) | % AR Reduction |
|---|---|---|---|---|---|
| 60/29 | Arginine/Tris Acetae | 7.5 | Poros XS | 58.9 | 7.8 |
| 65/29 | | | | 47.4 | 8.7 |
| 23 | | | | 80.5 | 5.8 |
| 25 | | | | 72.9 | 7.3 |
| 27 | | | | 52.2 | 9.5 |
| 115 | Sodium Chloride | 6 | | 85.4 | 4.2 |
| 125 | | | | 73.5 | 5.4 |
| 130 | | | | 48.7 | 7.1 |
| 75 | | 68 | | 90 | 1.5 |
| 90 | | | | 53.7 | 2.1 |
| 45 | | 7.5 | | 60.7 | 7.9 |

TABLE 28-continued

Effect of cation concentration and pH on AR reduction

| Cation concentration (mM) | Buffer system | pH | Resin | Yield (%) | % AR Reduction |
|---|---|---|---|---|---|
| 50 | | | | 72.1 | 7.2 |
| 350 | Tris Acetate | 5.5 | | 58.2 | 5.9 |
| 375 | | | | 38.4 | 7.4 |
| 400 | | | | 29.9 | 6.2 |
| 225 | | 6.5 | | 61.4 | 6.4 |
| 250 | | | | 59.5 | 6.6 |
| 275 | | | | 37.6 | 7.8 |
| 300 | | | | 21.6 | 8.8 |
| 165 | | 7 | | 83.8 | 4.3 |
| 170 | | | | 75.3 | 5.6 |
| 175 | | | | 70.3 | 5.7 |
| 140 | | 7.5 | | 78.6 | 6.8 |
| 145 | | | | 72.6 | 7.3 |
| 150 | | | | 69.2 | 7.8 |
| 175 | | | | 29.8 | 10.3 |
| 125 | | 8 | | 75.8 | 5.7 |
| 130 | | | | 67.7 | 6.5 |
| 135 | | | | 57.4 | 7.5 |

6.2.6 Example CEX 6: Demonstration of Ar Reduction with Different Buffer Systems with Adalimumab The cation type and concentration are key variables in Cation Exchange Chromatography. The invention has been demonstrated with Tris, Sodium/Tris, Ammonium/Tris and Arginine/Tris as cation types/mixtures with effective reduction of AR in each case. As one skilled in the art would appreciate the optimal pH and cation concentration is different for each cation type/mixture and was derived by using the strategy outlined in Example 6.2.1. Experiment were performed at pH 7.5. 29 mM Tris-acetate was used for pH control. Table 29 shows the data of AR reduction and corresponding recovery for the different cation types/mixtures.

TABLE 29

Effect of cation types/mixtures on AR reduction

| Buffer System | Resin | Cation concentration (mM) | pH | Yield (%) | % AR Reduction |
|---|---|---|---|---|---|
| Arginine/Tris acetate | Poros XS | 60 | 7.5 | 58.9 | 7.8 |
| Ammonium Sulfate | | 25 | | 72.9 | 7.3 |
| Sodium Chloride | | 50 | | 72.1 | 7.2 |
| Tris Acetate | | 140 | | 78.6 | 6.8 |
| Ammonium Sulfate | CM Hyper D | 4 | | 77.9 | 7.4 |
| Sodium Chloride | | 10 | | 71.3 | 6.8 |
| Tris Acetate | | 45 | | 72.2 | 8.9 |
| Ammonium Sulfate | Nuvia S | 11 | | 66.6 | 12.6 |
| Sodium Chloride | | 20 | | 75.9 | 10.5 |
| Tris Acetate | | 75 | | 67.6 | 10 |

6.2.7. Example CEX 7: Demonstration of AR Reduction with Different Loading

Furthermore, the strategy outlined in Example 6.2.1. to reduce acidic species through careful control of buffer cation type, concentration and pH can be applied to any range of protein loading which represents an operational mode of binding followed by elution, i.e. not overloaded or a column load factor below that of the adsorbents binding capacity. A range of relevant protein loadings for Poros XS at pH 7.5 using Tris as the cation is shown in Table 30 showing robust AR reduction.

TABLE 30

Impact of Column loading

| Column Loading (g product/ L resin) | Buffer System | Concentration (mM) | pH | Yield (%) | % AR Reduction |
|---|---|---|---|---|---|
| 25 | Tris | 160 | 7.5 | 83.6 | 6.4 |
| 30 | | 155 | | 79.4 | 6.0 |
| 35 | | 140 | | 87.4 | 4.8 |
| 38 | | 140 | | 83.5 | 5.0 |
| 40 | | 140 | | 76.4 | 6.0 |
| 42 | | 140 | | 74.5 | 5.7 |
| 45 | | 140 | | 67.0 | 6.6 |

6.2.8. Example CEX 18: Demonstration of AR Reduction with Different Load Concentration Furthermore, the strategy outlined in Example 6.2.1. to reduce acidic species through careful control of buffer cation type, concentration and pH can be applied to any range of column feed streams of varying protein concentration. A range of varying protein load concentration for Poros XS at pH 7.5 using Tris as the cation is shown in Table 31 showing robust AR reduction.

TABLE 31

Effect of Protein Load concentration

| Load Concentration (mg/mL) | Resin | Buffer System | Concentration (mM) | pH | Yield (%) | % AR Reduction |
|---|---|---|---|---|---|---|
| 3 | Poros XS | Tris Acetate | 140 | 7.5 | 77.3 | 7 |
| 4 | | | 145 | | 60.7 | 7 |
| 5 | | | 140 | | 78.7 | 6.7 |
| 5 | | | 145 | | 64.1 | 7 |
| 6 | | | 145 | | 59.5 | 6.9 |
| 7 | | | 140 | | 77.6 | 6.5 |

As described above, the Acidic Region for Adalimumab is further grouped into two regions termed AR1 and AR2, based on a certain retention time of the peaks seen on the WCX-10 method. The characteristics of the variants in these two regions are expected to be different and hence the methods that reduce variants belonging to these groups can be specifically delineated.

Further, in addition to achieving a certain AR reduction, it may be desirable to achieve a certain absolute level of AR levels, in consideration of reducing or removing certain variants. The capability of the current invention in achieving a certain absolute level of AR, AR1 and AR2 is demonstrated in Table 32.

The specific species comprising the AR1 species can be identified and quantitated, to demonstrate reduction of such species by methods of the current invention. Two of such species, Glycated mAb, and MGO modified mAb have been identified and shown to be reduced by the methods of this invention. While these species are among the Acidic Species part of the charge variants, the acidic species typically described in the literature is the deamidated mAb, which is distinctly different.

TABLE 32

The final impurity level

| Buffer System | Cation Conc. (mM) | pH | Yield (%) | % Final AR1 | % Final AR |
|---|---|---|---|---|---|
| Arginine/Tris | 60 | 7.5 | 58.9 | 0.3 | 5.8 |
| Acetate | 65 | 7.5 | 47.4 | 0.3 | 4.7 |
| Ammonium Sulfate | 23 | 7.5 | 80.5 | 0.6 | 8.3 |
|  | 25 | 7.5 | 72.9 | 0 | 6.4 |
|  | 27 | 7.5 | 52.2 | 0.4 | 5.0 |
| Sodium Chloride | 115 | 6 | 85.4 | 1.3 | 10.2 |
|  | 125 | 6 | 73.5 | 0 | 8.1 |
|  | 135 | 6 | 48.7 | 0 | 6.1 |
|  | 75 | 6.8 | 90 | 1.4 | 10.9 |
|  | 90 | 6.8 | 53.7 | 0.7 | 11.2 |
|  | 45 | 7.5 | 60.7 | 0 | 6.2 |
|  | 50 | 7.5 | 72.1 | 0 | 7.8 |
| Tris Acetate | 350 | 5.5 | 58.2 | 0 | 7.7 |
|  | 375 | 5.5 | 38.4 | 0.1 | 6.2 |
|  | 400 | 5.5 | 29.9 | 1.5 | 7.3 |
|  | 225 | 6.5 | 61.4 | 0.8 | 7.2 |
|  | 250 | 6.5 | 59.5 | 0 | 6.8 |
|  | 275 | 6.5 | 37.6 | 0 | 5.6 |
|  | 300 | 6.5 | 21.6 | 0 | 4.7 |

The method of the current invention can effectively reduce AR2 levels, as an overall decrease in AR levels is achieved. The method can be used to achieve a target absolute level, as exemplified by the data presented in Table 32.

The method of the current invention can effectively achieve AR reduction as well as achieve a target absolute level of acidic species as exemplified by the data presented in Table 32.

Figure 7:
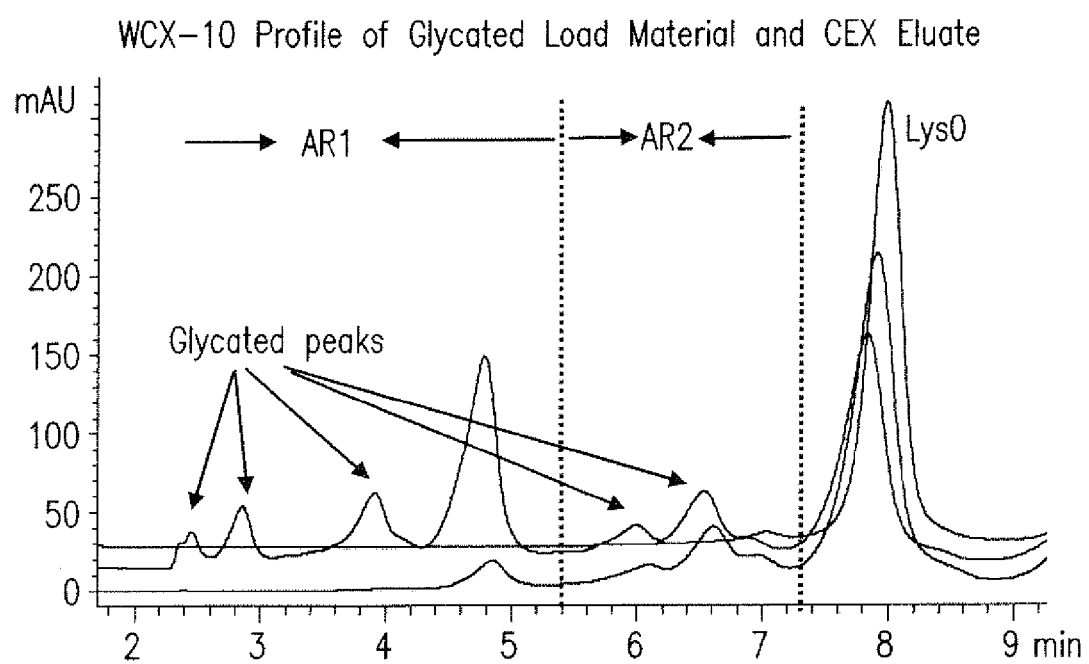
FIG. 7 depicts the WCX-10 profile of glycated load material and CEX Eluate.
Figure 8:
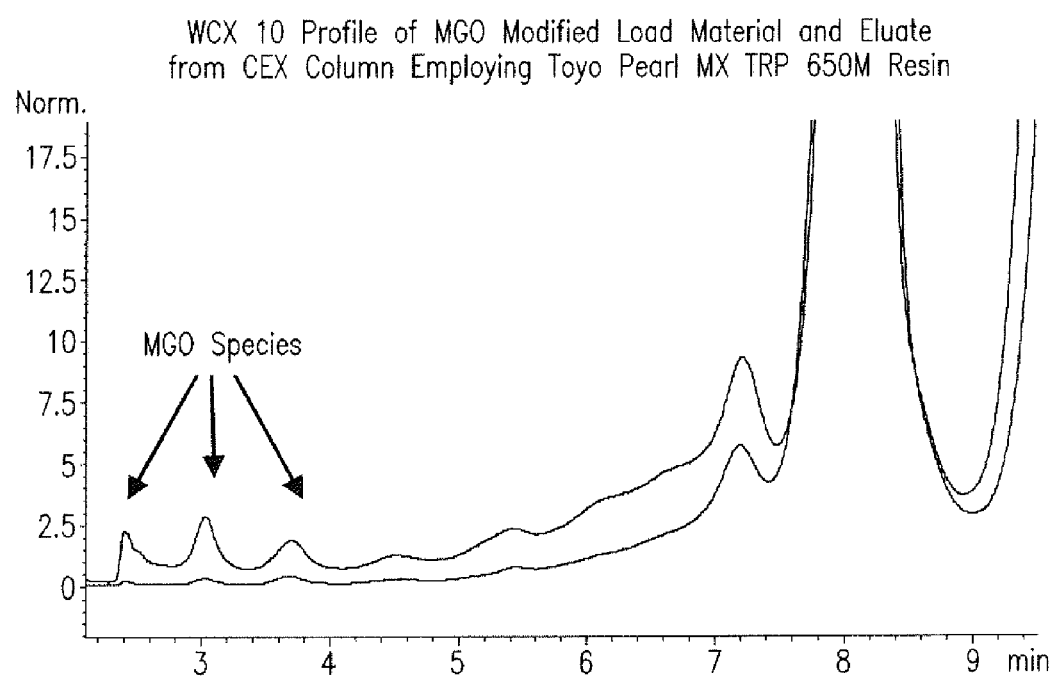
FIG. 8 depicts the WCX 10 profile of MGO modified load material and eluate from CEX column employing Toyo Pearl MX TRP 650M resin.

6.2.9. Example CEX 9 Demonstration of Glycated and Methylglyoxylated Species Reduction The strategy outlined in Example 6.2.1. to reduce acidic species through careful control of buffer cation type, concentration and pH can be further extended to specific post-translational modifications. While acidic species are defined in the application as impurities that are less retained than the main peak on an analytical weak cation exchange (WCX) HPLC column, specific known product related substances derived from cellular metabolism modification such as glycation and methylglyoxal (MGO) can be specifically identified as being part of the acidic species. FIG. 7 and FIG. 8 shows the outcome of in-vitro labeling experiments which demonstrate that glycation and MGO modified antibody are unique species that are resolved by the WCX method in the AR1 region of the chromatogram and can be enriched in vitro. Furthermore, the invention described here shows that glycated and MGO modified antibody can be effectively removed through the careful control of buffer cation type, concentration and pH using the CEX as described in Example 6.2.1. Quantitative reduction of AR1 and hence the Glycated and MGO species by CEX and CEX-Mixed Mode resins is show in Table 33 and Table 34.

TABLE 33

Glycated species removal

| Resin | Buffer System | Conc. (mM) | pH | Yield (%) | Load % AR1 | Load % AR | % AR1 Reduction | % AR Reduction |
|---|---|---|---|---|---|---|---|---|
| Poros XS | Tris | 135 | 7.5 | 54.0 | 40.8 | 58.6 | 30.8 | 34.8 |

TABLE 34

MGO peak removal

| Resin | Buffer System | Concentration (mM) | pH | Yield (%) | % AR1 Reduction | % AR Reduction |
|---|---|---|---|---|---|---|
| Toyo Pearl MX TRP 650M | Tris | 80 | 7.5 | 66.7 | 2.8 | 7.2 |
| Poros XS |  | 145 |  | 64.1 | 2.7 | 7 |
| Nuvia S |  | 90 |  | 48.5 | 3.1 | 9.6 |

6.2.10 Example CEX 10: Demonstration of Lysine Distribution Modification

Figure 9:
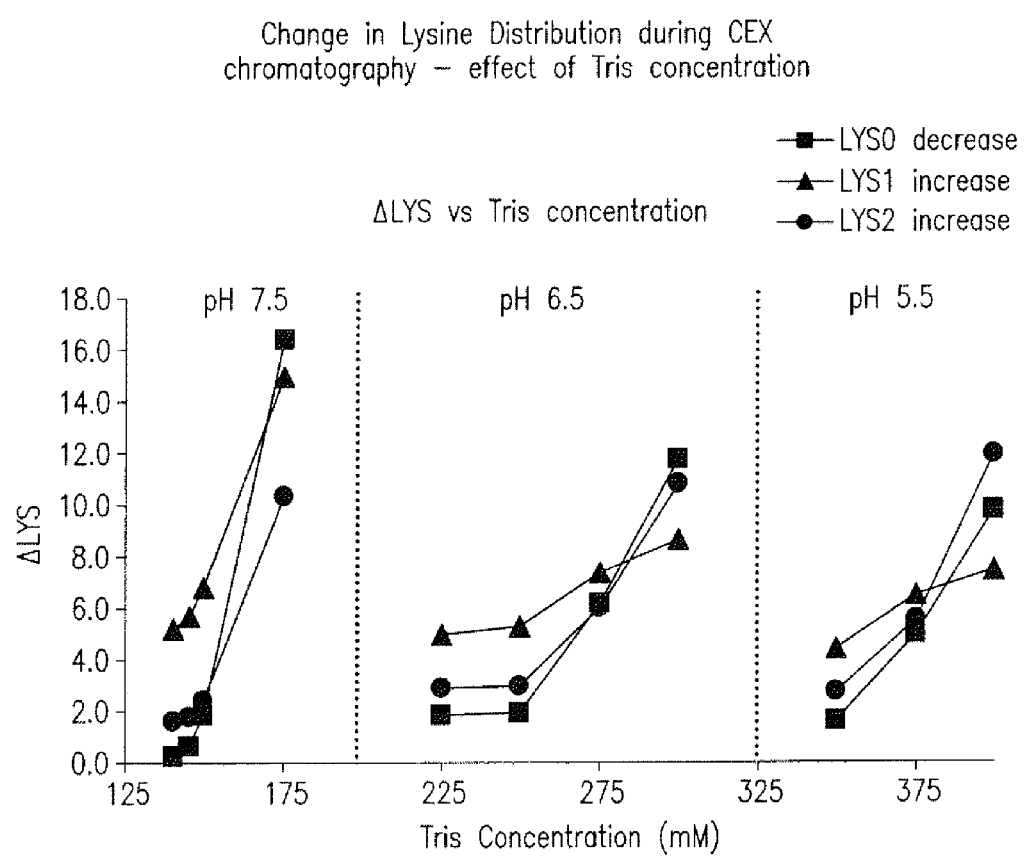
FIG. 9 depicts the change in Lysine distribution during CEX chromatography, highlighting the effect of Tris concentration.

The strategy outlined in Example 6.2.1. to reduce acidic species also can be used to modulate the distribution of C-terminal Lys variants of monoclonal antibodies, a known post-translational modification leading to charge heterogeneity. Some minor changes in the distribution of Lys isoforms is expected through the reduction of acidic species as the WCX analysis is a compositional analysis. However, through careful control of buffer cation type, concentration and pH care, in addition to reducing acidic species, the elution pool can be enriched for the more basic isoforms (Lys 1 and Lys2). Table 35 and FIG. 9 depicts a non-limited example of the impact of pH and cation (Tris) concentration on basic isoform enrichment.

TABLE 35

Change in Lysine distribution during CEX Chromatography - impact of Tris concentration

| % LYS0 decrease | % LYS1 Increase | % LYS2 Increase | Buffer System | Buffer Concentration (mM) | pH |
|---|---|---|---|---|---|
| 1.6 | 4.4 | 2.7 |  | 350 | 5.5 |
| 5 | 6.5 | 5.5 |  | 375 |  |
| 9.7 | 7.5 | 11.9 |  | 400 |  |
| 1.9 | 5 | 2.9 |  | 225 |  |
| 1.9 | 5.3 | 3 |  | 250 |  |
| 6.1 | 7.4 | 6 |  | 275 |  |
| 11.8 | 3.6 | 10.8 |  | 300 |  |
| 0.2 | 5.2 | 1.6 |  | 140 | 7.5 |
| 0.6 | 5.7 | 1.8 |  | 145 |  |
| 1.8 | 6.8 | 2.4 |  | 150 |  |
| 16.4 | 14.9 | 10.3 |  | 175 |  |

6.2.11. Example CEX 11: Demonstration of HCP and Aggregate Reduction in Addition to AR Reduction In the present invention, it has been demonstrated that HCP and aggregate levels can be effectively reduced by appropriate adjustment of the elution conditions, after washing off the AR enriched species in the flow through/wash fractions.

Table 36 and Table 37 shows the HCP and aggregate removal achieved along with AR reduction. The data clearly shows that other process related and product related substances/impurities can be achieved using the current invention on the CEX adsorbents, and hence functions as an effective polishing step in the large scale purification of monoclonal antibodies.

TABLE 36

Aggregate removal during CEX Chromatography

| Resin | Molecule | Buffer system | pH | % Aggregate Reduction | % Fragment Reduction | % Monomer Increase |
|---|---|---|---|---|---|---|
| CM Hyper D | adalimumab | 5 mM Ammonium Sulfate | 7.5 | 0.04 | 0.17 | 0.2 |
| | | 45 mM Tris Acetate | | 0.01 | 0.18 | 0.19 |
| Nuvia S | | 11.5 mM Ammonium Sulfate | | 0.16 | 0.17 | 0.33 |
| | | 75 mM Tris Acetate | | 0.09 | 0.11 | 0.2 |
| | | 22.5 mM Sodium Chloride | | 0.08 | 0.19 | 0.27 |
| Poros XS | | 27 mM Ammonium Sulfate | | 0.75 | 0.27 | 1.02 |
| | | 140 mM Tris Acetate | | 0.51 | 0.41 | 0.92 |
| | | 145 mM Tris Acetate | | 0.58 | 0.41 | 0.98 |
| Nuvia S | mAb B | 85 mM Tris Acetate | | 0.19 | 0.27 | 0.47 |
| Poros XS | | 130 mM Tris Acetate | | 0.36 | 0.04 | 0.39 |
| Nuvia S | mAb C | 35 mM Tris Acetate | 6.0 | 0.07 | 0.01 | 0.07 |
| Poros XS | | 50 mM Tris Acetate | | 0.27 | 0 | 0.28 |

TABLE 37

HCP Removal during CEX Chromatography

| Resin | Molecule | Buffer system | pH | Load HCP (ng/mg) | Eluate Pool HCP (ng/mg) | Reduction fold |
|---|---|---|---|---|---|---|
| CM Hyper D | adalimumab | 5 mM Ammonium Sulfate | 7.5 | 8105 | 3844 | 2.1 |
| | | 45 mM Tris | | 8628 | 5615 | 1.5 |
| Nuvia S | | 11.5 mM Ammonium Sulfate | | 5314 | 2405 | 2.2 |
| | | 75 mM Tris Acetate | | 17317 | 12845 | 1.4 |
| | | 22.5 mM Sodium Chloride | | 9091 | 4115 | 2.2 |
| Poros XS | | 27 mM Ammonium Sulfate | | 21857 | 12574 | 1.0 |
| | | 140 mM Tris Acetate | | 14732 | 9181 | 1.7 |
| | | 145 mM Tris Acetate | | 15359 | 10113 | 1.6 |
| Nuvia S | mAb B | 85 mM Tris Acetate | | 735 | 319 | 2.3 |
| Poros XS | | 130 mM Tris Acetate | | 2183 | 404 | 5.4 |
| Nuvia S | mAb C | 35 mM Tris Acetate | 6.0 | 27 | 31 | 0.9 |
| Poros XS | | 50 mM Tris Acetate | | 25 | 15 | 1.7 |

6.2.11. Example CEX 12 Demonstration of Means of Controlling AR Reduction

Controlling the final product quality by modifying the process based on the quality of the intermediate material is an approach that has been proposed as an effective way of ensuring product quality, with the view of ensuring safety and efficacy.

Considering that the AR levels generated during cell culture and other upstream steps can be variable, it is desirable to design a downstream process step that implements a means of controlling the product quality; and to further have a specific means of controlling a process parameter to influence the quality of the product.

In the current invention, such a control is possible, as the cation concentration is a single parameter that can be modified to achieve a desired separation of the AR species. For example, to achieve a higher level of AR reduction, the Tris concentration of the loading material and the wash buffer can be decreased, such that the AR enriched species is collected in the flow through fraction.

As an example, and not to be restrictive in any manner, it has been demonstrated in this example that the AR levels can be controlled by changing the Tris concentration of the load and wash solutions. A pilot scale Poros XS column (10 cm diameter×22 cm height, 1.7 L), was used for this study.

The load material and the stock buffer are both prepared at 300 mM Tris concentration at the same pH. The AR level of the load material was measured to be X %. The load material and equilibration/wash buffer are in-line diluted to the target Tris concentration based on predetermined correlation between the AR levels and Tris concentration. As demonstrated in the example, when the Tris concentration was adjusted to 156 mM, a final AR reduction of 4.1% was achieved, whereas when the Tris conc. was adjusted to 150 mM, a final AR level of 3.1 was achieved etc (Table 38). This allows very predictable control of the AR levels ensuring achievement of the desired product quality.

TABLE 38

Controlling AR Reduction using Process Analytical Technology approach

| Tris conc (mM) | Yield (%) | % AR Reduction |
|---|---|---|
| 156 | 51.9 | 4.1 |
| 150 | 70.5 | 3.1 |
| 131 | 95.3 | 1.3 |

In addition to the acidic species reduction demonstrated in Example CEX 1 through careful control of the pH cation type and concentration in the load (process stream) and equilibration/wash buffers, the composition of the elution buffer can also be used to further improve the product quality profiles. The impact of various cation types, concentration and pH were tested for eluting the product. There is a wide selection for elution buffer as shown in Table 39. The experiments were performed using Poros XS resin

TABLE 39

Elution buffer types on aggregates removal

| Buffer System | pH | Yield (%) | % Aggregate Reduction |
|---|---|---|---|
| 200 mM Sodium Sulfate/29 mM Tris Acetate | 5.2 | 76.1 | 0.36 |
| 160 mM Sodium Sulfate/29 mM Tris Acetate | 5.2 | 82.3 | 0.82 |
| 150M Sodium Sulfate/29 mM Tris Acetate | 5.2 | 78.8 | 0.90 |
| 140M Sodium Sulfate/29 mM Tris Acetate | 5.2 | 78.2 | 1.00 |
| 400 mM Sodium Sulfate/29 mM Tris Acetate | 4.0 | 78.5 | 0.98 |
| 100 mM Sodium Sulfate/140 mM Tris Acetate | 5.2 | 70.9 | 1.25 |
| 150 mM Sodium Sulfate/140 mM Tris Acetate | 5.2 | 79.6 | 1.05 |
| 140M Sodium Sulfate/140 mM Tris Acetate | 5.2 | 75.4 | 1.07 |
| 130 mM Sodium Sulfate/140 mM Tris Acetate | 5.2 | 78.2 | 1.07 |
| 300 mM Sodium Sulfate/30 mM Tris Acetate | 4.6 | 80.3 | 0.57 |
| 150 mM Sodium Sulfate/29 mM Tris Acetate | 7.5 | 75.0 | 0.92 |

6.2.13. Example CEX 13 Demonstration of Ar Reduction with Cation-Hic Mixed Mode Resin The strategy outlined in Example 6.2.1. to reduce acidic species through careful control of buffer cation type, concentration and pH can be expanded to include other chromatography adsorbents such as mixed mode or multi-modal absorbents which include a cation exchange mechanism. Table 40 outlines the conditions used and the AR reduction achieved for two cation-hydrophobic interaction mixed mode resins. The data clearly shows that the technology outlined in Example 6.2.1. is robust in delivering AR reduction for these types of resins across in addition to traditional cation exchange adsorbents. As described in Example 6.2.1, the AR reduction can be balanced with recovery and an optimal condition can be chosen. As a further demonstration, molecule 2 was also evaluated (Table 41) with the same outcome showing the same relationship between cation concentration, recovery and AR reduction. As previously shown in Example 6.2.6, the optimal condition for different molecules varies. Furthermore, this technology when applied to CEX-HIC mixed mode resins also shows reduction of impurities as previously described.

TABLE 40

Adalimumab AR Reduction by Cation Exchange Mixed Mode Chromatography

| Resin | Buffer System | Tris Concentration (mM) | pH | Yield (%) | % AR Reduction |
|---|---|---|---|---|---|
| Nuvia C Prime | Tris | 70 | 7.5 | 63.8 | 6.5 |
|  | Acetate | 72.5 | 7.5 | 61.1 | 6.0 |
|  |  | 75 | 7.5 | 57.1 | 6.7 |
| Toyo Pearl MX Trp 650M | | 75 | 7.5 | 80 | 5.7 |
|  |  | 80 | 7.5 | 66.7 | 7.2 |
|  |  | 85 | 7.5 | 51.8 | 8.6 |

TABLE 41

Molecule B AR Reduction by Cation Exchange Mixed Mode Chromatography

| Resin | Buffer System | Concentration (mM) | pH | Yield (%) | % AR Reduction |
|---|---|---|---|---|---|
| Nuvia C Prime | Tris Acetate | 75 | 7.5 | 86.0 | 2.0 |
| | | 85 | 7.5 | 74.6 | 5.9 |
| | | 95 | 7.5 | 61.3 | 6.8 |
| Toyo Pearl MX Trp 650M | | 90 | 7.5 | 81.1 | 6.4 |
| | | 95 | 7.5 | 68.8 | 8.8 |
| | | 100 | 7.5 | 53.5 | 10.7 |

As described in previous sections, the Acidic Region for Adalimumab is further grouped into two regions termed AR1 and AR2, based on a certain retention time of the peaks seen on the WCX-10 method. The characteristics of the variants in these two regions are expected to be different and hence the methods that reduce variants belonging to these groups can be specifically delineated.

Further, in addition to achieving a certain AR reduction, it may be desirable to achieve a certain absolute level of AR levels, in consideration of reducing or removing certain variants. The capability of the current invention in achieving a certain absolute level of AR, AR1 and AR2 is demonstrated in Table 42A with Tables 42B and 42C indicating the levels of additional process-related impurities or product-related substances.

The specific species comprising the AR1 species can be identified and quantitated, to demonstrate reduction of such species by methods of the current invention. While these species are among the Acidic Species part of the charge variants, the acidic species typically described in the literature is the deamidated mAb, which is distinctly different. These results show that the Cation Exchange Resin with additional pendant hydrophobic interaction functionality, is able to provide AR reduction effectively, similar to the CEX Adsorbents.

TABLE 42A

Final acidic species level for Adalimumab

| Resin | Buffer System | Tris Concentration (mM) | pH | Yield (%) | Final % AR1 | Final % AR2 | Final % AR |
|---|---|---|---|---|---|---|---|
| Nuvia C Prime | Tris Acetate | 70 | 7.5 | 63.8 | 0.39 | 4.64 | 5.03 |
| | | 72.5 | 7.5 | 61.1 | 0.36 | 4.4 | 4.75 |
| | | 75 | 7.5 | 63.8 | 0.39 | 4.06 | 4.45 |
| Toyo Pearl MX Trp 650M | | 75 | 7.5 | 80 | 0.6 | 4.2 | 4.8 |
| | | 80 | 7.5 | 66.7 | 0.5 | 3.2 | 3.7 |
| | | 85 | 7.5 | 51.8 | 0.2 | 2.2 | 2.4 |

TABLE 42B

Aggregates/Fragments Reduction by Cation Exchange Mixed Mode Chromatography

| Resin | Molecule | Buffer System | pH | % Aggregate Reduction | % Fragment Reduction | % Monomer Increase |
|---|---|---|---|---|---|---|
| Nuvia C prime | adalimumab | 70 mM Tris | 7.5 | 0.3 | 0.34 | 0.63 |
| Toyo Pearl MX Trp 650M | | 75 mM Tris | | 0.08 | 0.56 | 0.65 |
| Nuvia C prime | Molecule B | 85 mM Tris | | 0.87 | 1.18 | 2.04 |
| Toyo Pearl MX Trp 650M | | 95 mM Tris | | 0.0 | 1.8 | 1.8 |

TABLE 4C

HCP Reduction by Cation Exchange Mixed Mode Chromatography

| Resin | Compound | Buffer | pH | Load HCP (ng/mg) | Eluate pool HCP (ng/mg) | Fold Reduction |
|---|---|---|---|---|---|---|
| Toyo Pearl MX Trp 650M | adalimumab | 70 mM Tris | 7.5 | 202.6 | 38.9 | 5.2 |
| Nuvia C prime | | 75 mM Tris | | 205.5 | 72.8 | 2.8 |
| Toyo Pearl MX Trp 650M | Molecule B | 95 mM Tris | | 983.3 | 137.1 | 7.2 |
| Nuvia C prime | | 85 mM Tris | | 1011.3 | 88.2 | 11.5 |

6.2.14. Example CEX 14 Demonstration of Ar Reduction in Process Combinations The method described above for reducing acidic species using cation exchange can be used as an independent operation or in combination with other process steps that provide additional acidic species reduction or those providing additional complementary and supplementary purification (See tables 43-50). The following process combinations are provided here as non-limiting examples 1. Affinity→MM→CEX
2. Affinity→AEX→CEX
3. Affinity→CEX
4. CEX Capture→CEX

TABLE 43

AR Reduction by Capto Adhere(mixed mode) followed by Poros XS (CEX)
Capto Adhere CEX Cycle B

| Step | Yield % | % AR1 | % AR | % AR1 Reduction | % AR Reduction |
|---|---|---|---|---|---|
| MabSure Eluate | | 2.90 | 10.08 | | |
| Viral Inact | 89 | 2.89 | 10.42 | | |
| Mixed Mode FTW | 94 | 2.26 | 8.52 | 0.64 | 1.90 |
| CEX Load | | 2.29 | 8.97 | | |
| CEX Eluate | 91 | 0.25 | 4.88 | 2.04 | 4.10 |
| Overall | 76 | | | 2.65 | 5.20 |

TABLE 44

Aggregate reduction by combination of Capto Adhere(mix mode) Poros XS (CEX)
Capto Adhere CEX Cycle B

| Step | Yield % | % Monomer | % Aggregate | % Fragment | % Mono increase | % Agg. decrease | % Frag decrease |
|---|---|---|---|---|---|---|---|
| MabSure Eluate | | 99.08 | 0.85 | 0.08 | | | |
| Viral Inact | 89 | 99.14 | 0.73 | 0.13 | | | |
| Mixed Mode FTW | 96 | 99.64 | 0.26 | 0.10 | 0.50 | 0.47 | 0.03 |
| CEX Load | | 99.64 | 0.26 | 0.10 | | | |
| CEX Eluate | 89 | 99.74 | 0.18 | 0.08 | 0.10 | 0.08 | 0.02 |
| overall | 76 | | | | 0.66 | 0.67 | 0.00 |

TABLE 45

AR Reduction by Poros PI (AEX) followed by Poros XS (CEX)
AEX CEX Cycle C

| Step | Yield % | % AR1 | % AR | % AR1 Reduction | % AR Reduction |
|---|---|---|---|---|---|
| MabSure Eluate | | 2.90 | 10.08 | | |
| AEX Load | | 2.73 | 10.16 | | |
| AEX FTW | 90 | 1.64 | 6.7 | 1.09 | 3.46 |
| Viral Inact | 100 | 1.39 | 6.03 | | |
| CEX Load | | 2.76 | 6.18 | | |
| CEX Eluate | 91 | 0.15 | 3.22 | 2.61 | 2.96 |
| Overall | 82 | | | 2.75 | 6.86 |

TABLE 46

Aggregate reduction Poros PI (AEX) Poros XS (CEX)
AEX CEX Cycle C

| Step | Yield % | % Monomer | % Aggregate | % Fragment | % Mono increase | % Agg. decrease | % Frag decrease |
|---|---|---|---|---|---|---|---|
| MabSure Eluate | | 99.08 | 0.85 | 0.08 | | | |
| AEX Load | | 98.67 | 1.25 | 0.03 | | | |
| AEX FTW | 90 | 99.88 | 0.05 | 0.07 | 1.21 | 1.2 | −0.04 |
| Viral Inact | 100 | 99.94 | 0.05 | 0.02 | | | |
| CEX Load | | 99.64 | 0.26 | 0.10 | | | |
| CEX Eluate | 91 | 99.79 | 0.13 | 0.08 | 0.14 | 0.13 | 0.02 |
| Overall | 82 | | | | 0.71 | 0.72 | 0.00 |

TABLE 47

AR reduction from a Affinity capture pool followed by Poros XS (CEX)

| Step | Yield % | % AR1 | % AR | % AR1 Reduction | % AR Reduction |
|---|---|---|---|---|---|
| MabSure Eluate | | 3.0 | 10.5 | | |
| CEX Eluate | 82.7 | 0.3 | 4.9 | 2.8 | 5.6 |

TABLE 48

Aggregate reduction: Affinity capture pool followed by Poros XS (CEX)

| Step | Yield % | % Monomer | % Aggregate | % Fragment | % Mono increase | % Agg. decrease | % Frag decrease |
|---|---|---|---|---|---|---|---|
| MabSure Eluate | | 98.5 | 1.4 | 0.1 | | | |
| CEX Eluate | 82.7 | 99.7 | 0.2 | 0.1 | 1.2 | 1.2 | 0.0 |

TABLE 49

AR reduction CEX Capture (Fractogel SO3) followed by Poros XS (CEX) 145 mM TA Poros XS D2E7

| Step | Yield % | % AR1 | % AR | % AR1 Reduction | % AR Reduction |
|---|---|---|---|---|---|
| Concentrated Fractogel Eluate VI | | 3.3 | 14.0 | | |
| CEX Eluate | 72.6 | 0.44 | 6.7 | 2.8 | 7.3 |

TABLE 50

Aggregate reduction: CEX Capture (Fractogel) followed by Poros XS (CEX) 145 mM TA Poros XS D2E7

| Step | Yield % | % Monomer | % Aggregate | % Fragment | % Mono increase | % Agg. decrease | % Frag decrease |
|---|---|---|---|---|---|---|---|
| Concentrated Fractogel Eluate VI | | 97.9 | 1.5 | 0.7 | | | |
| CEX Eluate | 72.6 | 98.7 | 1.1 | 0.2 | 0.9 | 0.4 | 0.5 |

6.3. Mixed Mode Chromatography Examples

6.3.1. Example M M1: Resin: Buffer Combination

In this example one of the approaches outlined in the general description was employed to determine the operating conditions to implement the invention. Specifically, a response surface design DOE was applied to evaluate mAb AR reductions and recovery yields.

Figure 10:
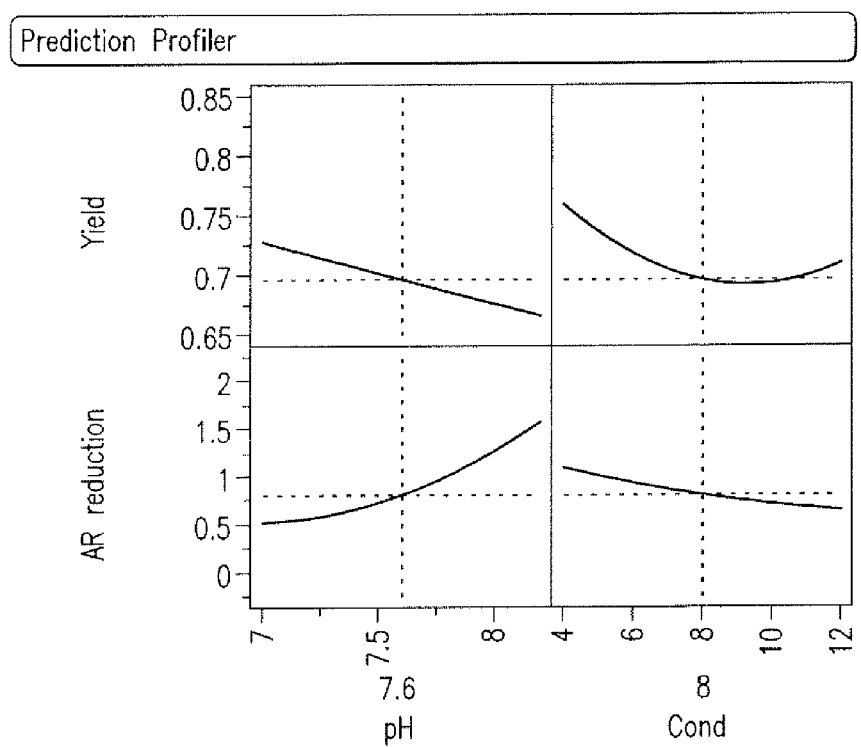
FIG. 10 depicts the effect of pH and conductivity on Adalimumab AR reduction and recovery yield in the context of MM chromatography.

The demonstration of the current invention for a specific antibody & resin is provided in this example, and consists of 1. Choosing a pH in the range of 6.8 to 8.4.
2. Choosing a conductivity in the range of 2.3 to 13.7 mS/cm.
3. Determining the acidic species distribution in the ft/wash fractions.
4. Choosing an optimal pH and conductivity that provides the desired acidic species levels and recovery In this example, Adalimumab and resin Capto Adhere were chosen. The experiments were performed with Tris/Acetate buffer system at target pH and conductivity listed in Table 51 The load material was from Protein A affinity capture and pH adjusted. This study demonstrated the effect of loading pH and conductivity on acidic species reduction. The acidic species reduction can be significantly affected by operating pH. AR reduction increased with increasing pH and/or decreasing conductivity (Table 51, Table 52 and FIG. 10)

TABLE 51

DOE study condition

| Tris Acetate Buffer | Range | Edge points for Response Surface |
|---|---|---|
| pH | 7.0-8.2 | 6.8, 8.4 |
| Conductivity | 4.0-12.0 | 2.3, 13.7 |

TABLE 52

DOE Study Operating Conditions and Results

| DOE exp | pH | Conductivity (mS/cm) | ΔAR (%) | Yield (%) |
|---|---|---|---|---|
| 1 | 7.0 | 4.0 | 0.4 | 83 |
| 2 | 7.6 | 8.0 | 0.4 | 73 |
| 3 | 7.6 | 2.3 | 1.3 | 82 |
| 4 | 7.6 | 8.0 | 0.6 | 68 |
| 5 | 7.6 | 8.0 | 0.2 | 70 |
| 6 | 7.6 | 8.0 | −0.2 | 69 |
| 7 | 8.2 | 4.0 | 2.1 | 67 |
| 8 | 7.6 | 8.0 | 1.3 | 69 |
| 9 | 7.0 | 12.0 | −0.2 | 70 |
| 10 | 7.6 | 8.0 | 1.2 | 71 |
| 11 | 8.2 | 12.0 | 1.4 | 74 |
| 12 | 6.8 | 8.0 | 1.2 | 76 |
| 13 | 8.4 | 8.0 | 1.8 | 67 |
| 14 | 7.6 | 8.0 | 1.4 | 71 |

TABLE 52-continued

DOE Study Operating Conditions and Results

| DOE exp | pH | Conductivity (mS/cm) | ΔAR (%) | Yield (%) |
|---|---|---|---|---|
| 15 | 7.6 | 13.7 | 1.0 | 74 |
| 16 | 7.6 | 8.0 | 1.6 | 70 |

Note:
AR reductions and protein recovery yields were calculated based on the Flow Through fractions at about loading 200 g protein per L of resin.

6.3.2. Example MM 2: Fraction Pooling

Figure 11:
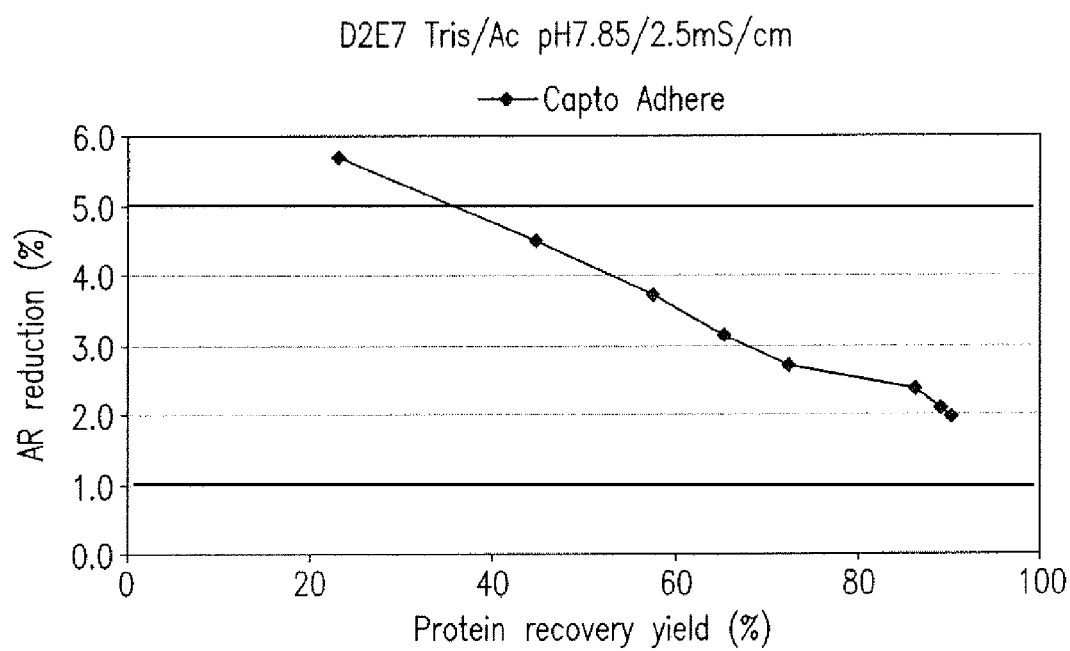
FIG. 11 depicts the AR reduction achieved with the corresponding protein recovery in the context of MM chromatography.
Figure 12:
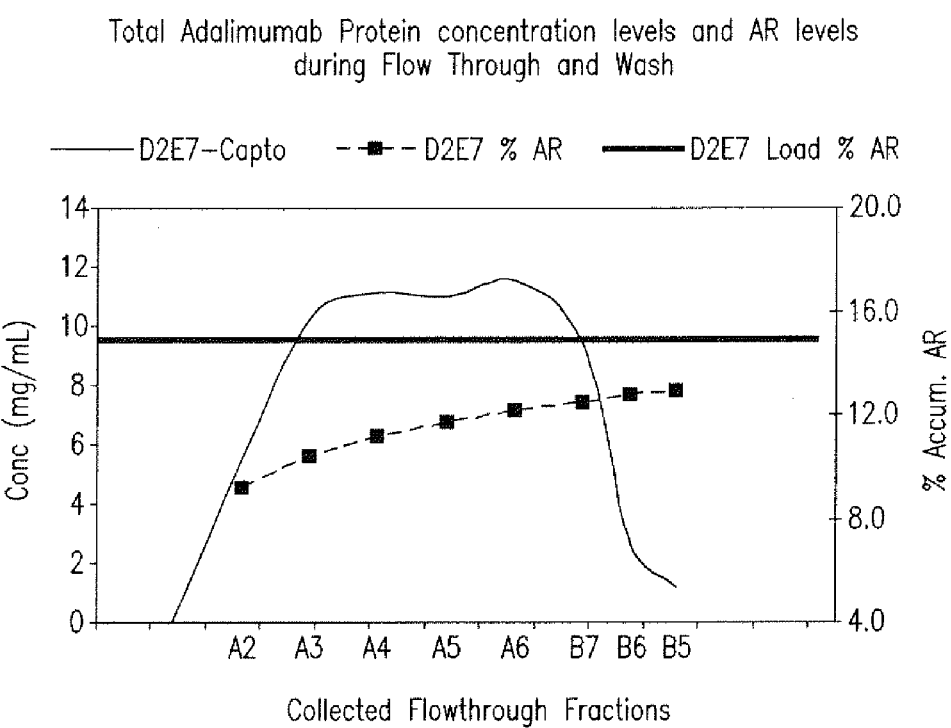
FIG. 12 depicts the total Adalimumab Protein concentration levels and AR levels during Flow Through and Wash.

In this example, Adalimumab and resin Capto Adhere were chosen. The experiments were performed with Tris/Acetate buffer system at pH 7.85 and conductivity of 2.5 mS/cm. The load material was from Protein A affinity capture and pH adjusted. Column flow through was fractionated throughout the entire load and wash phases. Each fraction was analyzed for acidic species and protein recovery. FIG. 11, FIG. 12 and Table 53 demonstrate AR reduction achieved with the corresponding recovery. These AR reductions and recoveries correspond to the cumulative pools of the fractions from the start to the various points during the load/wash. This is depicted in Table 53 where the AR reductions corresponding to each of these pools. This data is plotted in FIG. 11.

TABLE 53

Cumulative AR reduction in Flowthrough/wash fractions

| Flowthrough Fraction (Load & wash) | Yield (%) | Δ AR1 (%) | Δ AR2 (%) | Δ AR (%) | ΔLys (%) |
|---|---|---|---|---|---|
| A2 | 23 | 2.56 | 3.13 | 5.69 | 5.61 |
| A2 + A3 | 45 | 2.31 | 2.19 | 4.49 | 4.37 |
| A2 + A3 + A4 | 58 | 1.83 | 1.89 | 3.72 | 3.63 |
| A2 + A3 + A4 + A5 | 65 | 1.57 | 1.58 | 3.15 | 3.06 |
| A2 + A3 + A4 + A5 + A6 | 73 | 1.38 | 1.32 | 2.70 | 2.61 |
| A2 + A3 + A4 + A5 + A6 + B7 | 86 | 1.26 | 1.12 | 2.38 | 2.30 |
| A2 + A3 + A4 + A5 + A6 + B7 + B6 | 89 | 1.19 | 0.91 | 2.09 | 2.02 |
| A2 + A3 + A4 + A5 + A6 + B7 + B6 + B5 | 90 | 1.14 | 0.82 | 1.96 | 1.89 |

Note:
"A" Fractions are load fractions and "B" Fractions are wash fractions

6.3.3. Example M M 3: Demonstration of AR Reduction with Mixed Mode Adsorbents In this example, Adalimumab was chosen. The experiments were performed with Tris/Acetate buffer system at pH 7.85 and conductivity of 2.5, 3.5, and 4.5 mS/cm. The same load material was applied to different mixed mode resin columns. The load material was from Protein A affinity capture and pH adjusted. Table 54 shows that all three mixed mode resins could reduce mAb acidic species. Due to the differences of resin ligands, the AR reduction level may slightly vary under certain conditions.

TABLE 54

Adalimumab AR Reduction and Protein Recovery Yields Processed with Different Mixed Mode media

| | Tris/Ac Buffer | | | | | | | | |
|---|---|---|---|---|---|---|---|---|---|
| | Capto Adhere pH 7.85 | | | HEA pH 7.85 | | | PPA pH 7.85 | | |
| Operating Conditions | 4.5 mS/cm | 3.5 mS/cm | 2.5 mS/cm | 4.5 mS/cm | 3.5 mS/cm | 2.5 mS/cm | 4.5 mS/cm | 3.5 mS/cm | 2.5 mS/cm |
| Yield (%) | 50 | 52 | 58 | 49 | 52 | 56 | 40 | 43 | 47 |
| AR Reduction (%) | 1.8 | 3.8 | 3.7 | 1.1 | 2.7 | 3.2 | 1.4 | 2.2 | 3.5 |
| Yield (%) | 68 | 71 | 73 | 65 | 75 | 69 | 61 | 64 | 63 |
| AR Reduction (%) | 1.1 | 2.7 | 2.7 | 0.5 | 1.8 | 2.1 | 0.4 | 1.9 | 2.6 |

6.3.4. Example MM 4 Demonstration of Ar Reduction with Other Antibodies: mAb B And mAb C In this example, another two different monoclonal antibodies besides Adalimumab and resin Capto Adhere was chosen. The experiments were performed with Tris/Acetate buffer system at multiple pH and conductivity condition. The load materials of all mAbs were from Protein A affinity capture and pH adjusted. MAB C was also applied to another two MM resins besides Capto Adhere under the same operating conditions. The Table 55 outlines the operating conditions and the AR reduction achieved and the corresponding recovery achieved. The results demonstrate that the technology can also reduce acidic species for other monoclonal antibodies with optimal pH and conductivity conditions. Experiments were performed with Tris-acetate buffer system.

TABLE 55

AR Reductions and Protein Recovery for different mAb with Capto Adhere columns

| mAb | pH | conductivity (mS/cm) | ΔAR (%) | Yield (%) |
|---|---|---|---|---|
| D2E7 | 7.85 | 3.5 | 3.8 | 52 |
| | 7.85 | 2.5 | 3.7 | 58 |
| MAB B | 6.8 | 3.0 | 6.3 | 51 |
| | 6.8 | 4.5 | 4.2 | 53 |
| | 7.0 | 3.0 | 5.1 | 77 |
| | 8.0 | 3.0 | 3.4 | 60 |

TABLE 55-continued

AR Reductions and Protein Recovery for
different mAb with Capto Adhere columns

| mAb | pH | conductivity (mS/cm) | ΔAR (%) | Yield (%) |
|---|---|---|---|---|
| MAB C | 9.0 | 3.0 | 5.3 | 73 |
| | 8.5 | 3.0 | 3.5 | 54 |
| | 8.0 | 3.0 | 3.7 | 50 |

Figure 13:
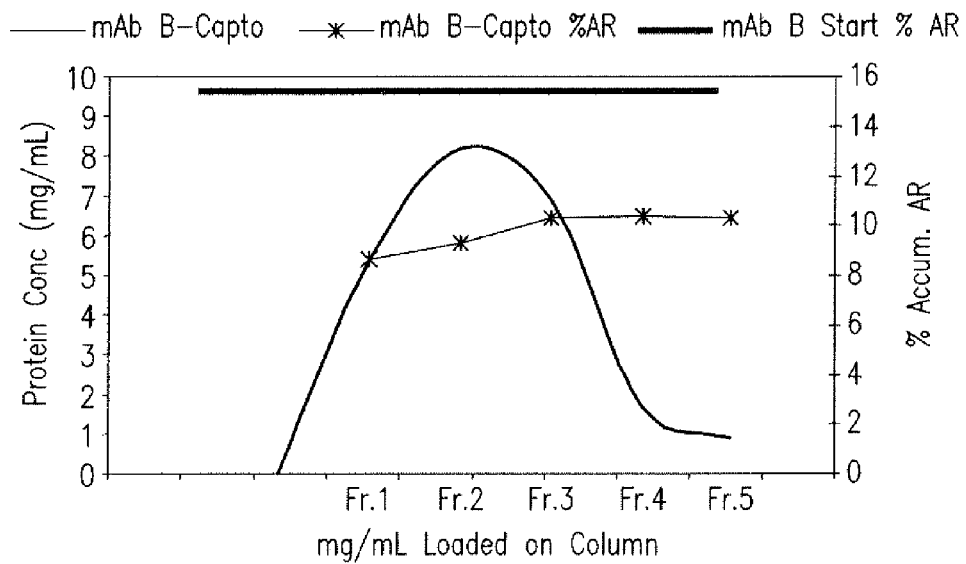
FIG. 13 depicts the total mAb B Protein concentration levels and AR levels during Flow Through and Wash in the context of MM chromatography.
Figure 14:
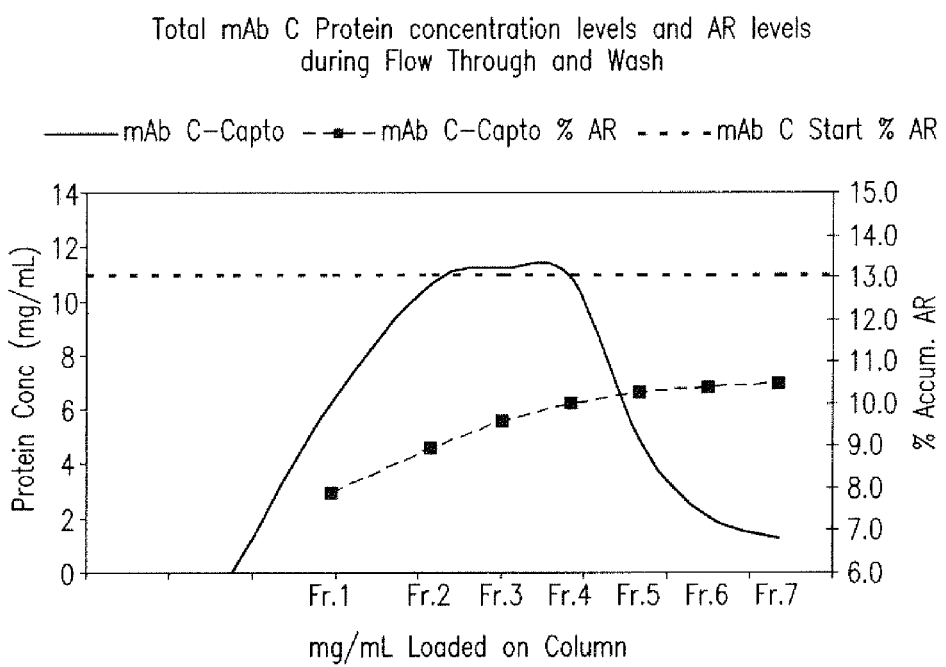
FIG. 14 depicts the total mAb C Protein concentration levels and AR levels during Flow Through and Wash in the context of MM chromatography.
Figure 15:
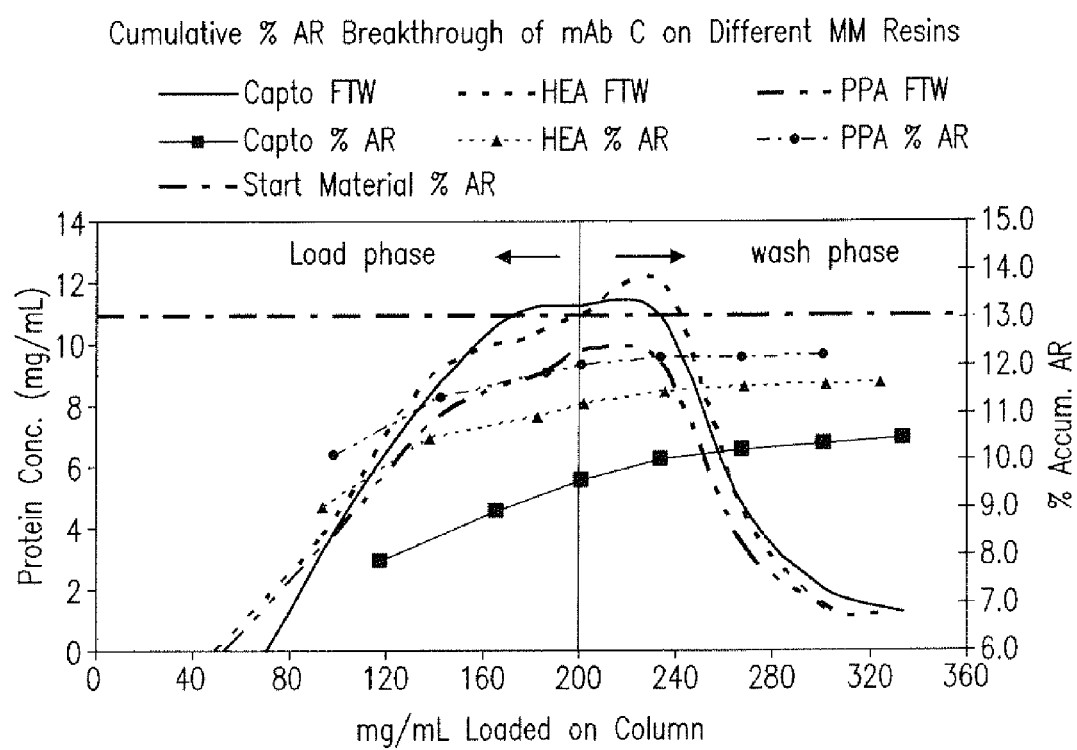
FIG. 15 depicts the Cumulative % AR breakthrough of mAb C on different MM resins.

FIG. 13 displays the MAB B cumulative pool AR broke through the column of Capto Adhere operated at pH 7.0 and conductivity of 3.0 mS/cm with Tris-Acetate buffer. FIG. 14 shows the MAB C cumulative pool AR broke through the column of Capto Adhere operated at pH 8.5 and conductivity of 3.0 mS/cm with Tris-Acetate buffer. Both of graphs demonstrate similar AR breakthrough curves with different AR values comparing to adalimumab (FIG. 12). FIG. 15 presents the AR breakthrough curves of Mab C with three different mixed mode resins with Tris-acetate buffer operated at pH 8.5 and conductivity of 3.0 mS/cm. The data clearly demonstrates that the AR reduction technology using mixed mode resins works very effectively for other antibodies.

Figure 16:
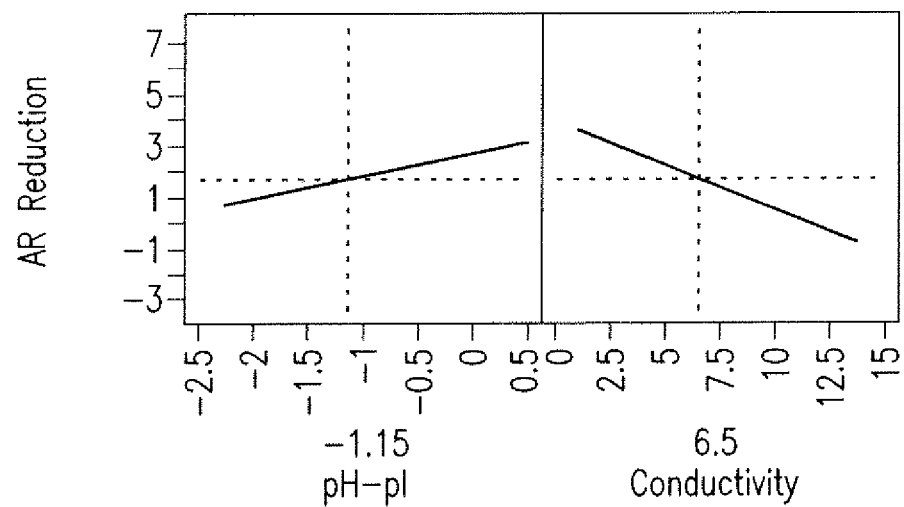
FIG. 16 depicts the impact of pH-pI and Conductivity on D2E7 (Adalimumab) AR Reduction in the context of MM chromatography.
Figure 17:
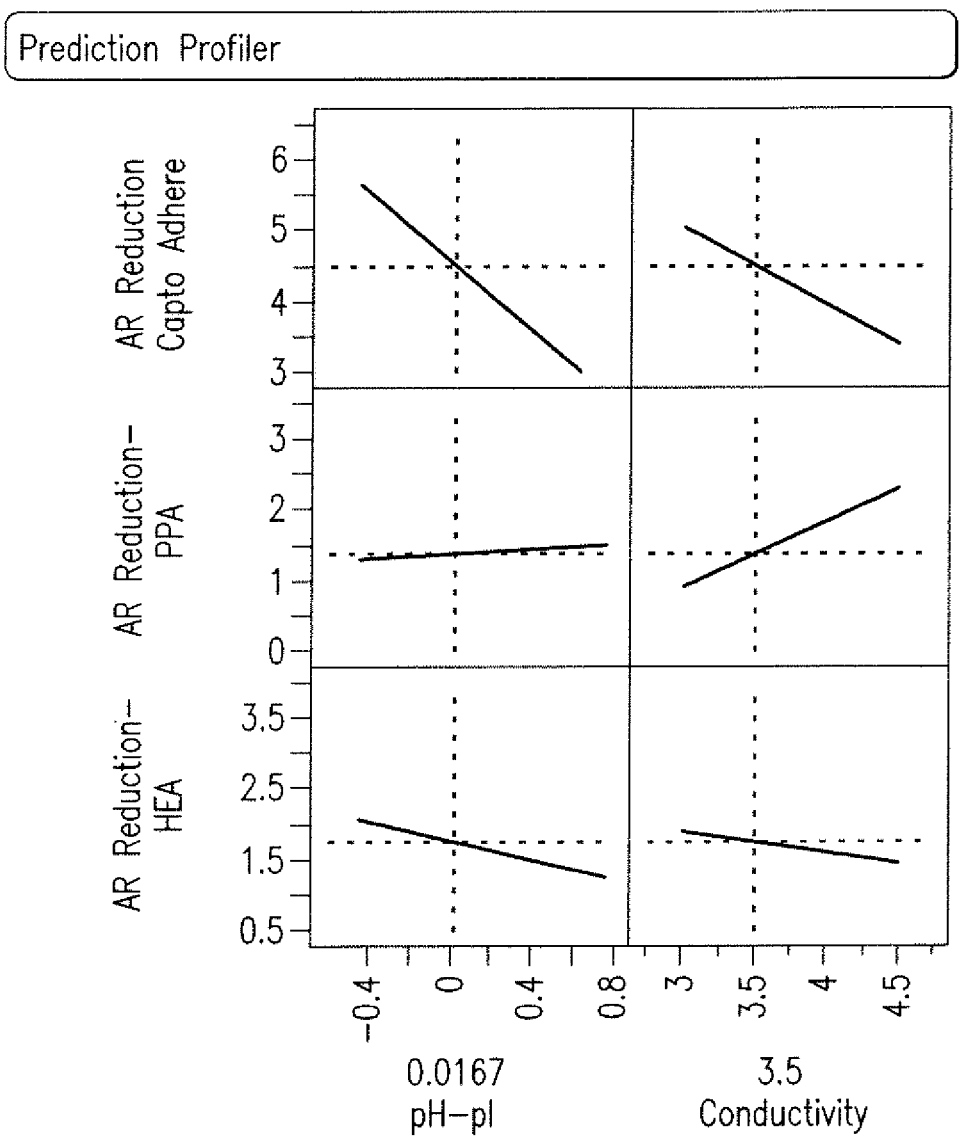
FIG. 17 depicts the impact of pH-pI and Conductivity on mAb B AR Reduction in the context of MM chromatography.
Figure 18:
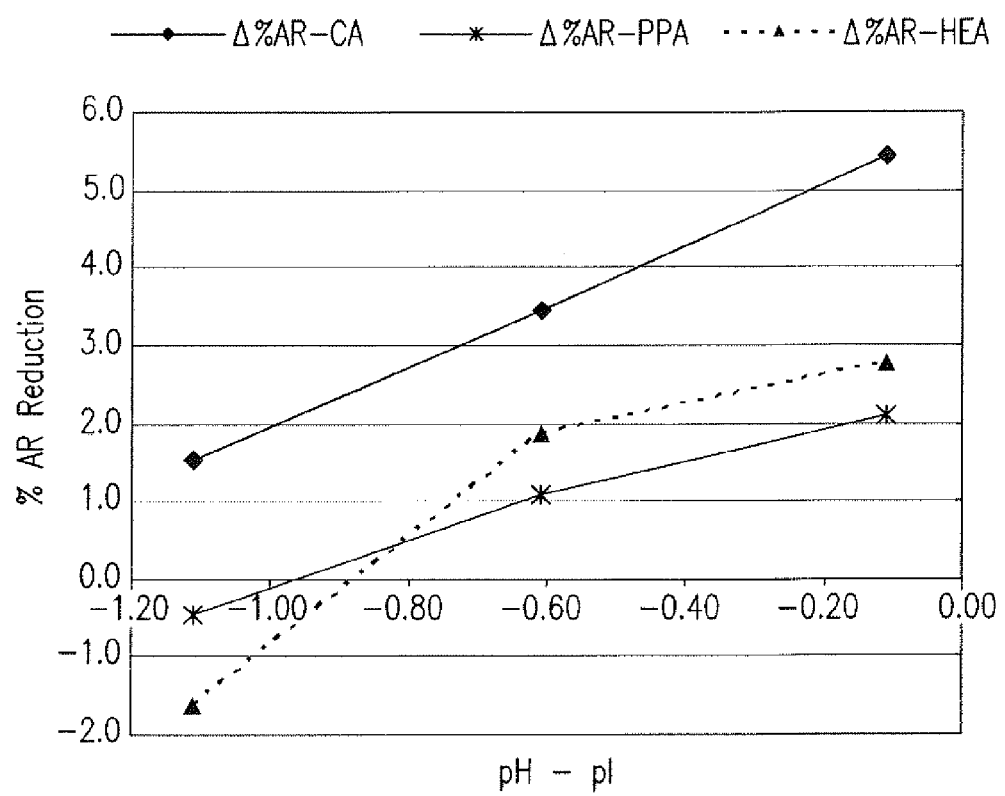
FIG. 18 depicts the impact and trend of pH-pI on mAb C AR reduction with multiple resins in the context of MM chromatography.

6.3.5. Example MM 5: Demonstration of Relative pH on AR Reduction with Different Resins Using D2E7 Antibody Material In this example, data compiled from different experiments is shown to demonstrate the impact of the pH choice, relative to the pI of the protein on AR reduction. This data set provides the basis for one skilled in the art to determine a pH range to implement the current invention. Further, this reiterates the fact that the pH choice depends on several factors and the relationship between pH and AR reduction is also mAb dependent. FIG. 16 demonstrates the impact of pH-pI and conductivity on AR reduction which compiled data from the experiments performed with Capto Adhere under conditions listed in Table 56. FIG. 17 shows the impact of pH-pI and conductivity on MAB B AR reduction including the experiments operated with Tris/Acetate buffer system and multiple mixed mode resins under the conditions listed in Table 57. FIG. 18 shows the impact of pH-pI and conductivity on MAB C AR reduction including the experiments operated with Tris/Acetate buffer system and multiple mixed mode resins under the conditions listed in FIG. 16. All the load materials were from Protein A affinity capture and pH adjusted. It is also clear that the AR reduction can be achieved with the present invention with a range of pH choices, in the range of +0.5 to −2.5 pH units from pI for D2E7. One skilled in the art can choose an appropriate pH to achieve a target AR reduction.

TABLE 56

Operating conditions and AR reductions for D2E7

| Buffer system | pH | pH-pI | Conductivity (mS/cm) | AR reduction |
|---|---|---|---|---|
| Tris/Ac | 7 | −2.02 | 4 | 0.4 |
| | 7.6 | −1.42 | 8 | 0.4 |
| | 7.6 | −1.42 | 2.3 | 1.3 |
| | 7.6 | −1.42 | 8 | 0.6 |
| | 7.6 | −1.42 | 8 | 0.2 |
| | 7.6 | −1.42 | 8 | −0.2 |
| | 8.2 | −0.82 | 4 | 2.1 |
| | 7.6 | −1.42 | 8 | 1.3 |
| | 7 | −2.02 | 12 | −0.2 |
| | 7.6 | −1.42 | 8 | 1.2 |

TABLE 56-continued

Operating conditions and AR reductions for D2E7

| Buffer system | pH | pH-pI | Conductivity (mS/cm) | AR reduction |
|---|---|---|---|---|
| | 8.2 | −0.82 | 12 | 1.4 |
| | 6.8 | −2.27 | 8 | 1.2 |
| | 8.4 | −0.57 | 8 | 1.8 |
| | 7.6 | −1.42 | 8 | 1.4 |
| | 7.6 | −1.42 | 13.7 | 1.0 |
| | 7.6 | −1.42 | 8 | 1.6 |
| | 7.5 | −1.52 | 3.75 | 1.7 |
| | 7.6 | −1.42 | 2.5 | 2.7 |
| | 7.6 | −1.42 | 2.5 | 2.0 |
| | 7.6 | −1.42 | 5 | 1.3 |
| | 7.6 | −1.42 | 5 | 1.1 |
| | 7.85 | −1.17 | 2 | 3.5 |
| | 7.85 | −1.17 | 3.75 | 3.2 |
| | 7.85 | −1.17 | 3.75 | 2.1 |
| | 7.85 | −1.17 | 3.75 | 2.8 |
| | 7.85 | −1.17 | 3.75 | 2.2 |
| | 7.85 | −1.17 | 5.5 | 2.1 |
| | 8.1 | −0.92 | 2.5 | 5.0 |
| | 8.1 | −0.92 | 2.5 | 2.6 |
| | 8.1 | −0.92 | 5 | −0.2 |
| | 8.1 | −0.92 | 5 | −1.1 |
| | 8.2 | −0.82 | 3.75 | 2.9 |
| Arg/Ac | 8.5 | −0.52 | 1 | 6.8 |
| | 9.0 | −0.02 | 1 | 6.5 |
| | 9.5 | 0.48 | 1 | 1.9 |
| Trol/Ac | 7.85 | −1.17 | 1 | 5.7 |
| | 8.0 | −1.02 | 1 | 8.0 |
| | 8.5 | −0.52 | 1 | 6.0 |

TABLE 57

Operating conditions and AR reductions for MAB B

| | pH | pH-pI | Conductivity (mS/cm) | AR reduction |
|---|---|---|---|---|
| Capto Adhere | 6.8 | −0.45 | 3 | 6.3 |
| | 7 | −0.25 | 3 | 6.2 |
| | 7.5 | 0.25 | 3 | 4.0 |
| | 8 | 0.75 | 3 | 3.2 |
| | 6.8 | −0.45 | 4.5 | 4.1 |
| | 7.5 | 0.25 | 4.5 | 3.3 |
| PPA | 6.8 | −0.45 | 3 | 1.1 |
| | 7 | −0.25 | 3 | 0.9 |
| | 7.5 | 0.25 | 3 | 1.3 |
| | 8 | 0.75 | 3 | 0.5 |
| | 6.8 | −0.45 | 4.5 | 1.6 |
| | 7.5 | 0.25 | 4.5 | 3.0 |
| HEA | 6.8 | −0.45 | 3 | 1.8 |
| | 7 | −0.25 | 3 | 1.4 |
| | 7.5 | 0.25 | 3 | 3.6 |
| | 8 | 0.75 | 3 | 0.7 |
| | 6.8 | −0.45 | 4.5 | 2.2 |
| | 7.5 | 0.25 | 4.5 | 0.9 |

TABLE 58

Operating conditions and AR reductions for MAB C

| | pH | pH-pI | Conductivity (mS/cm) | Δ % AR |
|---|---|---|---|---|
| Capto Adhere | 8.0 | −1.11 | 1 | 1.5 |
| | 8.5 | −0.61 | 1 | 3.5 |
| | 9.0 | −0.11 | 1 | 5.4 |
| PPA | 8.0 | −1.11 | 1 | −0.4 |
| | 8.5 | −0.61 | 1 | 1.1 |
| | 9.0 | −0.11 | 1 | 2.1 |
| HEA | 8.0 | −1.11 | 1 | −1.6 |
| | 8.5 | −0.61 | 1 | 1.9 |
| | 9.0 | −0.11 | 1 | 2.8 |

6.3.6. Example MM 6: Effect of pH on AR Reduction

Response surface design DOE was applied to evaluate the impact of pH and conductivity on mAb AR reductions. In this example, Adalimumab and Capto Adhere were chosen. The experiments were performed with Tris/Acetate buffer system. The load material was from Protein A affinity capture and pH adjusted. Besides the pH and conductivity ranged tested and demonstrated in Table 59 and Table 60, higher pH ranges were also studied (FIG. 19).

Figure 19:
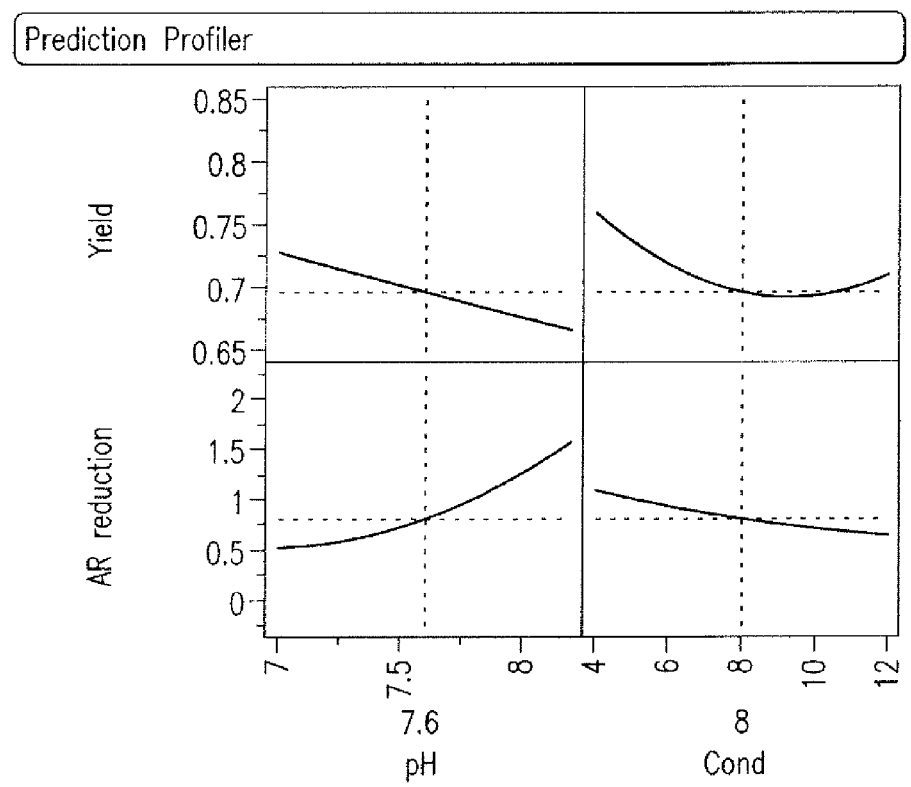
FIG. 19 depicts the effect of pH and Conductivity on AR reduction and Yield in the context of MM chromatography.
Figure 20:
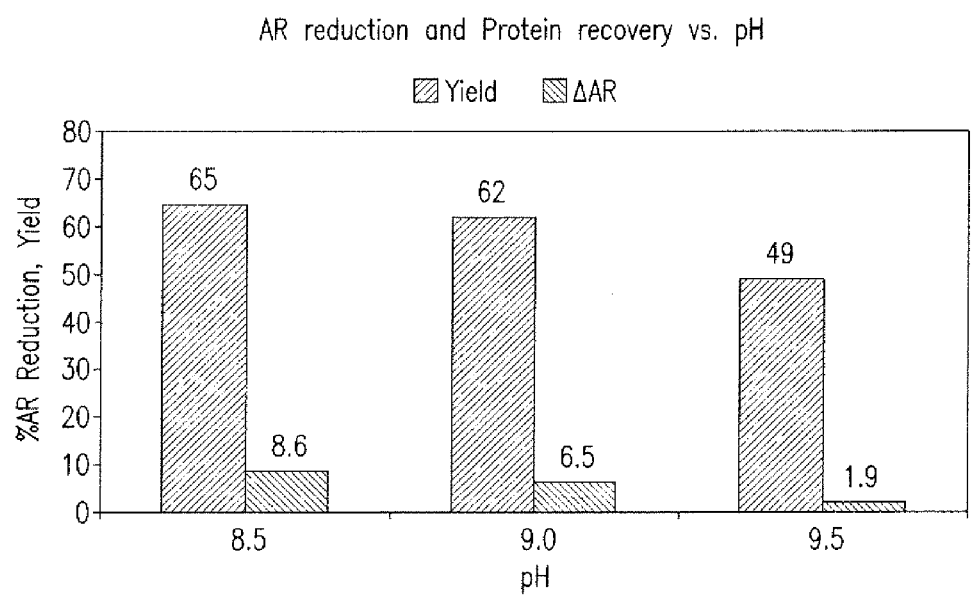
FIG. 20 depicts AR reduction and Protein recovery vs. pH in the context of MM chromatography.

The results in FIG. 19 and FIG. 20 demonstrated that mAb acidic species can be reduced at wide pH range from 6.8 to 9.5.

TABLE 59

DOE study condition

| Tris Acetate Buffer | Range | Edge points for Response Surface |
|---|---|---|
| pH | 7.0-8.2 | 6.8, 8.4 |
| Conductivity | 4.0-12.0 | 2.3, 13.7 |

TABLE 60

AR reduction and Yield in DOE study

| Experiment # | pH | Conductivity | ΔAR | Yield |
|---|---|---|---|---|
| 1 | 7.0 | 4.0 | 0.4 | 83 |
| 2 | 7.6 | 8.0 | 0.4 | 73 |
| 3 | 7.6 | 2.3 | 1.3 | 82 |
| 4 | 7.6 | 8.0 | 0.6 | 68 |
| 5 | 7.6 | 8.0 | 0.2 | 70 |
| 6 | 7.6 | 8.0 | -0.2 | 69 |
| 7 | 8.2 | 4.0 | 2.1 | 67 |
| 8 | 7.6 | 8.0 | 1.3 | 69 |
| 9 | 7.0 | 12.0 | -0.2 | 70 |
| 10 | 7.6 | 8.0 | 1.2 | 71 |
| 11 | 8.2 | 12.0 | 1.4 | 74 |
| 12 | 6.8 | 8.0 | 1.2 | 76 |
| 13 | 8.4 | 8.0 | 1.8 | 67 |
| 14 | 7.6 | 8.0 | 1.4 | 71 |
| 15 | 7.6 | 13.7 | 1.0 | 74 |
| 16 | 7.6 | 8.0 | 1.6 | 70 |

Note:
AR reductions and protein recovery yields were calculated based on the Flow Through fractions at about loading 200 g protein per L of resin

Figure 21:
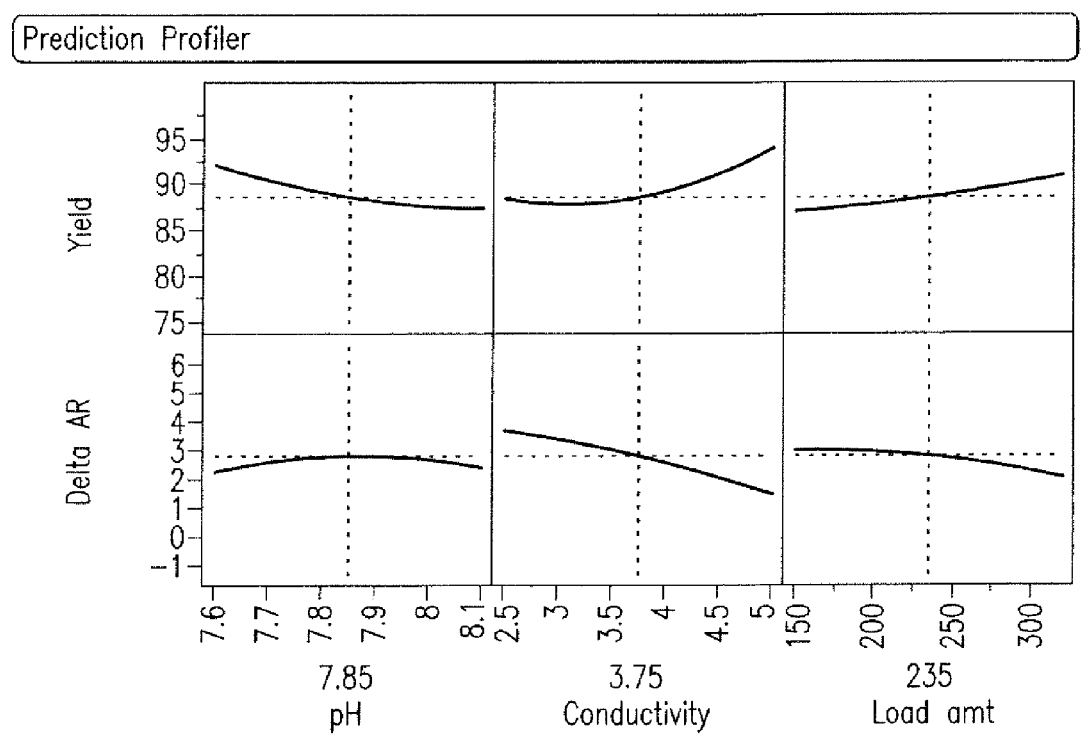
FIG. 21 depicts the effect of pH, conductivity and protein load amount on AR reduction and Yield.

6.3.7. Example MM 7: Demonstration of Ar Reduction with Different Ion Concentrations—Adalimumab In this example, adalimumab was chosen. Besides the conductivity range tested presented before, lower conductivity and higher conductivity ranges were also studied with the Capto Adhere. Table 61 and Table 62 display the DOE study conditions using Capto Adhere columns with Tris/Acetate buffer system. The load material was from Protein A affinity capture and pH adjusted. Column flow through pool was collected in each run from 50 mAU of UV A280 on the ascending and 150 mAU on the descending side of the peak. FIG. 21 demonstrates the effect of pH (6.8 to 8.4), conductivity (2.3 to 13.7 mS/cm), and protein load amount (116 to 354 g/L). FIG. 20 demonstrates the AR reduction at conductivity as low as ~1 mS/cm. Table 63 demonstrates the AR reduction at conductivity 86 mS/cm with Ammonia Sulfate-Tris-Acetate buffer system.

The results demonstrated that mAb acidic species can be reduced at wide conductivity ranges from 1 to 86 mS/cm.

TABLE 61

DOE study condition

| Tris Acetate Buffer | Range | Edge points for Response Surface |
|---|---|---|
| pH | 7.6-8.1 | 7.5, 8.2 |
| Conductivity | 2.5-5.0 | 2.0, 5.5 |
| Protein load amount (g/L) | 150-320 | 116, 354 |

TABLE 62

DOE operting condition and results

| pH | Conductivity (mS/cm) | Load amount (g/L) | ΔAR (%) | Yield (%) |
|---|---|---|---|---|
| 7.5 | 3.75 | 235 | 1.7 | 89 |
| 7.6 | 2.5 | 150 | 2.7 | 94 |
| 7.6 | 2.5 | 320 | 2.0 | 95 |
| 7.6 | 5 | 150 | 1.3 | 97 |
| 7.6 | 5 | 320 | 1.1 | 103 |
| 7.85 | 2 | 235 | 3.5 | 94 |
| 7.85 | 3.75 | 116 | 3.2 | 86 |
| 7.85 | 3.75 | 235 | 2.1 | 90 |
| 7.85 | 3.75 | 235 | 2.8 | 90 |
| 7.85 | 3.75 | 354 | 2.2 | 91 |
| 7.85 | 5.5 | 235 | 2.1 | 92 |
| 8.1 | 2.5 | 150 | 5.0 | 80 |
| 8.1 | 2.5 | 320 | 2.6 | 87 |
| 8.1 | 5 | 150 | -0.2 | 95 |
| 8.1 | 5 | 320 | -1.1 | 98 |
| 8.2 | 3.75 | 235 | 2.9 | 90 |

TABLE 63

AR reduction and protein recovery at conductivity of 86 mS/cm and pH 7.9

| Conductivity (mS/cm) | pH | Yield (%) | ΔAR (%) |
|---|---|---|---|
| 86 | 7.9 | 62 | 2.7 |
|  |  | 87 | 2.0 |
|  |  | 91 | 1.8 |
| 86 | 7.9 | 59 | 1.4 |
|  |  | 81 | 1.1 |
|  |  | 94 | 0.7 |

Note:
Adalimumab in Protein A eluate containing 25 mM acetate and 18 mM Tris or 0.89 mM Tris were pH adjusted to pH 3.5 with 3M Acetic acid solution and neutralized to pH 7.9 with 3M Tris solution. One part of this viral inactivated material was then diluted by adding 0.3 part of a stock buffer containing 2.2M (NH$_4$)$_2$SO$_4$/90 mM Tris/60 mM Acetic pH 7.9 to reach conductivity of 86 mS/cm.

6.3.8. Example MM 8: Demonstration of AR Reduction with Different Buffer Systems with Adalimumab In this example, molecule Adalimumab and resin Capto Adhere were chosen. The experiments were performed with different buffer systems listed in the tables below at multiple pH and conductivity condition. The load material pH was adjusted from Protein A eluate or CEX eluate. The results in Table 64 and Table 65 demonstrates that mAb acidic species can be reduced using various buffer systems.

TABLE 64

Effect of Cation type on mAb acidic species reduction and recovery yield

| | | Capto Adhere pH 7.85 | | | HEA pH 7.85 | | | PPA pH 7.85 | | |
|---|---|---|---|---|---|---|---|---|---|---|
| | Operating Condition | 4.5 mS/cm | 3.5 mS/cm | 2.5 mS/cm | 4.5 mS/cm | 3.5 mS/cm | 2.5 mS/cm | 4.5 mS/cm | 3.5 mS/cm | 2.5 mS/cm |
| Tris/Ac | % Yield | 50 | 52 | 58 | 49 | 52 | 56 | 40 | 64 | 63 |
| | Δ% AR | 1.8 | 3.8 | 3.7 | 1.1 | 2.7 | 3.2 | 1.4 | 1.9 | 2.6 |
| | Operating | ~1 mS/cm | | | ~1 mS/cm | | | ~1 mS/cm | | |
| | Condition | pH 8.5 | pH 9.0 | pH 9.5 | pH 8.5 | pH 9.0 | pH 9.5 | pH 8.5 | pH 9.0 | pH 9.5 |
| Arg/Ac | % Yield | 65 | 62 | 49 | 77 | 71 | 66 | 69 | 70 | 71 |
| | Δ% AR | 8.6 | 6.5 | 1.9 | 4.9 | 3.5 | N/R | 4.5 | 1.9 | 0.6 |
| | Operating | ~1 mS/cm | | | ~1 mS/cm | | | ~1 mS/cm | | |
| | Condition | pH 7.85 | pH 8.0 | pH 8.5 | pH 7.85 | pH 8.0 | pH 8.5 | pH 7.85 | pH 8.0 | pH 8.5 |
| Trol/Ac | % Yield | 62 | 54 | 49 | 69 | 64 | 58 | 64 | 64 | 590 |
| | Δ% AR | 4.1 | 6.0 | 4.6 | 1.7 | 2.9 | 3.0 | 1.4 | 2.1 | 2.1 |

Note:
Load material was adalimumab from Protein A affinity capture and pH adjusted

TABLE 65

Effect of Cation type on mAb acidic species reduction and recovery yield

| Buffer | load amount (g/L) | conductivity (mS/cm) | pH | Yield (%) | Δ % AR |
|---|---|---|---|---|---|
| Tris/Ac[1] | 200 | 4.00 | 7.80 | 90 | 1.6 |
| NaPhiosphaste/Citrate/Trolamine/NaCl[2] | 200 | 3.53 | 7.87 | 87 | 1.5 |

Figure 22:
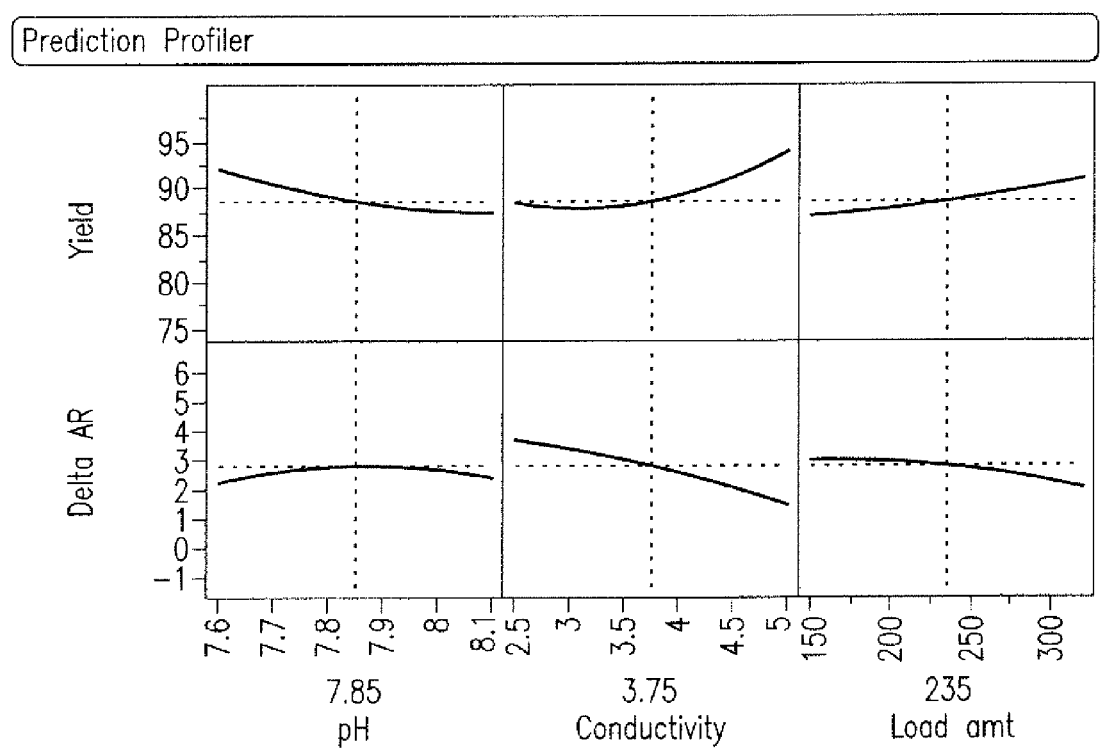
FIG. 22 depicts the effect of pH, conductivity and protein load amount on AR reduction and Yield.

[1] Load material was adalimumab from Protein A affinity capture and pH adjusted
[2] The load material was adalimumab from CEX capture and pH adjusted 6.3.9. Example MM 9: Demonstration of AR Reduction with Different Loading The experiments were performed with Tris/Acetate buffer system under the conditions in table 62. The load material was adalimumab from Protein A affinity capture and pH adjusted. Column flow through pool was collected in each run from 50 mAU of UV A280 on the ascending and 150 mAU on the descending side of the peak. As seen from the profile (FIG. 22), the loading capacity has an impact on AR reduction but the AR reduction can be achieved over a wide range of loading capacities, and is merely a trade-off between AR reduction and recovery.

6.3.10 Example MM 10: Demonstration of AR Reduction with Different Load Concentration In this example, Capto Adhere was chosen. The experiment was performed with Tris/Acetate buffer system at pH 7.8±0.1 and conductivity 3.0±0.05 mS/cm. The load material was adalimumab from concentrated CEX capture and pH adjusted. The prepared load material was then split to be two parts. One was directly loaded on to a Capto adhere column; the other part was diluted 2 folds with equilibration buffer to make different protein concentration. Table 66 demonstrates that the load protein concentration did not have significant impact on mAb acidic species reduction.

TABLE 66

Adalimumab AR Reduction and Yield with Different Load Protein Concentration

| Capture step | Buffer | Load amount (g/L) | Conductivity (mS/cm) | pH | Load protein conc. (g/L) | Yield (%) | Δ % AR |
|---|---|---|---|---|---|---|---|
| CEX | Tris/Ac | 200 | 2.9 | 7.8 | 22.0 | 87 | 2.4 |
| CEX | Tris/Ac | 200 | 3.0 | 7.7 | 11.0 | 89 | 2.1 |
| CEX | NaPhiosphaste/Citrate/Trolamine/NaCl | 200 | 3.5 | 7.9 | 4.9 | 87 | 1.5 |
| Protein A | Tris/Ac | 200 | 3.1 | 7.8 | 9.0 | 89 | 2.5 |
| Protein A | Tris/Ac | 200 | 4.0 | 7.8 | 11.8 | 90 | 1.6 |
| Protein A | Tris/Ac | 200 | 3.0 | 7.8 | 9.9 | 93 | 2.4 |
| Protein A | Tris/Ac | 208 | 3.0 | 7.8 | 8.4 | 95 | 3.2 |
| Protein A | Tris/Ac | 222 | 3.0 | 7.9 | 12.9 | 89 | 3.4 |

6.3.11. Example MM 11: Alternative Wash Modalities

In this example, molecule Adalimumab and resin Capto Adhere were chosen. The experiments were performed with Tris/acetate buffer system and the load material pH was adjusted from Protein A eluates. The equilibration buffer for both run was Tris/Acetic acid pH 7.8±0.1 and conductivity of 3.0±0.1 mS/cm. In the gradient conductivity wash study, second buffer was Tris/Acetic acid pH 7.8±0.1 and conductivity 6.0 mS/cm.

The results demonstrated that post load pH and conductivity can be varied with minimal AR reduction impacted.

6.3.13. Example MM 13: Demonstration of HCP and Aggregate Reduction in Addition to AR Reduction Besides the acidic species reduction, the MM adsorbent is able to reduce other product/process related substances/impurities effectively. In the implementation of the current invention the fact that AR reduction is effected, other impurities/substances are expected to be cleared significantly as they should bind stronger than the acidic species. The data shown in Table 69 and Table 70 demonstrates significant HCP and aggregate reductions with different resins, buffer systems, pH, conductivities and molecules

TABLE 67

Comparison of AR reduction and yield under different wash conditions

| Experiment | Wash | Load conductivity (mS/cm) | load pH | Load conc (mg/mL) | Yield (%) | Wash CV | Δ% AR |
|---|---|---|---|---|---|---|---|
| Equilibration buffer wash | Equilibration buffer (Tris/Ac pH 7.8 and 3.0 mS/cm) wash only | 3.09 | 7.85 | 9.04 | 89 | 16.4 | 2.5 |
| Gradient conductivity wash | 1CV Equilibration buffer 10CV gradient conductivity wash from 100% Tris/Ac pH 7.8, 3.0 mS/cm to 100% Tris/Ac pH 7.8, 6 mS/cm. | 3.04 | 7.78 | 7.17 | 91 | 8.0 | 2.2 |

6.3.12. Example MM 12: Demonstration of Achievement of Absolute Value of AR Levels in Antibody Preparations Using Mixed Mode Chromatography In this example, molecule Adalimumab was chosen. The experiments were performed with multiple buffer systems and multiple MM absorbents under conditions listed in Table 68. The load materials pH was adjusted from Protein A eluates.

The Acidic Region for Adalimumab is further grouped into two regions termed AR1 and AR2, based on a certain retention time of the peaks seen on the WCX-10 method. The characteristics of the variants in these two regions are expected to be different and hence the methods that reduce variants belonging to these groups can be specifically delineated. Further, in addition to achieving a certain AR reduction, it may be desirable to achieve a certain absolute level of AR levels, in consideration of reducing or removing certain variants. The capability of the current invention in achieving a certain absolute level of AR, AR1 and AR2 is demonstrated in Table 68.

TABLE 68

Acidic species level in MM resin flowthrough

| Resin | Buffer | pH | Conductivity (mS/cm) | Yield (%) | FT % AR1 | FT % AR2 |
|---|---|---|---|---|---|---|
| Capto Adhere | Tris/Ac | 7.85 | 4.5 | 50 | 2.8 | 9.7 |
| | | 7.85 | 4.5 | 68 | 3.0 | 10.3 |
| | | 7.85 | 3.5 | 52 | 1.6 | 10.0 |
| | | 7.85 | 3.5 | 71 | 12 | 10.5 |
| | | 7.85 | 3.0 | 93 | 3.2 | 9.7 |
| | | 7.85 | 2.5 | 58 | 1.7 | 9.4 |
| | | 7.85 | 2.5 | 72 | 2.2 | 10.0 |
| | Arg/Ac | 8.5 | 1 | 65 | 1.2 | 6.1 |
| | | 9.0 | 1 | 62 | 1.6 | 7.2 |
| | | 9.5 | 1 | 49 | 0.8 | 11.8 |
| | Trol/Ac | 7.9 | 1 | 44 | 1.5 | 6.6 |
| | | 7.9 | 1 | 62 | 1.8 | 8.0 |
| | | 8.0 | 1 | 37 | 1.1 | 5.8 |
| | | 8.0 | 1 | 54 | 1.2 | 7.7 |
| | | 8.5 | 1 | 32 | 1.7 | 9.0 |
| | | 8.5 | 1 | 49 | 1.9 | 10.1 |
| HEA | Arg/Ac/ | 8.5 | 1 | 77 | 1.6 | 8.5 |
| | | 9.0 | 1 | 71 | 0.8 | 12.0 |
| PPA | | 8.5 | 1 | 69 | 2.2 | 8.7 |
| | | 9.0 | 1 | 70 | 1.0 | 13.5 |
| | | 9.5 | 1 | 71 | 0.7 | 13.1 |

TABLE 69

Aggregates reduction

| | Conductivity (mS/cm) | pH | Buffer | medium | Δ % HMW |
|---|---|---|---|---|---|
| D2E7 | 3.75 | 7.5 | Tris/Ac | Capto Adhere | 0.7 |
| | 2.5 | 7.6 | Tris/Ac | | 0.9 |
| | 2 | 7.85 | Tris/Ac | | 0.9 |
| | 3.75 | 7.85 | Tris/Ac | | 1.0 |
| | 5.5 | 7.85 | Tris/Ac | | 0.7 |
| | 2.5 | 8.1 | Tris/Ac | | 1.0 |
| | 3.75 | 8.2 | Tris/Ac | | 0.8 |
| | 4.0 | 8.2 | Tris/Ac | | 1.0 |
| | 8.0 | 6.8 | Tris/Ac | | 0.2 |
| | 8.0 | 8.4 | Tris/Ac | | 1.0 |
| | 1.0 | 8.5 | Arg/Ac | Capto Adhere | 0.5 |
| | 1.0 | 9.0 | Arg/Ac | | 0.8 |
| | 1.0 | 9.5 | Arg/Ac | | 0.9 |
| | 1.0 | 8.5 | Arg/Ac | HEA | 0.4 |
| | 1.0 | 9.0 | Arg/Ac | | 2.5 |
| | 1.0 | 9.5 | Arg/Ac | | 0.7 |
| | 1.0 | 8.5 | Arg/Ac | PPA | 0.5 |
| | 1.0 | 9.0 | Arg/Ac | | 2.8 |
| | 1.0 | 9.5 | Arg/Ac | | 0.4 |
| MAB C | 3.0 | 8 | Tris/Ac | Capto Adhere | 1.0 |
| | 3.0 | 8.5 | Tris/Ac | Capto Adhere | 1.1 |
| | 3.0 | 9 | Tris/Ac | Capto Adhere | 0.6 |
| | 3.0 | 8 | Tris/Ac | PPA | 0.7 |
| | 3.0 | 8.5 | Tris/Ac | PPA | 0.5 |
| | 3.0 | 8 | Tris/Ac | HEA | 0.7 |
| | 3.0 | 8.5 | Tris/Ac | HEA | 0.6 |

TABLE 70

HCP Log reduction

| | Condutivity (mS/cm) | pH | Buffer | medium | HCP LRF |
|---|---|---|---|---|---|
| D2E7 | 3.75 | 7.5 | Tris/Ac | Capto Adhere | 1.5 |
| | 2.5 | 7.6 | Tris/Ac | | 1.7 |
| | 2.0 | 7.85 | Tris/Ac | | 2.2 |
| | 3.75 | 7.85 | Tris/Ac | | 1.9 |
| | 5.5 | 7.85 | Tris/Ac | | 1.4 |

TABLE 70-continued

HCP Log reduction

| | Condutivity (mS/cm) | pH | Buffer | medium | HCP LRF |
|---|---|---|---|---|---|
| | 2.5 | 8.1 | Tris/Ac | | 2.3 |
| | 3.75 | 8.2 | Tris/Ac | | 2.1 |
| | 4.0 | 8.2 | Tris/Ac | | 1.7 |
| | 8.0 | 6.8 | Tris/Ac | | 0.3 |
| | 8.0 | 8.4 | Tris/Ac | | 0.7 |
| MAB B | 3 | 6.8 | Tris/Ac | Capto Adhere | 2.0 |
| | 4.5 | 6.8 | Tris/Ac | Capto Adhere | 1.3 |
| | 3 | 6.8 | Tris/Ac | PPA | 1.2 |
| | 4.5 | 6.8 | Tris/Ac | | 1.2 |
| | 3 | 6.8 | Tris/Ac | HEA | 1.3 |
| | 4.5 | 6.8 | Tris/Ac | | 1.1 |

6.3.14. Example MM 14: Combinations of MM with Alternative Separation Strategies Acidic Species Reduction by MM Adsorbents is expected to be performed after capture of the antibody by other means, or after one or more intermediate steps following the capture step. In the examples below the MM Adsorbent steps were performed either following a Cation Exchange Capture step or Protein A affinity capture step. As shown in Table 71, AR reduction was achieved at two different conductivities following Protein A Chromatography and CEX Chromatography.

TABLE 71

AR Reduction with different source materials

| Capture | Buffer | conductivity (mS/cm) | pH | Yield (%) | Δ % AR |
|---|---|---|---|---|---|
| Protein A | Tris/Ac | 3.1 | 7.8 | 89 | 2.5 |
| Protein A | Tris/Ac | 4.0 | 7.8 | 90 | 1.6 |
| CEX | Tris/Ac | 2.9 | 7.8 | 87 | 2.4 |
| CEX | Tris/Ac | 3.0 | 7.7 | 89 | 2.1 |

Adalimumab was purified by a CEX chromatography step followed with a low pH viral inactivation step. The filtered viral inactivated material was buffer exchanged and loaded onto a Capto Adhere column. The flowthrough of Capto Adhere material was then purified with a HIC column with bind/elute mode. As shown in Table 72, AR reduction was achieved primarily with MM step, with some contribution from other steps.

TABLE 72

Complete Process train with CEX Chromatography Capture- AR Reduction

| | Δ % AR | Δ % Lys | Yield (%) |
|---|---|---|---|
| CEX eluate | n/a | n/a | n/a |
| MM Load | 0.29 | 0.34 | 90% |
| MM Flowthrough | 2.57 | 2.57 | 93% |
| HIC eluate | 0.95 | 0.94 | 97% |

Adalimumab was purified by a Protein A chromatography step followed with a low pH viral inactivation step. The filtered viral inactivated material was buffer exchanged and loaded onto a Capto Adhere column. The flowthrough of Capto Adhere material was then purified with a HIC column with bind/elute mode as well as Flow Through mode. As shown in Table 73, AR reduction was achieved primarily with MM step, with some contribution from other steps.

TABLE 73

Complete Process Train with Protein A Capture - AR, HMW and HCP reduction

| Process | Yield (%) | % AR reduction | % HMW reduction | HCP LRF |
|---|---|---|---|---|
| Clarified Harvest | 97.0% | n/a | n/a | n/a |
| Prt-A Eluate Pool | 89.6% | 0.06 | | 1.87 |
| Viral Inactivated Filtrate | 99.7% | No reduction | 0.07 | 0.39 |
| MM FT pool | 91.9% | 2.26 | 0.83 | 1.63 |
| HIC (B/E) Eluate | 90.1% | 0.40 | 0.22 | 1.41 |
| Nanofiltrate Filtrate | 90.7% | No reduction | No reduction | 0.15 |
| BDS (B/E) | 102.0% | No reduction | No reduction | 0.22 |
| HIC FT-pool | 98.5% | 0.16 | 0.23 | 0.46 |
| VF(FT) Filtrate | 96.1% | No reduction | No reduction | 0.10 |
| BDS (FT) | 103.8% | No reduction | No reduction | No reduction |

6.3.15. Example MM 15: Utility of AR Reduction

The current invention provides a method for reducing acidic species for a given protein of interest. In this example adalimumab was prepared using a combination of AEX and CEX technologies to produce a Low-AR and High-AR sample with a final AR of 2.5% and 6.9%, respectively. Both samples were incubated in a controlled environment at 25° C. and 65% relative humidity for 10 weeks, and the AR measured every two weeks. FIG. 23 shows the growth of AR for each sample over the 10 week incubation. It is evident from FIG. 23 the growth rate of AR is linear and similar between both the Low-AR and High-AR samples. Based on these results the reduced AR material can be stored 3 fold longer before reaching the same AR level as the High-AR sample. This is a significant utility as this can be very beneficial in storage handling and use of the antibody or other proteins for therapeutic use.

6.4 Process Combinations to Achieve Target % Ar or Ar Reductions

Upstream and Downstream process technologies, e.g., cell culture and chromatographic separations, of the inventions disclosed in the following applications can be combined together or combined with methods in the art to provide a final target AR value or achieve a % AR reduction, as well as to, in certain embodiments, reduce product related substances and/or process related impurities. Upstream methods for AR reduction include, but are not limited to those described in the in the U.S. patent application having U.S. Serial No. 13/830, 583. Downstream methods for AR reduction include, but are not limited to, those described in the instant application. Exemplary technologies disclosed in the referenced applications include, but are not limited to: cell culture additives & conditions; clarified harvest additives and pH/salt conditions; mixed mode media separations; anion exchange media separations; and cation Exchange media separations.

The instant example demonstrates the combined effect of one or more of these technologies in achieving a target AR value or AR reduction, thereby facilitating the preparation of an antibody material having a specific charge heterogeneity. Additional examples of combinations of downstream technologies and upstream technologies are provided in the referenced applications.

In this example, the combination of upstream and downstream methods involves the reduction of acidic species in 3 L bioreactor cell cultures supplemented with arginine (2 g/l) and lysine (4 g/l) as has been previously demonstrated in the U.S. patent application having U.S. Ser. No. 13/830,583. The results of that strategy are summarized in Table 74. The total acidic species was reduced from 20.5% in the control sample to 10.2% in sample from cultures that were supplemented with the additives. In this study, Adalimumab producing cell line 1 was cultured in media 1 (chemically defined media) supplemented with amino acid arginine (2 g/l) and lysine (4 g/l) in a 300 L bioreactor. On Day 12 of culture, the culture was harvested and then subsequently analyzed using WCX-10 post protein A purification and the percentages of total peak(s) area corresponding to the acidic species were quantified. The percentage of acidic species was estimated to be 9.1% in the 300 L harvest sample.

TABLE 74

AR levels achieved with use of upstream technologies

| 3 L Bioreactor | | | | | | 300 L Bioreactor | | |
|---|---|---|---|---|---|---|---|---|
| Control | | | Arginine (2 g/l) + Lysine (4 g/l) | | | Arginine (2 g/l) + Lysine (4 g/l) | | |
| AR1 (%) | AR2 (%) | Total AR (%) | AR1 (%) | AR2 (%) | Total AR (%) | AR1 (%) | AR2 (%) | Total AR (%) |
| 6.3 | 14.2 | 20.5 | 2.6 | 7.6 | 10.2 | 2.4 | 6.7 | 9.1 |

The material produced by the 300 L Bioreactor employing Arginine and Lysine additions, that effectively reduced the AR levels to 9.1% was purified using a downstream process employing Mixed Mode chromatography as the primary AR Reduction method.

Adalimumab was purified by a Protein A chromatography step followed with a low pH viral inactivation step. The filtered viral inactivated material was buffer exchanged and loaded onto a Capto Adhere column. The flowthrough of Capto Adhere material was then purified with a HIC column with bind/elute mode as well as Flow Through mode. As shown in Table 75, AR reduction was achieved primarily with MM step, with some contribution from other steps. The table also shows that additional product related substances such as aggregates and process related impurities such as HCP can be effectively reduced employing these combined technologies.

TABLE 75

Complete Downstream Process Train with Protein A Capture - AR, HMW and HCP reduction

| Process | Yield (%) | % AR reduction | % HMW reduction | HCP LRF |
|---|---|---|---|---|
| Clarified Harvest | 97.0% | n/a | n/a | n/a |
| Prt-A Eluate Pool | 89.6% | 0.06 | | 1.87 |
| Viral Inactivated Filtrate | 99.7% | No reduction | 0.07 | 0.39 |
| MM FT pool | 91.9% | 2.26 | 0.83 | 1.63 |
| HIC (B/E) Eluate | 90.1% | 0.40 | 0.22 | 1.41 |
| Nanofiltrate Filtrate | 90.7% | No reduction | No reduction | 0.15 |
| BDS (B/E) | 102.0% | No reduction | No reduction | 0.22 |
| HIC FT-pool | 98.5% | 0.16 | 0.23 | 0.46 |
| VF(FT) Filtrate | 96.1% | No reduction | No reduction | 0.10 |
| BDS (FT) | 103.8% | No reduction | No reduction | No reduction |

As is evident from the above example, the MM method further reduced the AR levels, by 2.26%. Therefore upstream technologies for reduction can be combined with downstream technologies to achieve AR levels/AR reduction.

Patents, patent applications, publications, product descriptions, GenBank Accession Numbers, and protocols that may be cited throughout this application, the disclosures of which are incorporated herein by reference in their entireties for all purposes. For example, but not by way of limitation, patent applications designated by the following U.S. application Ser. Nos. numbers are incorporated herein by reference in their entireties for all purposes: 13/803,808; 13/830,583; 13/830,976; 13/831,181; and 13/804,220.

What is claimed is:

1. A composition comprising adalimumab, wherein the composition comprises less than 10% total acidic species of adalimumab, wherein the acidic species of adalimumab correspond to the peaks that elute earlier than the main peak in a WCX-10 HPLC chromatogram of adalimumab, wherein the WCX-10 HPLC chromatogram is generated using a first mobile phase of 10 mM Sodium Phosphate dibasic (pH 7.5) and a second mobile phase of 10 mM Sodium Phosphate dibasic, 500 mM Sodium Chloride (pH 5.5), and wherein the WCX-10 HPLC chromatogram is generated using detection at 280 nm.

2. The composition of claim 1, wherein the acidic species of adalimumab comprise a first acidic region (AR1) and a second acidic region (AR2).

3. The composition of claim 1, wherein the composition comprises less than 3.8% total acidic species of adalimumab.

4. The composition of claim 2, wherein the composition comprises 0.8% AR1 and 3.0% AR2.

5. The composition of claim 1, wherein the composition comprises less than 2.4% total acidic species of adalimumab.

6. The composition of claim 2, wherein the composition comprises 0.2% AR1 and 2.2% AR2.

7. The composition of claim 1, wherein the composition comprises 4.7%-8.3% total acidic species of adalimumab.

8. The composition of claim 7, wherein the composition comprises 4.7% total acidic species of adalimumab.

9. The composition of claim 7, wherein the composition comprises 5.0% total acidic species of adalimumab.

10. The composition of claim 7, wherein the composition comprises 5.8% total acidic species of adalimumab.

11. The composition of claim 7, wherein the composition comprises 6.1% total acidic species of adalimumab.

12. The composition of claim 7, wherein the composition comprises 6.4% total acidic species of adalimumab.

13. The composition of claim 7, wherein the composition comprises 8.1% total acidic species of adalimumab.

14. The composition of claim 7, wherein the composition comprises 8.3% total acidic species of adalimumab.

15. The composition of claim 2, wherein the composition comprises 0.8%-1.4% AR1.

16. The composition of claim 2, wherein the composition comprises 3%-9% AR2.

17. The composition of claim 2, wherein the composition comprises 0.8% AR1 and 6.4% AR2.

18. The composition of claim 2, wherein the composition comprises 0.9% AR1 and 9% AR2.

19. The composition of claim 2, wherein the composition comprises 1.2% AR1 and 7.7% AR2.

20. The composition of claim 2, wherein the composition comprises 1.2% AR1 and 8.2% AR2.

21. The composition of claim 2, wherein the composition comprises 1.4% AR1 and 8.4% AR2.

22. The composition of claim 2, wherein the composition comprises 1.4% AR1 and 8.6% AR2.

23. The composition of claim 1, wherein the composition further comprises a pharmaceutically acceptable carrier.

24. A pharmaceutical composition suitable for administration to a human subject, comprising a composition comprising adalimumab, wherein the composition comprises less than 10% total acidic species of adalimumab, wherein the acidic species of adalimumab correspond to the peaks that elute earlier than the main peak in a WCX-10 HPLC chromatogram of adalimumab, wherein the WCX-10 HPLC chromatogram is generated using a first mobile phase of 10 mM Sodium Phosphate dibasic (pH 7.5) and a second mobile phase of 10 mM Sodium Phosphate dibasic, 500 mM Sodium Chloride (pH 5.5), and wherein the WCX-10 HPLC chromatogram is generated using detection at 280 nm;

and a pharmaceutically acceptable carrier.

25. The pharmaceutical composition of claim 24, wherein the acidic species of adalimumab comprise a first acidic region (AR1) and a second acidic region (AR2).

26. The pharmaceutical composition of claim 24, wherein the composition comprises less than 3.8% total acidic species of adalimumab.

27. The pharmaceutical composition of claim 25, wherein the composition comprises 0.8% AR1 and 3.0% AR2.

28. The pharmaceutical composition of claim 24, wherein the composition comprises less than 2.4% total acidic species of adalimumab.

29. The pharmaceutical composition of claim 25, wherein the composition comprises 0.2% AR1 and 2.2% AR2.

30. The pharmaceutical composition of claim 24, wherein the composition comprises 4.7%-8.3% total acidic species of adalimumab.

31. The pharmaceutical composition of claim 30, wherein the composition comprises 4.7% total acidic species of adalimumab.

32. The pharmaceutical composition of claim 30, wherein the composition comprises 5.0% total acidic species of adalimumab.

33. The pharmaceutical composition of claim 30, wherein the composition comprises 5.8% total acidic species of adalimumab.

34. The pharmaceutical composition of claim 30, wherein the composition comprises 6.1% total acidic species of adalimumab.

35. The pharmaceutical composition of claim 30, wherein the composition comprises 6.4% total acidic species of adalimumab.

36. The pharmaceutical composition of claim 30, wherein the composition comprises 8.1% total acidic species of adalimumab.

37. The pharmaceutical composition of claim 30, wherein the composition comprises 8.3% total acidic species of adalimumab.

38. The pharmaceutical composition of claim 25, wherein the composition comprises 0.8%-1.4% AR1.

39. The pharmaceutical composition of claim 25, wherein the composition comprises 3%-9% AR2.

40. The pharmaceutical composition of claim 25, wherein the composition comprises 0.8% AR1 and 6.4% AR2.

41. The pharmaceutical composition of claim 25, wherein the composition comprises 0.9% AR1 and 9% AR2.

42. The pharmaceutical composition of claim 25, wherein the composition comprises 1.2% AR1 and 7.7% AR2.

43. The pharmaceutical composition of claim 25, wherein the composition comprises 1.2% AR1 and 8.2% AR2.

44. The pharmaceutical composition of claim 25, wherein the composition comprises 1.4% AR1 and 8.4% AR2.

45. The pharmaceutical composition of claim 25, wherein the composition comprises 1.4% AR1 and 8.6% AR2.

46. The composition of any one of claims 1-23, wherein the composition is a lyophilized composition.

47. The pharmaceutical composition of any one of claims 24-45, wherein the composition is a lyophilized composition.

48. The composition of any one of claims 1-23, wherein the adalimumab is produced in a mammalian host cell grown in cell culture.

49. The composition of claim 48, wherein the mammalian host cell is selected from the group consisting of a CHO cell, an NSO cell, a COS cell, and an SP2 cell.

50. The composition of claim 49, wherein the mammalian host cell is a CHO cell.

51. The pharmaceutical composition of any one of claims 24-45, wherein the adalimumab is produced in a mammalian host cell grown in cell culture.

52. The pharmaceutical composition of claim 51, wherein the mammalian host cell is selected from the group consisting of a CHO cell, an NSO cell, a COS cell, and an SP2 cell.

53. The pharmaceutical composition of claim 52, wherein the mammalian host cell is a CHO cell.

54. The pharmaceutical composition of any one of claims 24-45, wherein adalimumab is present in the pharmaceutical composition at a concentration of 0.1-250 mg/mL.

55. The pharmaceutical composition of any one of claims 24-45, wherein the pharmaceutically acceptable carrier comprises mannitol.

56. The pharmaceutical composition of any one of claims 24-45, wherein the pharmaceutically acceptable carrier comprises sodium chloride.

57. The pharmaceutical composition of any one of claims 24-45, wherein the pharmaceutically acceptable carrier comprises polysorbate 80.

58. The pharmaceutical composition of any one of claims 24-45, wherein the pharmaceutically acceptable carrier comprises a buffer.

59. The pharmaceutical composition of claim 58, wherein the buffer is sodium citrate.

60. The pharmaceutical composition of claim 58, wherein the buffer is histidine.

61. A pre-filled syringe which contains the pharmaceutical composition of any one of claims 24-45.

* * * * *